US009442013B2

(12) United States Patent
Iga

(10) Patent No.: US 9,442,013 B2
(45) Date of Patent: Sep. 13, 2016

(54) MICROSCOPE SPECTROMETER, OPTICAL AXIS SHIFT CORRECTION DEVICE, SPECTROSCOPE AND MICROSCOPE USING SAME

(71) Applicant: YOKOGAWA ELECTRIC CORPORATION, Musashino-shi, Tokyo (JP)

(72) Inventor: Mitsuhiro Iga, Musashino (JP)

(73) Assignee: YOKOGAWA ELECTRIC CORPORATION, Tokyo (JP)

( * ) Notice: Subject to any disclaimer, the term of this patent is extended or adjusted under 35 U.S.C. 154(b) by 149 days.

(21) Appl. No.: 13/897,981

(22) Filed: May 20, 2013

(65) Prior Publication Data
US 2013/0258332 A1 Oct. 3, 2013

Related U.S. Application Data

(63) Continuation of application No. PCT/JP2011/072771, filed on Oct. 3, 2011.

(30) Foreign Application Priority Data

Nov. 22, 2010 (JP) .................. 2010-259921
Dec. 15, 2010 (JP) .................. 2010-279100
Dec. 16, 2010 (JP) .................. 2010-280576

(51) Int. Cl.
*G01J 3/44* (2006.01)
*G01J 3/06* (2006.01)
(Continued)

(52) U.S. Cl.
CPC ............ *G01J 3/4412* (2013.01); *G01J 3/0227* (2013.01); *G01J 3/06* (2013.01); *G01J 3/26* (2013.01);
(Continued)

(58) Field of Classification Search
CPC ...................................... G01J 3/4412
USPC ......................................... 356/416
See application file for complete search history.

(56) References Cited

U.S. PATENT DOCUMENTS 2,544,196 A * 3/1951 Varden .................. 356/404
3,914,055 A 10/1975 Wolga et al.
(Continued)

FOREIGN PATENT DOCUMENTS

JP 51-27383 A 3/1976
JP 7-9730 B2 2/1995
(Continued)

OTHER PUBLICATIONS

International Search Report for PCT/JP2011/072771, mailing date of Jan. 17, 2012, With English translation.
(Continued)

*Primary Examiner* — Kara E Geisel
*Assistant Examiner* — Omar Nixon
(74) *Attorney, Agent, or Firm* — Westerman, Hattori, Daniels & Adrian, LLP

(57) ABSTRACT

A microscope spectrometer in which, when an excitation light from a light source illuminates a sample, a light emitted from the sample that enters a microscope is analyzed, may include: a first optical means that forms the light emitted from the sample as a parallel beam; a first variable bandpass filter means having a variable wavelength passband that transmits incident light, which of the parallel beam of incident light, is light of a pre-established wavelength passband; a two-dimensional array light detection means that images the light in the wavelength passband; and a control means that controls the timing of the imaging by the two-dimensional array light detection means and, in accordance with the timing, changes the wavelength passband of the first variable bandpass filter means.

12 Claims, 28 Drawing Sheets

(51) Int. Cl.
  *G01J 3/26* (2006.01)
  *G01J 3/32* (2006.01)
  *G01N 21/65* (2006.01)
  *G01J 3/02* (2006.01)
  *G01J 3/12* (2006.01)
  *G02B 21/00* (2006.01)

(52) U.S. Cl.
  CPC .. *G01J 3/32* (2013.01); *G01J 3/44* (2013.01); *G01N 21/658* (2013.01); *G01J 2003/1213* (2013.01); *G01J 2003/1226* (2013.01); *G01J 2003/1243* (2013.01); *G02B 21/0076* (2013.01)

(56) References Cited

U.S. PATENT DOCUMENTS

| | | | | |
|---|---|---|---|---|
| 4,494,875 | A * | 1/1985 | Schramm et al. | 356/402 |
| 5,287,214 | A | 2/1994 | Robertson et al. | |
| 6,262,837 | B1 * | 7/2001 | Nagano et al. | 359/368 |
| 6,312,423 | B1 * | 11/2001 | Ota | A61F 9/008 351/206 |
| 2005/0128476 | A1 * | 6/2005 | Zhao | 356/301 |
| 2005/0140957 | A1 * | 6/2005 | Luijkx et al. | 355/71 |
| 2007/0035819 | A1 * | 2/2007 | Bahatt et al. | 359/366 |
| 2008/0018988 | A1 * | 1/2008 | Davidson | 359/341.1 |

FOREIGN PATENT DOCUMENTS

| | | |
|---|---|---|
| JP | 08-178751 A | 7/1996 |
| JP | 08-261826 A | 10/1996 |
| JP | 10-062238 A | 3/1998 |
| JP | 2733491 B | 3/1998 |
| JP | 10-115781 A | 5/1998 |
| JP | 2834954 B2 | 12/1998 |
| JP | 2002-014043 A | 1/2002 |
| JP | 2004-317676 A | 11/2004 |
| JP | 2005-234264 A | 9/2005 |
| JP | 2007-179002 A | 7/2007 |
| JP | 2011-220700 A | 11/2011 |

OTHER PUBLICATIONS

Mitsushiro Iga, "2-Dimensional spectral imaging unit for living cell(s) monitoring based on surface enhanced Raman scattering", Corp. R&D, Yokogawa Electric Corporation (2011).

M. Iga et al., "Hyperspectral optical unit for SERS imaging of living cell", Sensing Technology Research Center, Corporate R&D, Yokogawa Electric Corporation.

Mitsushiro Iga, "2-Dimensional real-time spectral imaging unit based on Surface Enhanced Raman Scattering for living cell(s) imaging", Sensing RC, Corp. R&D HQ, Yokogawa Electric Corporation.

M. Iga et al, "Surface Enhanced Raman Imaging by Microscopis Spectral Unit", Yokogawa Electric Corp.CR&D, With English translation.

* cited by examiner

MICROSCOPE SPECTROMETER, OPTICAL AXIS SHIFT CORRECTION DEVICE, SPECTROSCOPE AND MICROSCOPE USING SAME

CROSS REFERENCE TO RELATED APPLICATIONS

This application is a continuation application based on a PCT Patent Application No. PCT/JP2011/072771, filed Oct. 3, 2011, whose priority is claimed on Japanese Patent Application No. 2010-259921 filed Nov. 22, 2010, Japanese Patent Application No. 2010-279100 filed Dec. 15, 2010, and Japanese Patent Application No. 2010-280576 filed Dec. 16, 2010, the entire contents of which are hereby incorporated by reference.

BACKGROUND OF THE INVENTION

1. Field of the Invention

The present invention relates to a microscope spectrometer for analyzing multiple scattered light emitted from a sample across a wide wavelength range, the light being incident to the microscope, when excitation light is directed from a light source onto the sample.

In particular, the present invention relates to a microscope spectrometer capable of high-speed spectrometry with a wavelength resolution having a pre-established spacing. Specifically, it relates to a microscope spectrometer used when measuring Raman scattered light or SERS (surface-enhanced Raman scattering) scattered light.

The present invention also relates to an optical axis shift correction device, and specifically to a mechanism for correcting the optical axis shift in an optical system.

The present invention also relates to a spectroscope, and particularly, to a spectroscope that is effective in measurement of Raman scattered light.

The present invention also relates to a spectroscope and a microscope using the spectroscope. In particular, it relates to a planar spectroscope for the purpose of measuring Raman shift and a microscope using the planar spectroscope.

2. Description of the Related Art

All patents, patent applications, patent publications, scientific articles, and the like, which will hereinafter be cited or identified in the present application, will hereby be incorporated by reference in their entirety in order to describe more fully the state of the art to which the present invention pertains.

Conventionally proposed microscope spectrometers have performed spectral analysis, via a microscope, of the excitation light, fluorescent light, and Raman scattered light occurring when an excitation laser beam illuminates a sample (object under measurement).

In this case, the term Raman scattered light refers to an inelastic optical phenomenon occurring when a substance is illuminated by a single wavelength from a laser or the like. It is the phenomenon of scattered light that is slightly shifted toward the long-wavelength side and toward the short-wavelength side, relative to the wavelength of the illuminating single-wavelength light source. In Raman scattering, if the intensity of the illuminating light is taken to be 1, only a tiny light intensity of approximately $10^{-14}$ is obtainable.

The Raman scattering light spectrum of the wavelength shift (Rama shift) is characteristic of the particular substance. Thus, it is possible to identify the substance of a sample based on the Raman scattered light.

For this reason, a conventional microscope spectrometer, by detecting Raman scattered light and the like emitted from a sample, could identify the chemical structure and the physical condition of substances included in a sample. With a conventional microscope spectrometer, it was possible to perform detection non-destructively, regardless of whether the sample was a solid, a liquid, or a gas.

SERS is the phenomenon in which, when a substance exists surrounding a nano-sized metal structure in a sample that is an object under measurement, scattered light occurs by illumination with a single wavelength, such as from a laser. More specifically, SERS is a phenomenon in which the Raman scattered light is enhanced.

Specifically, when excitation light illuminates a sample having a metal nano-structure, surface plasmons, which are expanded/compressed waveforms of free electrons at the metal surface are excited, and the photoelectric field in the region thereof is strengthened. As a result, with regard to SERS, a conventional microscope spectrometer measured Raman scattered light that has been enhanced by surface plasmons generated in the area surrounding the metal nano-structure.

FIG. 11 is a drawing showing an example of the constitution of a conventional microscope spectrometer.

In FIG. 11, the microscope spectrometer is analyzing a sample 9, which is an example regarding illuminating light. The microscope spectrometer has a light source 1 that emits an excitation light, a Y scanning device 2 that scans the excitation light incident from the light source 1 in the Y direction of the X and Y directions in a plane that is perpendicular to the optical axis, a beam splitter 3 disposed in the light path from the Y scanning device 2 to the sample, and that splits the light beam incident to the sample (incident light) into light exiting the objective lens 5 side from the sample that has changed to a different wavelength and the excitation light (incident light) that is incident to the sample from the light source, an X scanning device 4 that scans the incident light in the X direction of the X and Y directions (horizontal directions), an objective lens 5, an entrance slit 6 disposed along a direction corresponding to the Y direction, a spectroscopic unit 7 that spatially disperse the light passing through and exiting from the entrance slit in accordance with its wavelengths, and a two-dimensional array light detection means 8 that detects the exiting light that is dispersed by the spectroscopic unit 7.

The Y scanning device 2 changes the exiting angle of and deflects the incident light. By doing this, the position of incidence of the incident light on the sample changes along the Y direction. That is, the Y scanning device 2 scans the incident light in the Y direction.

The Y scanning device scans the excitation light at least one time in the Y direction during one frame of imaging by the two-directional array light detection means (or, stated differently, with a scanning period that is shorter than the exposure time for one frame).

When this occurs, the position of incidence of the excitation light from the light source moves from one end to the other end of the Y scanning range on the entrance slit 6 within the exposure time.

The spectroscopic unit 7 distribute (spectrally disperses) the exiting light that passes through the entrance slit 6 in accordance with its wavelengths (spectrally) and exits the light to the two-directional array light detection means 8.

The exiting light is dispersed by the spectroscopic unit 7 in a direction that is perpendicular to the direction of the entrance slit. That is, the spectroscopic unit 7 acts to perform wavelength dispersion of the exiting light in a direction that is perpendicular to the linear aperture of the entrance slit 6.

The spectroscopic unit 7 has an optical element such as diffraction grating or prism, and spatially disperses the light incident from the entrance slit 6 in accordance with the wavelengths thereof.

The two-directional array light detection means 8 detects the Raman scattered light in the linear region of the sample (the region on the sample corresponding to the aperture of the entrance slit 6) obtained by the scanning of the light beam by the Y scanning device 2 during one exposure.

Specifically, if the two-directional array light detection means 8 has a constitution with n rows×m columns of pixels, the two-directional array light detection means 8 measures the spectrum at m points on the sample with one exposure.

When the imaging of one frame is completed, the X scanning device 4 offsets the position of incidence of the incident light on the sample by one illumination region in the X direction or, stated differently, scans the incident light in the X direction.

Specifically, the X scanning device 4 changes the angle of the reflecting surface and deflects the incident light to shift the position of incidence thereof on the sample in the X direction by one illumination region.

Once again, the Y scanning device 2 scans the excitation light in the Y direction during one frame of imaging by the two-directional array light detection means 8, the two-directional array light detection means 8 detects the Raman scattered light, and the X scanning device 4 scans the incident light in the X direction.

For a two-directional array light detection means 8 having a constitution of n rows×m columns of pixels, these operations are performed n times.

Based on the image data for one frame imaged by one exposure by the two-directional array light detection means 8, an analyzer (not shown) can measure the spectrum of the Raman scattered light in the linear region in accordance with the scanning range or, stated differently can measure the spectrum of the Raman scattered light occurring at a plurality of points (positions).

By the above, in a conventional microscope spectrometer, because it is possible for the two-dimensional array light detection means 8 to detect the spectrum from a plurality of points (positions) on a sample with a single exposure, it is not necessary to transfer the image data imaged at each point individually, thereby enabling a reduction in the number of charge transfers in the CCD of the two-dimensional array light detection means 8 and also the number of transfers of data from the CCD, thereby enabling a shortening of the measurement time.

Conventional microscope spectrometers are described in Japanese Unexamined Patent Application, First Publication No. 2007-179002, Japanese Unexamined Patent Application, First Publication No. 2004-317676, Japanese Unexamined Patent Application, First Publication No. 2002-014043, and the like.

Conventionally, in observing a sample using an optical microscope having an afocal observation optical system, prescribed optical components have been inserted into and removed from the optical system, depending on the sample to be observed.

Japanese Unexamined Patent Application, First Publication No. H10-115781 discloses an optical microscope that, by preventing shifting of the optical axis when switching by insertion or removal of optical components in the afocal observation light path, precise multiple observation of a sample is possible.

FIG. 19 shows the constitution of an optical microscope having an afocal observation optical system described in Japanese Unexamined Patent Application, First Publication No. H10-115781. In FIG. 19, in performing fluorescent dye observation, a fluorescence cube 356 that combines a dichroic mirror 360 and an absorption filter 362 is inserted into the afocal observation optical system. As a result, the optical axis of the afocal observation optical system is shifted (center shift), and precise observation is not possible.

FIG. 20A and FIG. 20B describe the constitution of a center correction unit used in FIG. 19. In Japanese Unexamined Patent Application, First Publication No. H10-115781, as shown in FIG. 20A and FIG. 20B, a center correction unit for correcting optical axis shift is used, this unit having a constitution in which the surfaces of a plano-concave lens 368 and a plano-convex lens 370 are brought into mutual opposition, with a prescribed spacing maintained therebetween, and are held to enable mutual movement along the curvature of the concave and convex surfaces thereof, the unit being provided in the fluorescence cube 356 of FIG. 19.

In a constitution such as this, it is possible to correct the optical axis shift by adjusting the relative positional relationship between the plano-concave lens 368 and the plano-convex lens 370 of the fluorescence cube 356 in accordance with the amount of optical axis shift caused by the insertion of a mirror or a filter.

In the past, in analyzing a sample (object under measurement), analysis has been proposed of spectral analysis of the excitation light, fluorescent light, and Raman scattered light and the like occurring when an excitation laser beam illuminates the sample via a microscope.

Raman scattered light is an inelastic optical phenomenon occurring when a substance is illuminated by a single wavelength from a laser or the like, in which scattered light is slightly shifted (Raman shifted) toward the long-wavelength side and toward the short-wavelength side, relative to the wavelength of the illuminating single-wavelength light source. In Raman scattering, if the intensity of the illuminating light is taken to be 1, only a tiny intensity of approximately $10^{-14}$ is obtainable.

Because the spectrum of the Raman scattered light from Raman shifting is characteristic of the particular substance, it is possible to identify the chemical structure and physical condition of the substances included in the sample by detecting the Raman scattered light generated by the sample. It is possible to detect the Raman scattered light non-destructively, regardless of whether the sample is a solid, a liquid, or a gas.

In measuring the Raman scattered light in this manner, Raleigh scattered light is unwanted light that hinders the measurement of the characteristics of the sample.

If, however, the ratio of Raleigh scattered light and Raman scattered light is observed in the scattering cross-sectional plane, the ratio is substantially 10,000 to 1, the unwanted Raleigh scattered light being overwhelmingly large.

Given this, a proposal has been made of a spectroscopic unit capable of efficiently removing unwanted light components such Raleigh scattered light without losing the Raman scattered light component required for sample measurement.

Japanese Unexamined Patent Application, First Publication No. H8-261826 discloses a spectroscopic unit for the purpose of separating and removing with high efficiency reflected light and Raleigh scattered light from the Raman scattered light (signal light) that is very much weaker, and detecting only the signal light.

FIG. 30 is a drawing showing the constitution of a filter spectroscopic unit described in Japanese Unexamined Patent Application, First Publication No. H8-261826. In FIG. 30, the spectroscopic unit 601 is constituted by narrowband bandpass filters 611 to 614 and a mirror 615. After being formed into a parallel beam by a first optical system 602, the optical axis of the light radiated from a sample 607 is bent approximately 90° by a first mirror 603. This light beam is made by the first mirror 603 to strike the incident to the narrowband bandpass filters 611 to 614 at equal angles, the Raleigh light being removed by passage, and the Raman light being reflected and passed on. A second mirror 605 acts so as to return the spectrally dispersed light beam to the optical axis of the first optical system 602 and the first mirror 603. A second optical system 606 collects the light beam spectrally dispersed as noted above onto an entrance slit of the main spectroscope 617.

Raman scattering is an inelastic optical phenomenon occurring when a substance is illuminated by a single wavelength from a laser or the like, in which scattered light is slightly shifted toward the long-wavelength side and toward the short-wavelength side, relative to the wavelength of the illuminating single-wavelength light source. The spectrum of the Raman scattered light that is wavelength shifted (Raman shifted) is characteristic of the particular substance. By measuring the Raman scattering light spectrum, it is possible to specify what the substance is that was illuminated.

When light illuminates a metal nano-structure, surface plasmons, which are compressed and expanded waves of free electrons at the metal surface, are excited, the surface plasmons having the effect of enhancing the photoelectric field in the region thereof.

As a result, the Raman scattered light generated in the region surrounding the metal nano-structure is enhanced and can be measured. That is, when a substance exists in the area surrounding a nano-sized metal structure, when illumination is done by a single-wavelength light such as from a laser or the like, the substance generates enhanced Raman scattered light. Specifically, when a substance exists in the area surrounding a nano-sized metal structure, when illumination is done by a single-wavelength light such as from a laser or the like, the substance generates enhanced Raman scattered light. This enhanced Raman scattered light is known as SERS (surface-enhanced Raman scattering).

When light illuminates a metal nano-structure, there is the effect that surface plasmons, which are compressed and expanded waves of free electrons at the metal surface, are excited and there is the effect of the photoelectric field in the region thereof being enhanced in the surface plasmons. As a result, it is possible to enhance and measure the Raman scattered light generated in the area surrounding the metal nano-structure.

Because both the above-noted Raman scattering and SERS involve the measurement of Raman shift, the measuring apparatuses used therefor are basically the same, and although the present invention may be applied to the measurement of either Raman shift or SERS, it offers particularly good effectiveness when an apparatus having a constitution for measuring Raman shift is combined with a microscope.

Japanese Unexamined Patent Application, First Publication No. 2007-179002, for example, discloses a laser microscope as a microscope for use in combination with an apparatus constitution for measuring Raman shift of this type. FIG. 34 is a drawing of the constitution of the laser microscope disclosed in Japanese Unexamined Patent Application, First Publication No. 2007-179002, this constitution being one in which the light is scanned in a direction perpendicular to the optical axis.

In FIG. 34, an optical microscope 800 has a laser light source 810, a Y scanning device 813 that scans in the Y direction light a beam expanded by a beam expander 811, a lens 814, that refracts a light beam that has been deflected by the Y scanning device 813, a diaphragm 815 to which a light beam that is refracted by the lens 814 is incident, a lens 816 that refracts the light beam that passes through the diaphragm 815, an objective lens 821, an X scanning mirror 818 that scans the light beam in the X direction, lenses 819 and 820 that refract the light beam scanned by the X scanning mirror 818, a beam splitter 817 disposed in the light path from the Y scanning device 813 to a sample 822, and that splits the light beam incident to the sample 822 into light exiting an objective lens 821 side from the sample 822 that has changed to a different wavelength and the light beam that is incident to the sample 822 from the laser light source 810, a stage 823 on which the sample 822 is disposed, a lens 824 that refracts the light beam that passed through the beam splitter 817, a spectroscopic unit 831 that has an entrance slit 830 disposed along a direction corresponding to the Y direction and that spatially disperses the exiting light that passed through the entrance slit 830 in accordance with the wavelengths thereof, a detector 832 that detects the exiting light that is dispersed by the spectroscopic unit 831, a stage drive apparatus 840 that drives the stage 823, and a processor 850 that controls the various parts.

The Y scanning device 813 is constituted, for example, by an acousto-optic element or galvano mirror, and changes the exiting angle so as to deflect the incident light beam. By doing this, the position of incidence of the light beam on the sample 822 is changed along the Y direction. That is, the Y scanning device 813 scans the light beam in the Y direction.

The X scanning mirror 818 is constituted, for example, by a galvano mirror, and changes the angle of the reflecting surface so as to deflect the light beam. That is, because the angle of inclination of the reflecting surface of the X scanning mirror 818 with respect to the optical axis is changed, it is possible to change the exiting angle of the light beam. By doing this, it is possible to change the position of incidence of the light beam on the sample 822 and scan the light beam in the X direction.

The light beam is scanned in the Y direction at least one time during the imaging of one frame by the detector 832. That is, the scanning period of the Y scanning device 813 is made shorter than the exposure time, and scanning is done in Y direction one or more times during the exposure time of one frame of the detector 832. By doing this, it is possible to measure the spectrum in a linear region corresponding to the scanning range in one frame of the detector 832.

By scanning the overall scanning range of the Y scanning device 813 during the exposure time, the position of incidence of the light beam on the entrance slit 830 moves from one end to the other end of the Y scanning range during the exposure time. It is therefore possible to perform a spectral measurement with respect to the overall region corresponding to the aperture 830a over the sample 822, possible in one frame to image a linear region having a length corresponding to the aperture 830a of the entrance slit 830, and possible to measure the spectra of a plurality of points on the sample 822 with one exposure.

This reduces the number of charge transfers by the CCD of the detector 832 and the number of data transfers from the CCD, thereby shortening the measurement time, enabling measurement of the spectra at a plurality of points by the data transfer of one frame and, because it is not necessary to perform data transfer for each point individually, it is possible to shorten the measurement time.

In this case, because the pixels of the detector 832 are in rows from 'a' to 'n', it is possible to measure the spectra at n points of the sample 822 with one exposure, thereby enabling a shortening of the measurement time.

In this manner, by expanding the spectral information in a direction that is perpendicular to the Y direction of the detector 832 in which pixels are arranged in a two-dimensional array and acquiring spectral information in a straight-line region of the sample 822 all at one time, it is possible to perform a high-speed spectral measurement of a linear region.

When the imaging of one frame is completed, the X scanning mirror 818 makes a shift in the X direction position by the amount of one illumination region. Then, imaging of one frame is performed in the same manner, and the spectra of a linear region are measured. By repeating this, it is possible to measure the spectra over a two-dimensional region of the sample 822.

Because a laser microscope constituted as noted above scans the optical axis in the Y direction (with the Z axis within the within a plane perpendicular to the optical axis) and the X direction (with the Z axis within a plane perpendicular to the optical axis), high-speed spectral analysis is possible in the XY plane.

Japanese Unexamined Patent Application, First Publication No. 2007-179002 describes art of a laser microscope that can measure precisely in a short time. Japanese Unexamined Patent Application, First Publication No. 2004-317676 describes art of an optical system for correcting focal point shift in the Z direction.

In a conventional microscope spectrometer, because the Y scanning device 2 scans in the Y direction over a line on the sample during the time of transfer of frame data by the two-dimensional array light detector 8 in FIG. 11, the exposure (imaging) time with respect to the two-dimensional array light detector 8 becomes short.

Applying conventional art, although scanning can be repeated to perform imaging by the two-dimensional array light detector 8 in the case of spectral imaging of very weak light, high-speed spectrometry is difficulty with this method. Also, this method results in an integrated system, being not only large but also expensive.

Additionally, because when performing XY direction scanning of the focused point of the excitation light using a conventional microscope spectrometer the X scanning device 4 changes the angle of the reflective surface to shift the focused point in the X direction, there is a shift of the focal distance in the Z direction, resulting in the out-of-focus condition.

Although a corrective optical system such as described in Japanese Unexamined Patent Application, First Publication No. 2004-317676 may be provided for the purpose of correcting the out-of-focus image, this method results in an increase in the number of components and increase in the size and the cost of the apparatus.

Also, with a conventional microscope spectrometer, the Y direction device 2 and the X direction device 4 use, for example, light deflection by galvano mirrors using motors, if the rotational axes in the two directions are made to be at right angles to one another, the apparatus becomes large.

Also, with a conventional microscope spectrometer, the spectroscopic unit 7 has a polychrometer, which is a fixed optical system using an optical dispersion element such as a diffraction grating.

In this case, because the polychrometer disperses the incident light (imparting thereto prescribed angles) and light of a prescribed wavelength range is extracted, in order to make correction to a condition such as parallel light, which is easy to handle, a plurality of optical elements, such as mirrors, lenses or the like, are required. For this reason, the number of components increases, and the apparatus becomes large and expensive.

Also, with a conventional microscope spectrometer, if the spectroscopic unit 7 has a diffraction grating or the like, because of the wavelength dependency of the angle of light diffraction thereof (stated differently, because the relationship between the wavelength and the angle of diffraction is not linear), it is not possible to obtain uniformly spaced wavelength resolution. For this reason, because uniformly spaced wavelength resolution is not obtainable, when identifying the chemical structure and physical condition of substances included in the sample, precision analysis is not possible in some given wavelength region. Specifically, with a conventional microscope spectrometer, uniformly spaced waveform sampling is not possible. For this reason, if uniformly spaced wavelength sampling capability is not possible, precision analysis is not obtained in some given wavelength band.

Also, although, depending upon the chemical structure and physical condition of the substances included in the sample, there are cases in which it is necessary to analyze the intensity of transmitted light obtained in fine wavelength bands, if the spectroscopic unit 7 has a diffraction grating or the like, there are cases in which it is difficult to control the width of the wavelength passband (for example, in the case of a monochrometer), making precise high-speed analysis impossible.

An axis correction unit having a constitution such as shown in FIG. 20A and FIG. 20B "deflects" the intrinsic optical axis to incline it, and in an optical system such as one for microscopic observation while changing the angle of incidence of the light, a complex adjustment is required each time the angle is changed.

Also, in using an axis correction unit in an optical system that includes a variable bandpass filter of the angular modulation type, it is difficult to vary the relative positional relationship between the plano-concave lens 368 and the plano-convex lens 370 continuously.

Although the constitution of FIG. 30, by using a plurality of narrowband bandpass filters, suppresses the transmissivity in a narrow wavelength region, because the wavelength is fixed at the same wavelength as the light source, it is not possible to continuously change the center wavelength.

With the constitution of FIG. 34, in order to make a line scan of the focal point one time during the frame data transfer time of the two-dimensional array detector 832, the exposure (imaging) time with respect to the two-dimensional array detector 832 is short, and in the case of spectrally imaging very faint light, it is necessary to image by repeated scans and imaging by the two-dimensional array detector 832, the result being that high-speed spectroscopy is difficult. Also, with the constitution of FIG. 34, the apparatus becomes large and expensive.

Also, although the focal point is line scanned in the Y direction, by shifting this in the X direction and repeating to image in the XY plane, the focal distance shifts in the Z direction. The shift in the Z direction leads to the acquisition of an out-of-focus image. Although the correction thereof requires an additional optical system such as disclosed in Japanese Unexamined Patent Application, First Publication No. 2004-317676, such a corrective optical system is not desirable, because, for example, it increases the number of components, increases the size of the apparatus, and makes the apparatus expensive.

Also, although light deflection by galvano mirrors using motors is used, for example, as a means for focus spot scanning in the X direction and Y direction, if the rotational axes in the two directions are made to be at right angles to one another, the apparatus becomes large.

Although a polychrometer, which is a fixed optical system using a spectral dispersing element such as a diffraction grating can be envisioned as a method of spectral dispersion within the frame data transfer time of the two-dimensional array detector 832, because a light-dispersing element has the function of dispersing a spectrum to varying angles, in order to correct these angles to a condition of light such as parallel light, which is easy to handle, a plurality of optical elements, such as mirrors, lenses or the like, are required, this leading to an increase in the number of components, and the apparatus becomes large and expensive.

Also, because the relationship between the wavelength and the angle of diffraction of a diffraction grating is not linear, the light diffraction angle has dependency upon the wavelength, making it impossible to obtain uniformly spaced wavelength resolution over a wide wavelength region. Specifically, a uniformly spaced wavelength sampling capability with respect to a wide wavelength region cannot be obtained with a diffraction grating.

Additionally, because each focus spot is scanned, even for the same wavelength, it is not possible to make spectral dispersion at each focus spot for each spot at the same time, thereby making simultaneous spectral distribution difficult.

SUMMARY

The present invention implements a microscope spectrometer capable of high-speed spectral dispersion with a prescribed wavelength resolution spacing.

The microscope spectrometer in accordance with a preferred embodiment of the present invention may include, in a microscope spectrometer in which, when an excitation light from a light source illuminates a sample, a light emitted from the sample that enters a microscope is analyzed, a first optical means that forms the light emitted from the sample as a parallel beam, a first variable bandpass filter means having a variable wavelength passband that transmits incident light, which of the parallel beam of incident light, is light of a pre-established wavelength passband, a two-dimensional array light detection means that images the light in the wavelength passband, and a control means that controls the timing of the imaging by the two-dimensional array light detection means and, in accordance with the timing, changes the wavelength passband of the first variable bandpass filter means.

The control means may control the first variable bandpass filter means to sweep a pre-established plurality of wavelength passbands.

The control means may control the two-dimensional array light detection means so as to image the light at a pre-established time interval, and control the first variable wavelength bandpass filter means to change the wavelength passband by a pre-established wavelength band interval.

The present invention may also have a second variable bandpass filter means having a variable wavelength passband that transmits incident light which, of the light incident from the first variable bandpass filter means, is light of a pre-established wavelength passband, and the control means may vary the wavelength passband of the second variable bandpass filter means so that the wavelength passband of the first variable bandpass filter means and the wavelength passband of the second variable bandpass filter means overlap.

The present invention may also have a polarization means that polarizes the light that has passed through the first variable bandpass filter or the second variable bandpass filter to a pre-established polarization direction, and the control means may change the polarization direction of the polarization means.

The present invention may also have an optical axis adjustment means that corrects the position shift of the optical axis of the light in a two-dimensional plane.

The optical axes of the light source and the first optical means, the first variable bandpass filter means, and the second variable bandpass filter means may be a common optical axis.

The present invention provides an optical axis shift correction device capable of optical axis shift correction with a relatively simple constitution.

The optical axis shift correction device in accordance with a preferred embodiment of the present invention may be a device for correcting an optical axis shift, which corrects the shift of the optical axis caused by an optical filter provided in the optical system, having a corrective optical plate having a thickness and a refractive index that are equal to the thickness and the refractive index of the optical filter, and a rotational drive mechanism that drives so that the optical filter and the corrective optical plate rotate by equal angles of inclination in mutually different directions.

The rotational drive mechanism may rotationally drive the optical filter and the corrective optical plate using a common source of rotational drive.

The rotational drive mechanism may rotationally drive the optical filter and the corrective optical plate using separate individual sources of rotational drive.

The present invention provides a spectroscope capable of continuously changing the center wavelength with a relatively simple constitution.

The spectrometer in accordance with a preferred embodiment of the present invention may be made up of a first and a second filter group constituted by at least two variable bandpass filters, these filter groups being mounted so as to enable rotation so that the filter groups cross the optical axis at a desired rotational angles.

The filter groups may have at least two variable bandpass filters mounted to a rotatable filter support plate.

Each of the variable bandpass filters in the filter groups may be mounted so as to be independently rotatable.

The spectroscope in accordance with a preferred embodiment of the present invention may have a light source that illuminates a sample, a variable bandpass filter that selects a desired wavelength region of reflected light from the sample, a two-dimensional array detector onto which light that has passed through the variable bandpass filter is incident, and a controller that shifts the wavelength region of the variable bandpass filter, calculates the difference in the detected output at each element of the two-dimensional detector before and after the shift, and makes a spectral output.

The present invention provides a small, low-cost spectroscope that, with a relatively small number of components, is capable of high-speed spectroscopy with a high wavelength resolution in a two-dimensional (XY) plane, and a microscope using that spectroscope.

The microscope in accordance with a preferred embodiment of the present invention may have a light source that illuminates a sample, a variable bandpass filter that selects a desired wavelength region of reflected light from the sample, a two-dimensional array detector onto which light that has passed through the variable bandpass filter is incident, an image-forming optical system that forms an image of the light passing through the variable bandpass filter onto a light-receiving surface of the two-dimensional array detector, and a controller that shifts the wavelength region of the bandpass filter, calculates the difference in the detected output at each element of the two-dimensional array detector before and after the shift, and makes the difference a spectral output.

The image-forming optical system may be a confocal optical system.

BRIEF DESCRIPTION OF THE DRAWINGS

The above features and advantages of the present invention will be more apparent from the following description of certain preferred embodiments taken in conjunction with the accompanying drawings, in which.

DETAILED DESCRIPTION OF THE PREFERRED EMBODIMENTS

The present invention will be now described herein with reference to illustrative preferred embodiments. Those skilled in the art will recognize that many alternative preferred embodiments can be accomplished using the teaching of the present invention and that the present invention is not limited to the preferred embodiments illustrated herein for explanatory purposes.

The present invention relates to a microscope spectrometer that analyzes a multiply dispersed light over a wide wavelength range emitted from a sample and that is incident to the microscope. A first variable bandpass filter means having a variable wavelength passband that transmits scattered light that has been formed into a parallel beam by a first optical means transmits, of the incident light, light of a pre-established wavelength passband, a two-dimensional array detection means images the scattered light in the wavelength passband, and a control means controls the timing of the imaging by the two-dimensional array detection means and, in accordance with the timing, changes the wavelength passband of the first variable bandpass filter means, thereby enabling high-speed spectral dispersion in a region on a two-dimensional plane of the sample, with a pre-established wavelength resolution. Specifically, the present invention relates to a microscope spectrometer that enables high-speed wavelength sampling of a region on a two-dimensional plane of a sample with a pre-established spacing.

In the following, the microscope spectrometer of the present invention will be described, using the drawings.

First Preferred Embodiment

Figure 1:
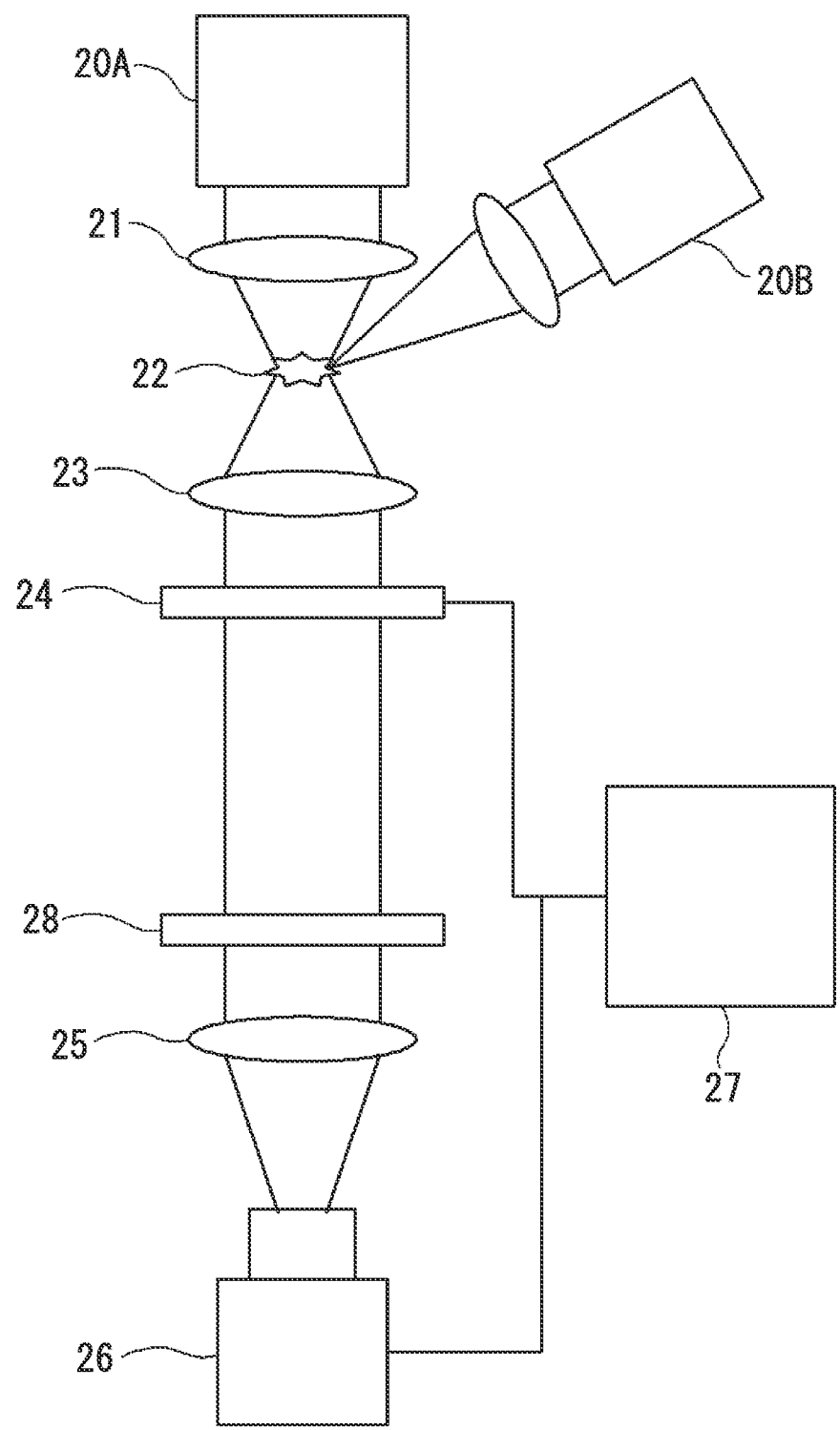
FIG. 1 is a constitution diagram illustrating a microscope spectrometer in accordance with a first preferred embodiment of the present invention.

FIG. 1 is a constitution diagram illustrating a microscope spectrometer in accordance with a first preferred embodiment of the present invention.

(Constitution)

In FIG. 1, the microscope spectrometer in accordance with the first preferred embodiment of the present invention has an incandescent light source that illuminates a sample 22 with excitation light, a single-wavelength light source such as a laser, a light source 20A such as a wideband light source, a light illumination lens means 21 constituted by a light-collecting lens or the like that collects the excitation light from the light source 20A, a sample 22, which is the object under measurement, which is illuminated by excitation light collected by the light illumination lens means 21 and which generates Raman scattered light and the like, a first optical means 23, which is a part of a microscope (not shown) and which is an objective lens or the like that forms the scattered into a parallel beam, a first variable bandpass filter means 24 of the light interference type or incident light angle tuned type having a variable wavelength passband that transmits incident light, and that, of the parallel beam of scattered light incident from the first optical means 23, transmits light of a pre-established wavelength region, an image-forming optical means 25, which is a light-collecting lens that collects light that is incident from the first variable bandpass filter means 24, a two-dimensional array light detection means 26, which is a CMOS (complementary metal oxide semiconductor) or CCD (charge-coupled device) image sensor or the like that images the scattered light from the first variable bandpass filter means 24 that was collected by the image-forming optical means 25, and a control means 27 that controls the timing of the imaging by the two-dimensional array detection means 26 and changes the wavelength passband of the variable bandpass filter 24 in accordance with the timing.

In this case, the variable bandpass filter means 24 and the two-dimensional array light detection means 26 are electrically connected to the control means 27, and the wavelength region (wavelength passband) subjected to spectral dispersion and imaging timing thereof are controlled by control signals from the control means 27.

When a dark-field image is obtained, the microscope spectrometer of the present invention may have an optical system in which the light illumination lens means 21 is a condenser lens or the like.

The microscope spectrometer of the present invention may have a light source 20B that is, for example, a laser light source that illumines the sample with a laser light for the purpose of excitation thereof, for example, one that illuminates the sample 22 at a pre-established angle with respect to the optical axis of the light source 20A.

The optical axis of the light source 20B may be disposed so that is coincides with the optical axis of the light illumination lens means 21, in which case the light illumination lens means 21 has a condenser lens. In this case, the microscope (not shown) constituted by a first optical means 23 such as an objective lens or the like operates as a dark-field microscope.

Additionally, the microscope spectrometer of the present invention may have a notch filter 28 disposed between the first variable bandpass filter means 24 and the two-dimensional array light detection means 26, which attenuates (cuts, blocks) the light intensity of a specific wavelength region of the light transmitted from the first variable bandpass filter 24.

The light source 20A and light illumination lens means 21, the first optical means 23, the first variable bandpass filter 24, the notch filter 28, the image-forming optical means 25, and the two-dimensional array light detection means 26, as shown in FIG. 1, are disposed so as to have a common optical axis (so that their optical axes coincide) or, stated differently, are disposed in an unbranched straight line. By disposal in this manner, the overall microscope spectrometer can be made compact.

(Detailed Description of the Main Constituent Elements)

The first variable bandpass filter means 24 has a variable wavelength passband that transmits incident light and, of the parallel beam of scattered light incident from the first optical means 23, transmits light of a pre-established wavelength passband.

Specifically, the first variable bandpass filter means 24 is constituted to include a filter unit, the filter characteristics of which respect to transmitted light change in accordance with the angle of incidence to a film surface, and a rotational stage that changes the angle of the filter.

Figure 2:
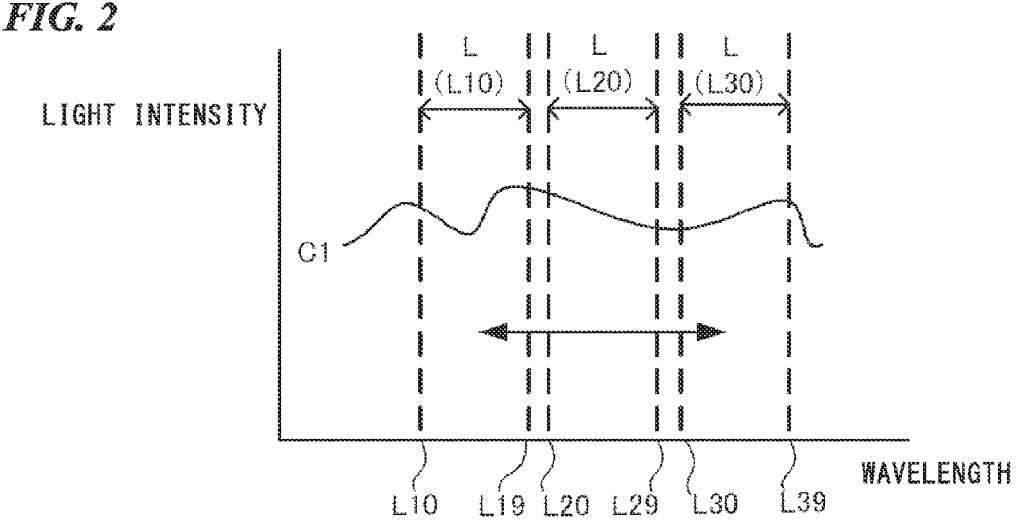
FIG. 2 is a drawing describing the wavelength passband in which the first variable bandpass filter means of FIG. 1 transmits scattered light.

FIG. 2 is a drawing describing the wavelength passband in which the first variable bandpass filter means of FIG. 1 transmits scattered light.

In FIG. 2, the first variable bandpass filter means 24 has, for example, wavelength regions of a prescribed width (interval) L, in which light can pass. The first variable bandpass filter means 24 varies the angle of incidence of light to the filter unit to control the wavelength passband.

For example, as shown in FIG. 2, the first variable bandpass filter means 24 has a wavelength passband that can be changed to three passbands, a band from L10 to L19 (hereinafter referred to as L10), a band from L20 to L29 (hereinafter referred to as L20), and a band from L30 to L39 (hereinafter referred to as L30). Scattered light of the scattered light C1 (an example of a spectrum including in the light from the sample) from the first optical means 23 is passed through one of the bands L10, L20, and L30.

The control means 27 controls the first variable bandpass filter means 24 and the two-dimensional array light detection means 26 so as to image the prescribed wavelength passbands with a prescribed timing.

Stated differently, the control means 27 controls the first variable bandpass filter means 24 and the two-dimensional array light detection means 26 so as to perform a tuning operation.

The control means 27 controls the two-dimensional array light detection means 26 to image the scattered light with a pre-established time interval (for example, a uniform time interval), and controls the first variable bandpass filter means 24 to change the wavelength passband with a wavelength region having a pre-established interval (for example, a uniform interval or a user-desired interval).

Figure 3:
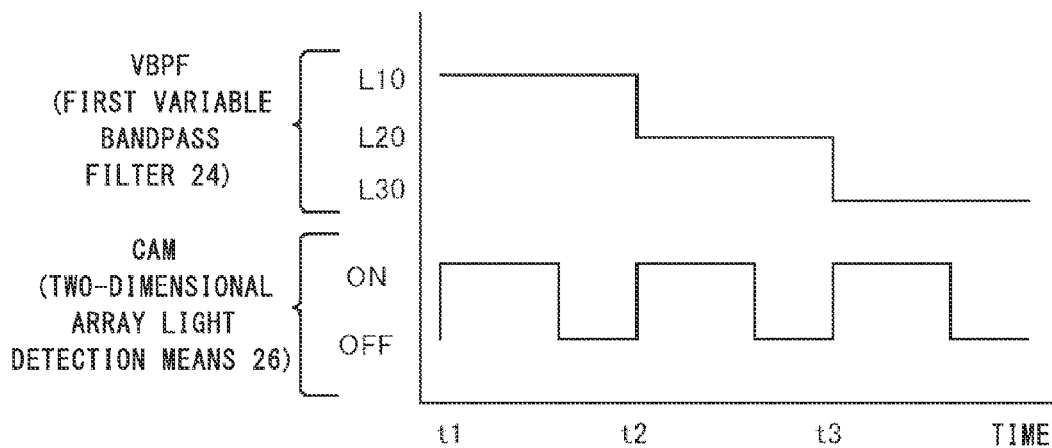
FIG. 3 is a timing chart regarding the operational timing of the variable bandpass filter and a two-dimensional array light detection means.

FIG. 3 is a timing chart regarding the operational timing of the variable bandpass filter and a two-dimensional array light detection means when the controller of FIG. 1 controls the variable bandpass filter means and two-dimensional array light detection means so as to image light in a prescribed wavelength passband.

In FIG. 3, the upper VBPF (variable bandpass filter) shows the changes in state of the variable bandpass filter means 24 to the wavelength passbands L10, L20, and L30 that pass light. The lower CAM (two-dimensional array light detection means) shows the timing of the imaging of the scattered light by the two-dimensional array light detection means 26.

In FIG. 3, the control 27 controls the imaging timing (timing of switching on) of the two-dimensional array light detection means 26 that is stored beforehand in a storage means (not shown) and a controls the variable bandpass filter means 24 in accordance with the imaging interval to change the wavelength passband to L10, L20, and L30.

Specifically, at the imaging times t1, t2, and t3 of the two-dimensional array detection means 26, the wavelength passband of the variable bandpass filter means 24 is made L10, L20, and L30.

After the imaging operation of the two-dimensional array light detection means 26 is completed, the control means 27 transitions the wavelength passband of the variable bandpass filter means 24 between L10, L20, and L30.

The control means 27 may be a CPU (central processing unit) or the like that controls the operation of the various means. Specifically, the control means 27 launches an operating system or the like stored in a storage means (not shown) and performs overall control of the spectrometer by reading and executing in the operating system a program stored in the storage means, controlling the variable bandpass filter means 24 with a pre-established timing or imaging interval, and changing the wavelength passband and imaging the light passed through the two-dimensional array light detection means 26.

(Operation and Effect)

The microscope spectrometer of the present invention having the above-described constitution does the following operations.

(1-1) The control means 27 controls the wavelength passband of the first variable bandpass filter means 24 with a pre-established timing to L10.

(1-2) The light source 20A illuminates the sample 22 with excitation light.

(1-3) The light illumination lens means 21 collects the excitation light and illuminates the sample 22.

(1-4) At the sample 22, Raman scattered light is generated by the illuminating excitation light.

(1-5) The first optical means 23 changes the scattered light generated by the sample 22 to a parallel beam.

(1-6) The first variable bandpass filter means 24, of the scattered light in the parallel beam from the first optical means 23, transmits light in the wavelength passband L10.

(1-7) The image-forming optical means 25 collects the incident light from the first variable bandpass filter means 24.

(1-8) The two-dimensional array light detection means 26 images the scattered light from the first variable bandpass filter means 24 that was collected by the image-forming optical means 25.

(1-9) The two-dimensional array light detection means 26 ends imaging when a pre-established imaging time has elapsed.

(1-10) The control means 27 controls the wavelength passband of the first variable bandpass filter means 24 to L20 with a pre-established timing, and controls the two-dimensional array light detection means 26 to image the light passed in L20.

(1-11) The two-dimensional array light detection means 26 ends imaging when a pre-established imaging time has elapsed.

(1-12) The control means 27 controls the wavelength passband of the first variable bandpass filter means 24 to L30 with a pre-established timing, and controls the two-dimensional array light detection means 26 to image the light passed in L30.

As a result, the microscope spectrometer of the present invention is effective with regard to the point that a first variable bandpass filter means that has a variable passband that transmits scattered light that is made into a parallel beam by the first optical means transmits light of the incident scattered light that is in a pre-established wavelength passband, the two-dimensional array light detection means images the scattered light in the wavelength passband, and a control means controls the timing of imaging by the two-dimensional array light detection means, changing the wavelength passband of the variable bandpass filter means, so as to enable high-speed spectral dispersion over a two-dimensional region of a sample, with a pre-established wavelength resolution (for example, a uniform interval, or an arbitrary user-desired interval).

Additionally, because there is no Z-direction focal point change in the optical system used in the constitution, the effect of obtaining a sharp spectral image that is not out-of-focus is also achieved.

Also, by the control means 27 controlling to perform a tuning operation of the two-dimensional array light detection means 26 and the variable bandpass filter 24, the effect is achieved of enabling a spectral image over a two-dimensional region at one time.

By adopting the above-described constitution, the microscope spectrometer of the present invention enables implementation of a compact, low-cost microscope spectrometer that, with a small number of components, is capable of high-speed acquisition of sharp images that are not out-of-focus, with a pre-established wavelength resolution, even in the case of weak light. The microscope spectrometer of the present invention enables the high-speed acquisition of sharp images that are not out-of-focus, using wavelength sampling with a pre-established interval, even in the case of weak light.

Although, as a convenience in description, the microscope spectrometer of the present invention was describe in the present preferred embodiment as having wavelength passbands of the variable bandpass filter 24 of L10, L20, and L30, the variable bandpass filter 24 may pass scattered light in a larger number of wavelength passbands.

In this case, if the control means controls the variable bandpass filter means to sweep the wavelength passbands, the effect of enabling spectral dispersion of a continuous spectral band is achieved.

Also, because the interval of the wavelength passband of the variable bandpass filter 24 is the wavelength resolution, the microscope spectrometer of the present invention can, by having a large number of wavelength passbands with a narrow band interval, achieve a high time-division wavelength resolution. Specifically, because the interval of the wavelength passbands of the variable bandpass filter 24 is the wavelength sampling capability, the microscope spectrometer of the present invention can achieve a high time-division wavelength sampling capability by having a large number of wavelength passbands with a narrow band interval.

Although, as a convenience in description, the microscope spectrometer of the present invention was described in the present preferred embodiment in FIG. 2 with the variable bandpass filter 24 changing the wavelength passband from L10 to L20 and then L30 in a step-wise (discrete) manner, the change of the wavelength passband from L10 to L30 may be made continuously or along a curve. This operation will be described using FIG. 4.

Figure 4:
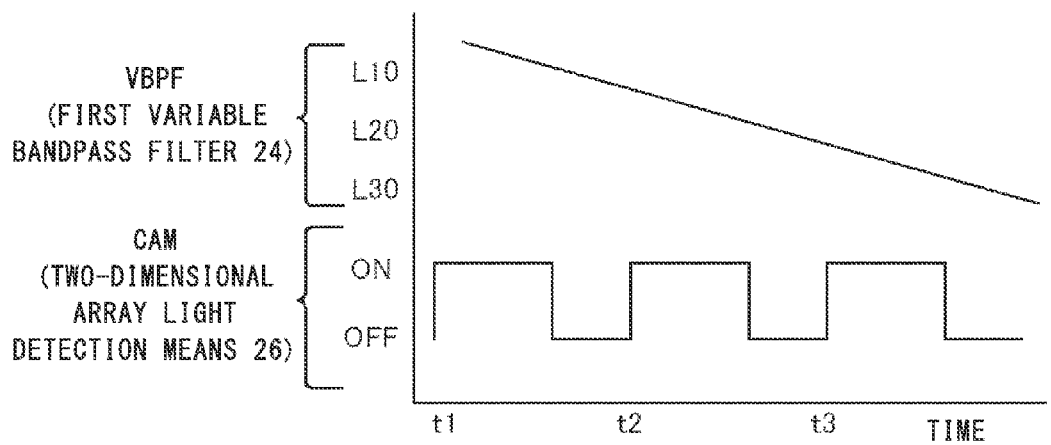
FIG. 4 is another drawing describing the operational timing of the variable bandpass filter means and the two-dimensional array light detection means.

FIG. 4 is another drawing describing the operational timing of the variable bandpass filter means and the two-dimensional array light detection means.

In FIG. 4, the control means 27 changes the angle of filter unit of the first variable bandpass filter means 24 by a prescribed angle at a time, so as to change the wavelength passband continuously from L10 to L30.

As a result, in the microscope spectrometer of the present invention, the control means, by continuously changing the wavelength passband by changing the filter unit of the first variable bandpass filter means by a prescribed angle at a time, it is possible to achieve spectral dispersion of a continuous spectral band (this being effective because of the ability to obtain a high time-division wavelength resolution). Specifically, the effect is that of achieving a high time-division wavelength sampling capability.

Also, in the microscope spectrometer of the present invention, the control means 27 may change the wavelength passband continuously from L10 to L30 while changing the width of the overlapping passband.

For example, in a range in which it analysis of a strong intensity of transmitted light obtained with a fine wavelength region is necessary, the control means 27 controls the first variable bandpass filter means to make the width (L) of the wavelength passband extremely narrow, and in a range in which high-intensity analysis of transmitted light is not particularly necessary, it controls to make the overlapping passband wide.

For this reason, the microscope spectrometer of the present invention is effective with regard to the point of being able to perform spectral dispersion of a continuous wavelength region for a desired range, and also being able achieve a higher time-division wavelength resolution and higher overall high speed than was conventionally possible. The microscope spectrometer of the present invention is also effective with regard to the point of achieving a higher time-division wavelength sampling capability than was conventionally possible.

Second Preferred Embodiment

By installing one or two or more additional variable bandpass filters between the first variable bandpass filter and the image-forming optical means (or notch filter) and tuning the plurality of variable bandpass filters, the microscope spectrometer of the present invention may perform spectral dispersion with a high optical wavelength resolution with respect to a partially overlapping wavelength passband.

Figure 5:
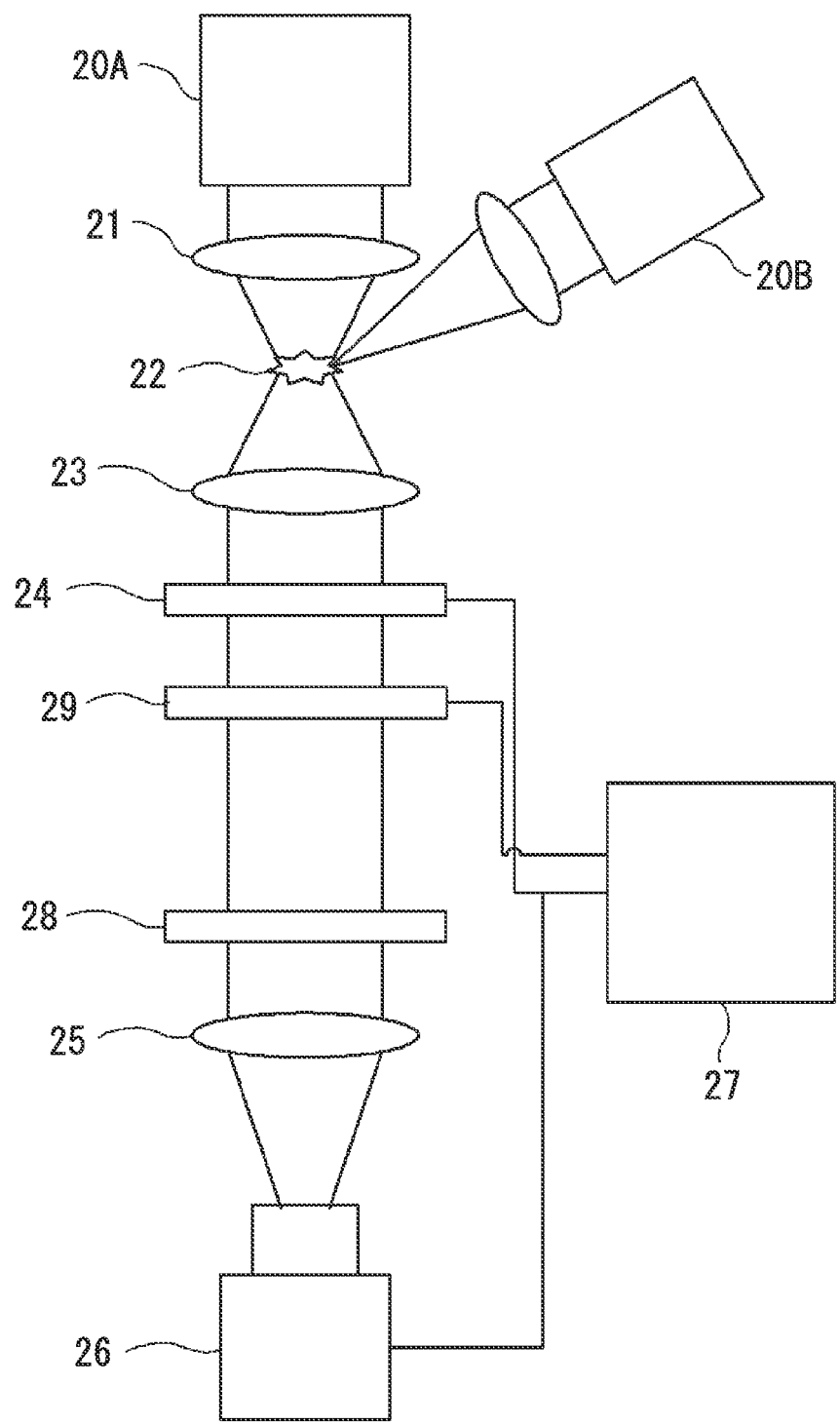
FIG. 5 is a constitution diagram illustrating a microscope spectrometer in accordance with a second preferred embodiment of the present invention.

FIG. 5 is a constitution diagram illustrating a microscope spectrometer in accordance with a second preferred embodiment of the present invention. Parts that are the same as in FIG. 1 are assigned the same reference numerals, and the descriptions thereof are arbitrarily omitted.

A main point of difference with respect to FIG. 1 is the provision of a second variable bandpass filter means that has a variable wavelength passband that transmits incident light, and that transmits, of the incident light from the first variable bandpass filter means, light in a pre-established wavelength passband. Also, the control means changes the wavelength passband of the second variable bandpass filter means so as to cause overlapping between the wavelength passband of the first variable bandpass filter means and the wavelength passband of the second variable bandpass filter means.

In FIG. 5, the microscope spectrometer of the present invention has a second variable bandpass filter means 29, of the light interference type or light incidence angle tuned type, installed between the first variable bandpass filter means 24 and the image-forming optical means 25 (or a notch filter 28), which has a variable wavelength passband that transmits incident light.

The second variable bandpass filter means 29 changes the angle of incidence of light to the filter unit and controls the wavelength passband while maintaining the width (for example L) of the passable wavelengths.

In this case, the second variable bandpass filter 29 has a passable wavelength width L' that differs from, or a passable wavelength width L that is substantially the same as, that of the first variable bandpass filter 24.

The second variable bandpass filter 29 is electrically connected to the control means 27 and the wavelength region that is spectrally dispersed (wavelength passband) is controlled based on a control signal from the control means 27.

If the second variable bandpass filter 29 has a passable wavelength width of L that is substantially the same as that of the first variable bandpass filter 24, the control means 27 performs control thereof so that the wavelength passbands differ.

Figure 6:
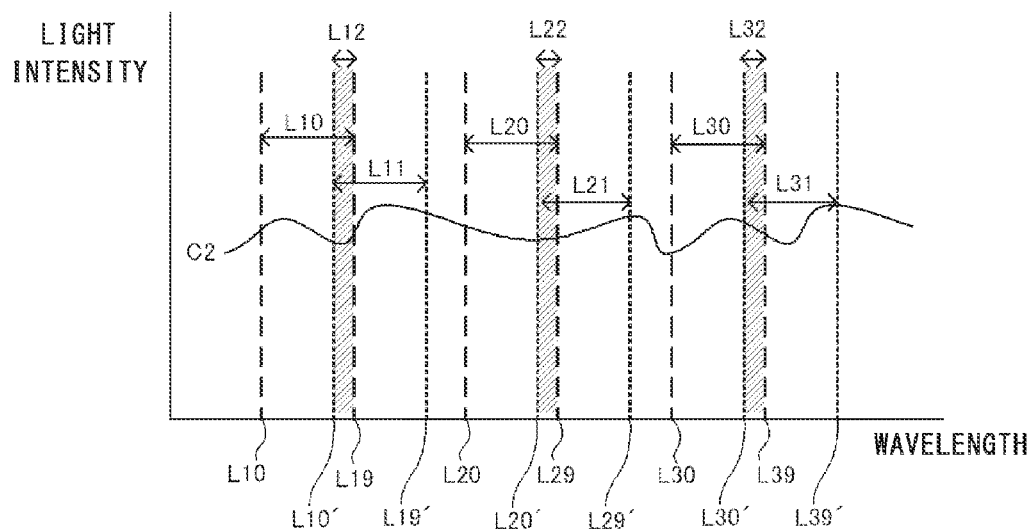
FIG. 6 is a drawing describing the wavelength passbands in which the first variable bandpass filter means and the second variable bandpass filter means of FIG. 5 pass scattered light.

FIG. 6 is a drawing describing the wavelength passbands in which the first variable bandpass filter means and the second variable bandpass filter means of FIG. 5 pass scattered light.

In FIG. 6, the first variable bandpass filter means 24 and the second variable bandpass filter means 29 have substantially the same wavelength region having a width L in which light can pass.

The first variable bandpass filter means 24 and the second variable bandpass filter means 29 vary the angle of incidence of light to the filter unit to control the wavelength passband while maintaining the width L of passable wavelengths.

In FIG. 6, the wavelength passband of the first variable bandpass filter means 24 has a wavelength passband that can be changed to the three passbands L10, L20, and L30.

The second variable bandpass filter means 29 has a wavelength passband that can be changed to three passbands, the band from L10' to L19' (hereinafter referred to as L11), the band from L20' to L29' (hereinafter referred to as L21), and the band from L30' to L39' (hereinafter referred to as L31), with overlapping between the wavelength passbands L10 and L11, L20 and L21, and L30 and L31.

In FIG. 6, the overlapping part between L10 and L11 is expressed as L12, the overlapping part between L20 and L21 is expressed as L22, and the overlapping part between L30 and L31 is expressed as L32.

In the following, the partial or total overlapping part between the wavelength passbands of the first variable bandpass filter means 24 and the second variable bandpass filter means 29 will be referred to as the overlapping passband.

The control means 27 controls the imaging timing (timing of switching on) of the two-directional array light detection means 26 that is pre-established and stored in a storage means (not shown) and controls the first variable bandpass filter means 24 in accordance with the timing to change the wavelength passband to L10, L20, and L30, and also controls the second variable bandpass filter means 29 to change the wavelength passband to L11, L21, and L31.

Figure 7:
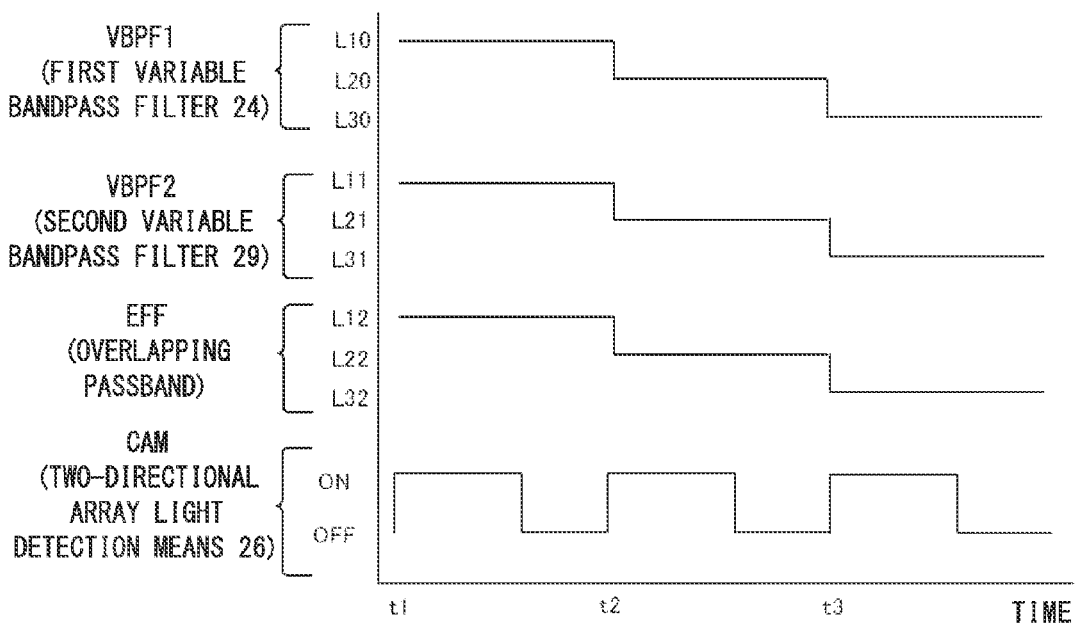
FIG. 7 is a timing chart regarding the operational timing of the first and second variable bandpass filter means and the two-directional array light detection means.

FIG. 7 is a timing chart regarding the operational timing of the first and second variable bandpass filter means and the two-directional array light detection means when the controller of FIG. 1 controls the first and second variable bandpass filter means so as to image light in a prescribed wavelength passband.

In FIG. 7, VBPF1 (first variable bandpass filter) shows the changes of state of the variable bandpass filter 24 to the wavelength passbands L10, L20, and L30 that pass light. VBPF2 (second variable bandpass filter) shows the changes of state of the variable bandpass filter 29 to the wavelength passbands L11, L21, and L31 that pass light.

EFF (overlapping passband) shows the changes of state of the overlapping passband to L12, L22, and L32.

CAM (two-directional array light detection means) shows the timing of imaging by the two-directional array light detection means 26, which exposes and images in the on state.

In FIG. 7, with the pre-established imaging timings (timing of switching on) of t1, t2, and t3 of the two-directional array light detection means 26 stored in the storage means, and with the wavelength passbands of the first variable bandpass filter means 24 as L10, L20, and L30 in accordance with the imaging interval, the control means 27 makes the wavelength passbands of the second variable bandpass filter means 29 as L11, L21, and L31.

Stated differently, the overlapping passbands become L12, L22, and L32 at the times t1, t2, and t3 of the imaging by the two-directional array light detection means 26.

In this case, the wavelength widths of the wavelength regions L12, L22, and L32 may be made a given width, or alternatively may be different.

(Operation and Effect)

The microscope spectrometer of the present invention having the above-described constitution does the following operations.

(2-1) With a pre-established timing, the control means 27 controls the wavelength passband of the first variable bandpass filter means 24 to L10, and controls the wavelength passband of the second variable bandpass filter means 29 to L11.

(2-2) The light source 20A illuminates toward the sample 22 with excitation light.

(2-3) The excitation light is illuminated onto the sample 22 by the light illumination lens means 21.

(2-4) At the sample 22, Raman scattered light is generated by the illuminating excitation light.

(2-5) The first optical means 23 changes the scattered light generated by the sample 22 to a parallel beam.

(2-6) The first variable bandpass filter means 24, of the scattered light in the parallel beam incident from the first optical means 23, transmits light in the wavelength passband L10.

(2-7) The second variable bandpass filter means 29, of the scattered light in the parallel beam incident from the first variable bandpass filter means 24, transmits light in the wavelength passband L11. That is, scattered light in L12, which is the overlapping range between L10 and L11, is passed.

(2-8) The image-forming means 25 collects the incident light from the second variable bandpass filter means 29.

(2-9) The two-directional array light detection means 26 images the scattered light in the wavelength region L12 from the first variable bandpass filter means 24 that was collected by the image-forming optical means 25.

(2-10) The two-directional array light detection means 26 ends imaging when a pre-established imaging time has elapsed.

(2-11) With a pre-established timing, the control means 27 controls the wavelength passband of the first variable bandpass filter means 24 to L20, controls the wavelength passband of the second variable bandpass filter means 29 to L21, and controls the two-directional array light detection means 26 to image the light passed in L22.

(2-12) The two-directional array light detection means 26 ends imaging when a pre-established imaging time has elapsed.

(2-13) With a pre-established timing, the control means 27 controls the wavelength passband of the first variable bandpass filter means 24 to L30, controls the wavelength passband of the second variable bandpass filter means 29 to L31, and controls the two-directional array light detection means 26 to image the light passed in L32.

As a result, the microscope spectrometer of the present invention, by tuning two variable bandpass filters, can transmit the scattered light over the entire (or part of the) prescribed wavelength region for each overlapping passband, thereby obtaining a higher time-division wavelength resolution. The microscope spectrometer of the present invention can obtain a higher time-division wavelength sampling capability.

The narrower is the range of the overlapping passbands (the smaller is the overlapping between the wavelength passbands of the first and second variable bandpass filter means), the higher is the time-division wavelength resolution that can be obtained. The narrower is the range of the overlapping passband, the higher is the optical wavelength resolution that can be obtained.

Given this, the microscope spectrometer of the present invention has a second variable bandpass filter means that has a variable wavelength passband that transmits incident light from the first variable bandpass filter means in a pre-established wavelength passband, and the control means changing the wavelength passband of the second variable bandpass filter means and causing overlapping between the wavelength passbands of the first variable bandpass filter means and the second variable bandpass filter means to tune the plurality of variable bandpass filters, so as to be able to perform a high-speed spectral analysis with a high optical wavelength resolution, wherein lies the effectiveness of the present invention.

Additionally, the fact that there is no change in the focus point in the Z-axis direction in the optical system constitution that is used is effective obtaining a clear image that is not out-of-focus is achieved.

By adopting the above-described constitution, the microscope spectrometer of the present invention enables implementation of a compact, low-cost microscope spectrometer that, with a small number of components, is capable of high-speed acquisition of sharp images that are not out-of-focus, with a wavelength resolution having a pre-established spacing, even in the case of weak light.

Although, as a convenience in description, in FIG. 7, the microscope spectrometer of the present invention was described in the present preferred embodiment as changing the wavelength passbands of the variable bandpass filters 24 and 29 from L10 to L20 to L30, and from L11 to L21 to L30 in a step-wise (discrete) manner, the change from L10 up to L30 and from L11 up to L31 may be done continuously or along a curve, so that the scattered light is transmitted for each overlapping passband over the entire (or a part of the) prescribed wavelength region.

Specifically, the control means 27 changes the filter unit of the first variable bandpass filter means 24 by a prescribed angle at a time to change the wavelength passband continuously from L10 up to L30, so that the bandwidth of the overlapping passband is held constant. In step with this, the control means 27 changes the filter unit of the second variable bandpass filter means 29 by a prescribed angle at a time to change the wavelength passband continuously from L11 to L31, so that the bandwidth of the overlapping passband is held constant. This is described below using FIG. 8.

Figure 8:
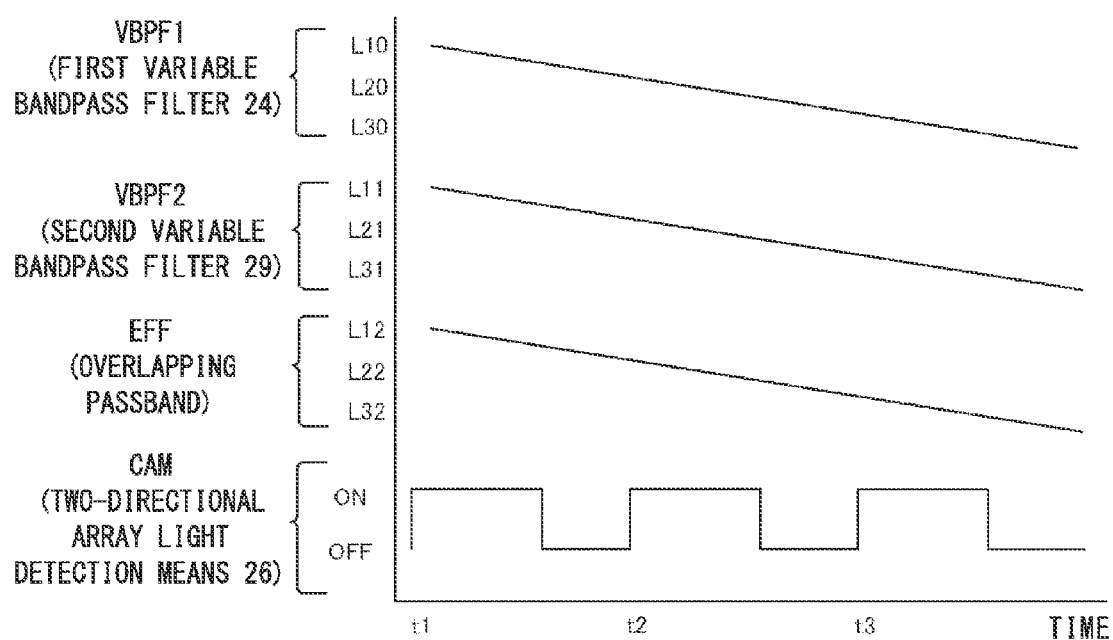
FIG. 8 is another timing chart regarding the operational timing of the first and second variable bandpass filter means and the two-directional array light detection means.

FIG. 8 is another timing chart regarding the operational timing of the first and second variable bandpass filter means and the two-directional array light detection means.

In FIG. 8, the filter units of the first variable bandpass filter means 24 and the second variable bandpass filter means 29 are changed by a prescribed angle at a time to change the wavelength passbands from L10 up to L30 between L11 and L31 by the control means 27. For this reason, the overlapping passband changes continuously from L12 to L32.

In the first variable bandpass filter 24 and the second variable bandpass filter means 29, the narrower is the range of overlapping passbands (the smaller is the overlapping between the wavelength passbands of the first and the second variable bandpass filter means), the higher is the time-division wavelength resolution that can be obtained, and the higher is the optical wavelength resolution that can be obtained.

Given this, in the microscope spectrometer of the present invention, the control means 27 changes the filter unit of the first variable bandpass filter means 24 by a prescribed angle at a time to change the wavelength passband continuously from L10 up until L30, making it possible to perform spectral dispersion over a continuous wavelength region, and to obtain a higher time-division wavelength resolution that conventionally possible, wherein lies the effectiveness of the present invention. The microscope spectrometer of the present invention is effective in obtaining a higher time-division wavelength sampling capability than conventionally possible.

Also, in the microscope spectrometer of the present invention, the control means 27 may change the wavelength passband continuously from L10 up to L30 while changing the width of the overlapping passband.

For example, in a range in which analysis of the intensity of transmitted light obtained with a fine wavelength region is necessary, the control means 27 controls the first and second variable bandpass filter means to make the width of the overlapping passband extremely narrow, and in a range in which intensity analysis of transmitted light is not particularly necessary, it controls to make the overlapping passband wide.

For this reason, the microscope spectrometer of the present invention is effective with regard to the point of being able to perform spectral dispersion of a continuous wavelength region for a desired range, and also being able achieve a higher time-division wavelength resolution and higher overall high speed than conventionally possible. The microscope spectrometer of the present invention is also effective with regard to the point of achieving a higher time-division wavelength sampling capability than conventionally possible.

Third Preferred Embodiment

In the microscope spectrometer of the present invention, a polarizing filter may be installed between the variable bandpass filter and the image-forming optical means (or the notch filter 28), so as to polarize the scattered light transmitted through the variable bandpass filter in a pre-established polarization direction.

Figure 9:
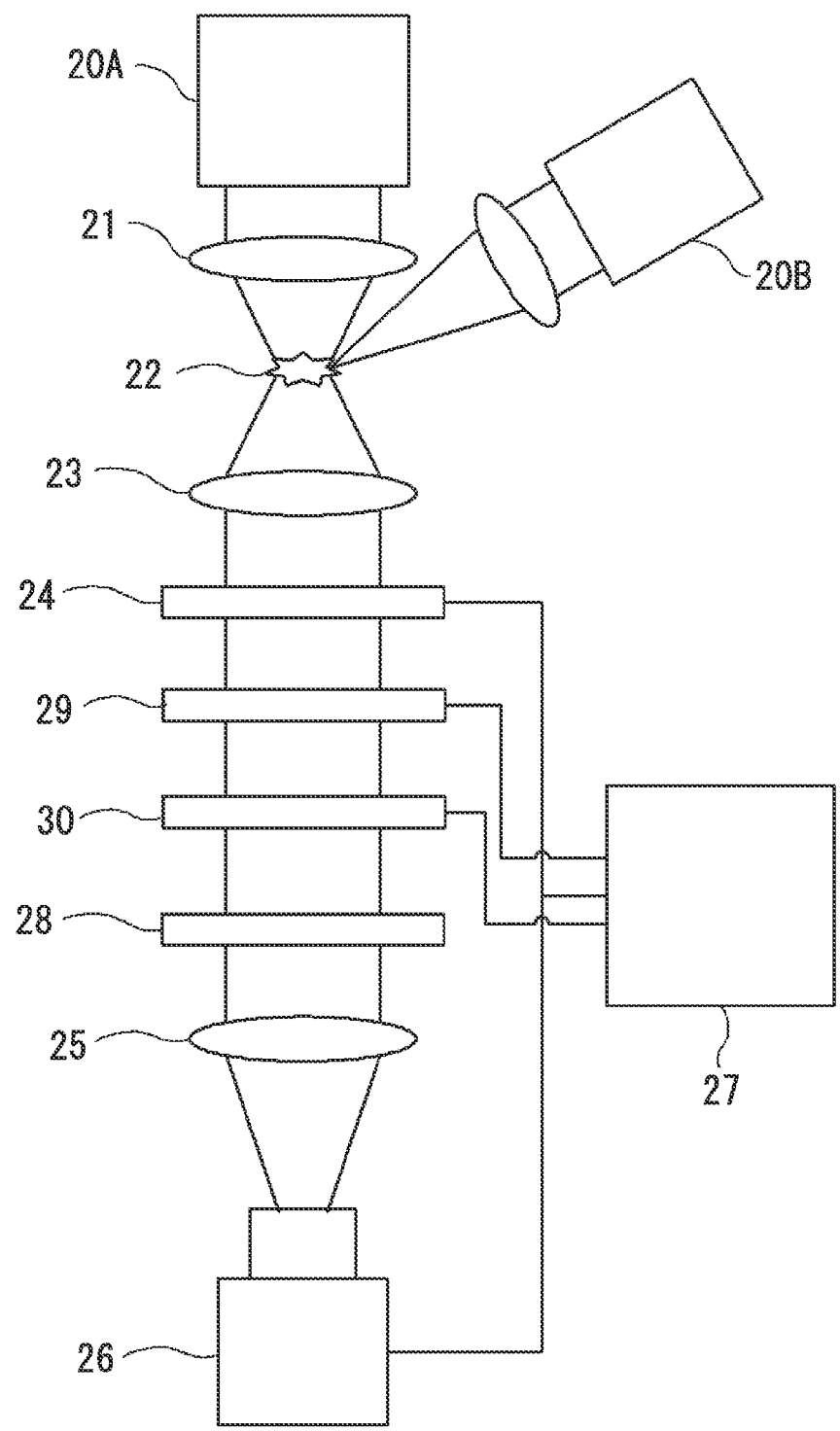
FIG. 9 is a constitution diagram illustrating a microscope spectrometer in accordance with a third preferred embodiment of the present invention.

FIG. 9 is a constitution diagram illustrating a microscope spectrometer in accordance with a third preferred embodiment of the present invention. Parts that are the same as in FIG. 3 are assigned the same reference numerals, and the descriptions thereof are arbitrarily omitted.

Main points of difference with respect to FIG. 3 are the provision of a polarization means that polarizes scattered light transmitted through the second variable bandpass filter 29 to a pre-established polarization direction, and the variable control of the polarization direction of the polarization means by the control means 27.

In FIG. 9, the microscope spectrometer of the present invention has a polarization means 30 that is a ½-wavelength, ¼-wavelength plate or the like, installed between the second variable bandpass filter 29 and the image-forming means 25 (or the notch filter 28), which polarizes the scattered light transmitted through the second variable bandpass filter to a pre-established polarization direction.

The polarization mean 30 converts the incident scattered light to circularly polarized light, linearly polarized light, or elliptically polarized light, which exits therefrom. The polarization means 30 is electrically connected to the control means 27, and a control signal from the control means 27 controls the polarization direction thereof.

As a result, by the microscope spectrometer of the present invention is effective with respect to the point of enabling spectral dispersion with polarization dependency by having a polarization means that polarizes scattered light that has passed through the second variable bandpass filter to a pre-established polarization angle.

Fourth Preferred Embodiment

The microscope spectrometer of the present invention may have, between the first optical means 23 and the first variable bandpass filter 24, an optical axis adjustment means for adjusting the optical axis, so as to correct a position offset occurring in the XY direction in a plane perpendicular to the optical axis of the incident scattered light from the first optical means.

Figure 10:
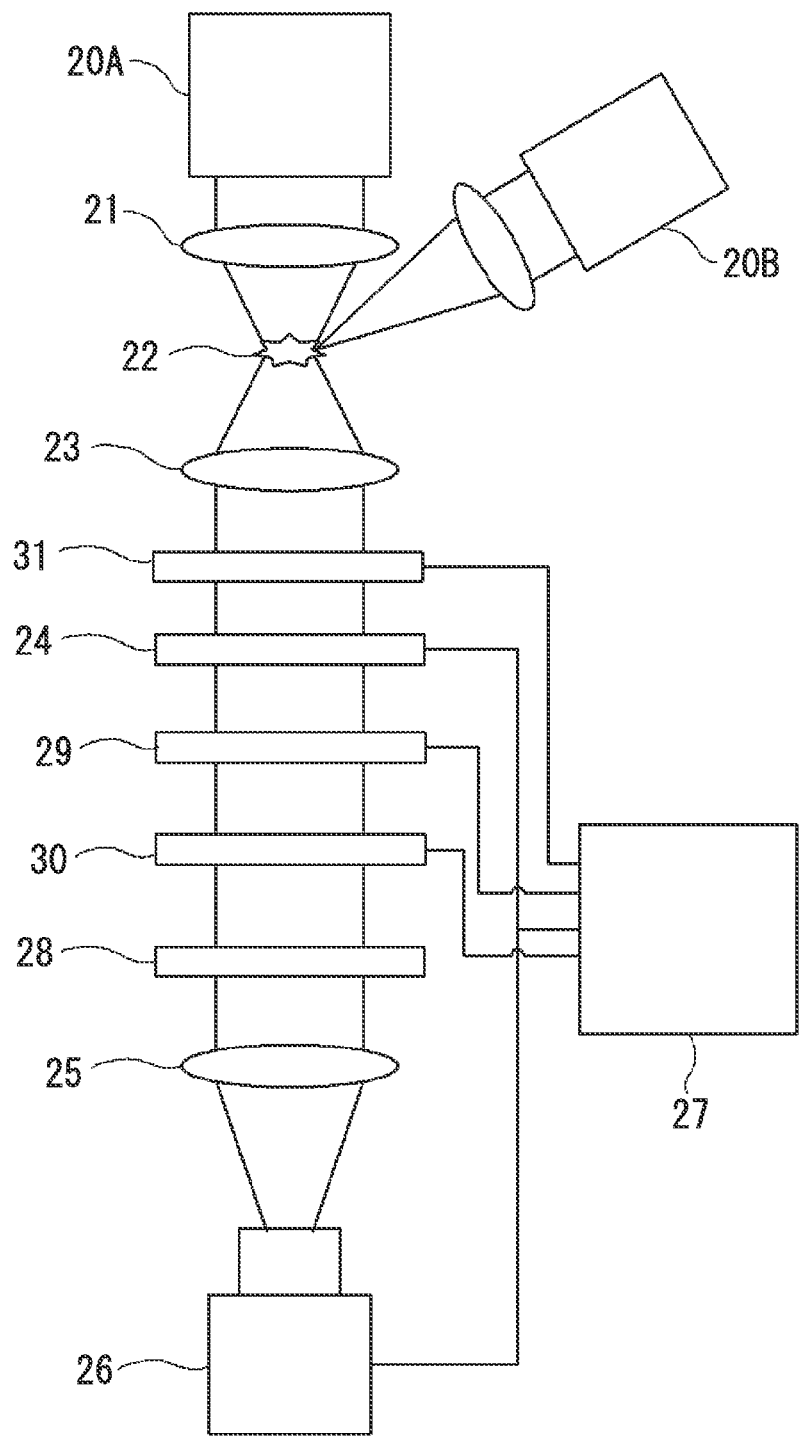
FIG. 10 is a constitution diagram illustrating a microscope spectrometer in accordance with a fourth preferred embodiment of the present invention.
Figure 11:
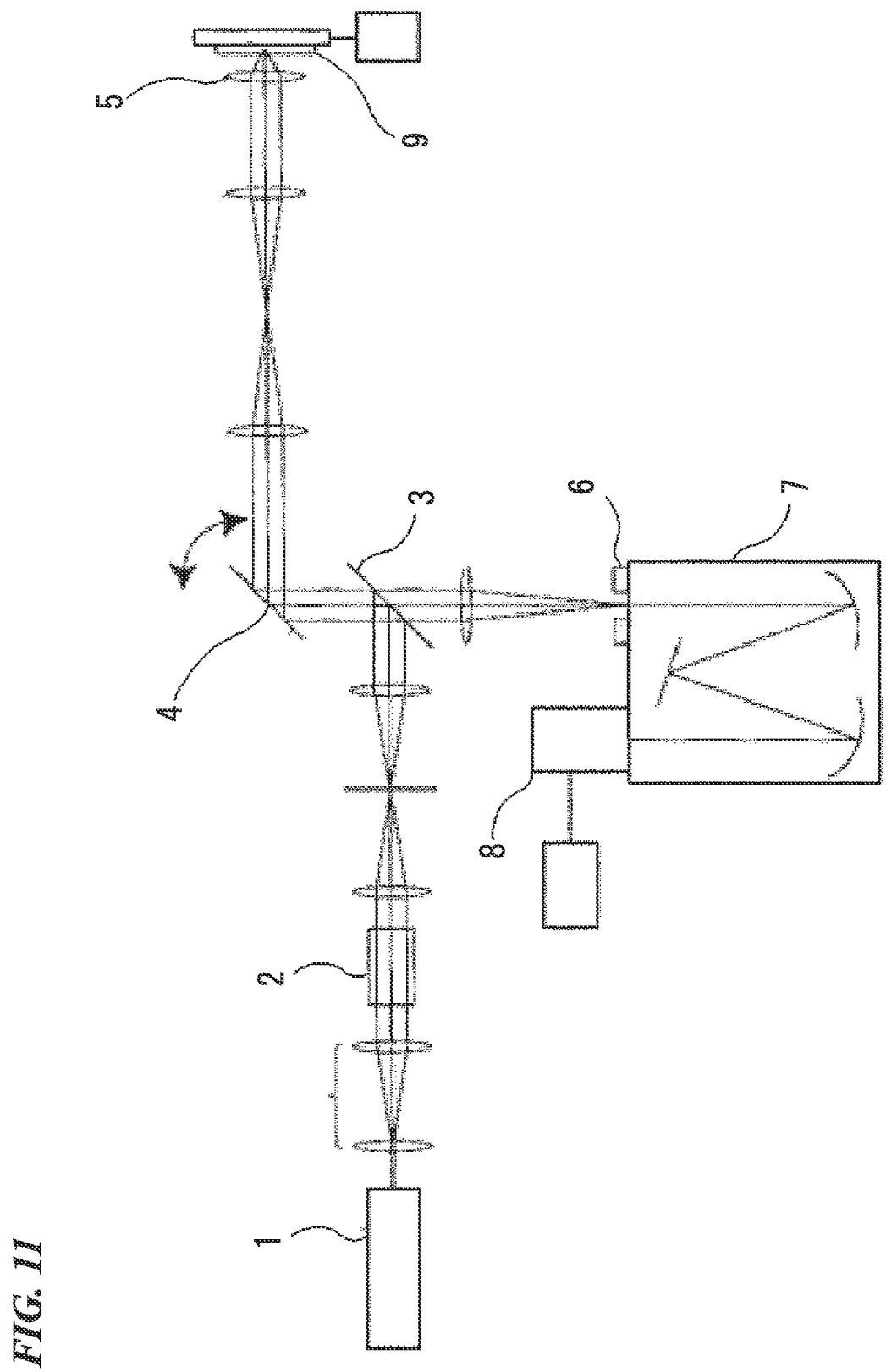
FIG. 11 is a drawing showing an example of the constitution of a microscope spectrometer in accordance with the related art.

FIG. 10 is a constitution diagram illustrating a microscope spectrometer in accordance with a fourth preferred embodiment of the present invention. Parts that are the same as in FIG. 9 are assigned the same reference numerals, and the descriptions thereof are arbitrarily omitted.

Main points of difference with respect to FIG. 9 are the provision of an optical axis adjustment means for adjusting the optical axis, and control by the control means of the optical axis adjustment means to control the angle of incidence of the scattered light for the purpose of correcting the position shift occurring in the XY direction.

With the constitutions up until FIG. 9, in the case in which the first variable bandpass filter 24 and the second variable bandpass filter 29 are light incidence direction tuned types, there was the problem of a position shift occurring in the XY direction of the optical axis, depending upon the angle adjustment. In the present preferred embodiment, in addition to the objects described above, there is the object of being able to correct the position shift occurring in the XY direction by controlling the optical axis adjustment means.

In FIG. 10 the microscope spectrometer of the present invention has, installed between the first optical means 23 and the variable bandpass filter 24, an optical axis adjustment means 31 such as an optical plate that transmits light, that changes and adjusts the incidence angle of the scattered light to adjust the optical axis.

The optical axis adjustment means 31 is electrically connected to the control means 27, and a control signal from the control means 27 controls the angle of incidence of scattered light.

As a result, the microscope spectrometer of the present invention is effective regarding the point of changing the angle of the scattered light from the first variable bandpass filter 24 with respect to the optical axis by the optical axis adjustment means 31, based on the angle of incidence of the scattered light in the first variable bandpass filter 24 and the second variable bandpass filter 29 to control the position of the optical axis in the X and Y directions, thereby enabling correction of position shift occurring in the XY direction.

Also, by having the optical axis adjustment means 31, the microscope spectrometer of the present invention is effective with regard to the point of performing spectral dispersion while scanning a microscopically observed planar region, so as to enable spectral dispersion at a position desired by the user. Specifically, by having the optical axis adjustment means 31, the microscope spectrometer of the present invention is effective with regard to the point of performing spectral dispersion while scanning wavelengths in a planar region being microscopically observed, so as to perform spectral dispersion at a position desired by the user.

Figure 12:
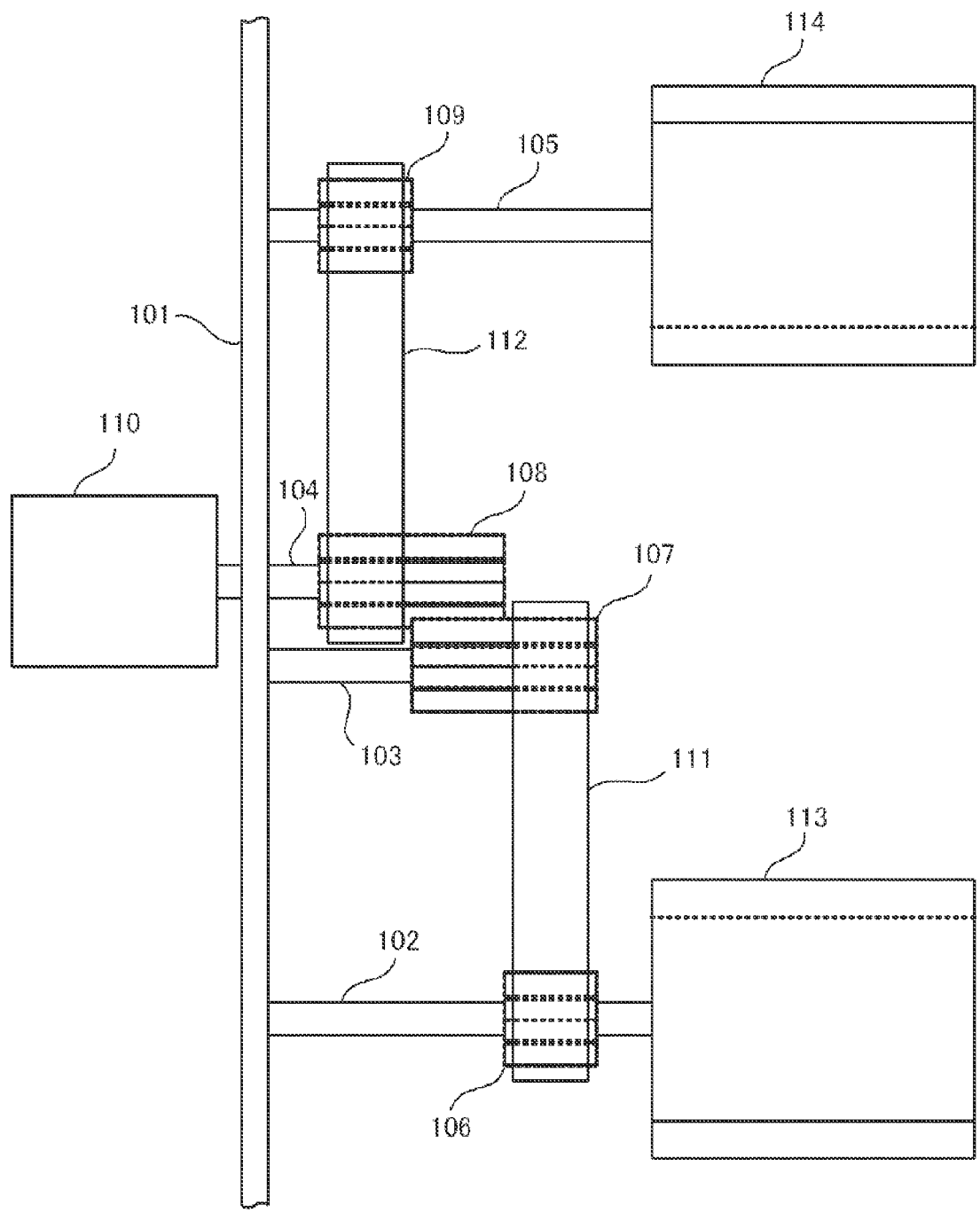
FIG. 12 is a side view of the constitution that shows one preferred embodiment of the present invention.
Figure 13:
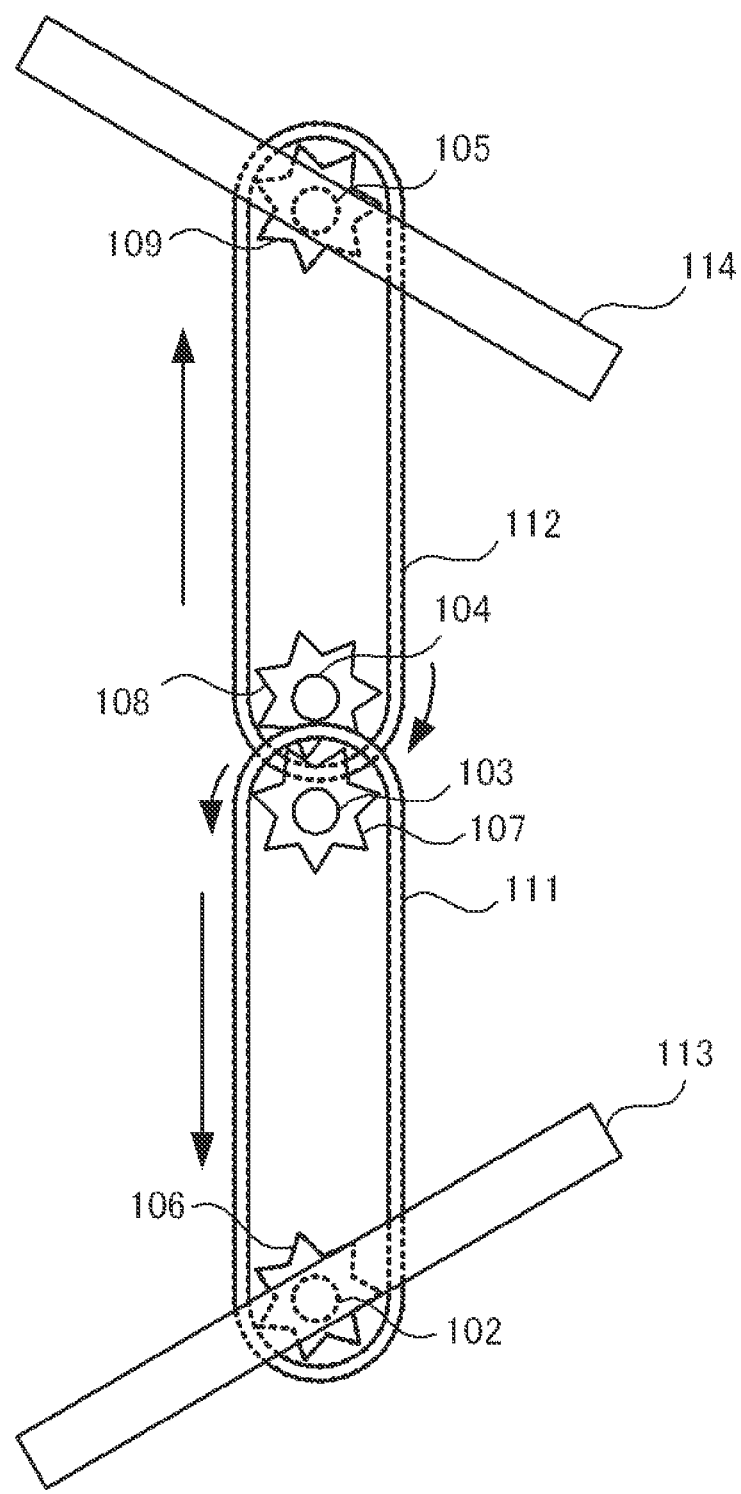
FIG. 13 is a constitution diagram seen from above in FIG. 12.

FIG. 12 is a side view of the constitution that shows one preferred embodiment of the present invention. FIG. 13 is a constitution diagram seen from above in FIG. 12. In FIG. 12 and FIG. 13, four shafts 102 to 105 are mounted on a support plate 101 so as to smoothly rotate with, for example, intervening bearings. Pulleys 106 to 109 are fixed to the shafts 102 to 105, respectively.

A rotational drive source 110 (for example, a motor) is linked to the shaft 104, pulley 106 and pulley 107 are linked via a belt 111, pulley 108 and pulley 109 are linked via a belt 112, and the pulley 107 and the pulley 108 are linked by direct contact between the outer peripheries thereof.

An optical filter 113 is mounted to the shaft 102, and a corrective optical plate 114 is mounted to the shaft 105.

In a constitution such as noted above, the rotation of the rotational drive source 110 is transmitted to the corrective optical plate 114, via the transmission system of the shaft 104 to the pulley 108, to the belt 112, to the pulley 109, and then to the shaft 105 to rotate the corrective optical plate 114, and is transmitted to the optical filter 113 via the transmission system of the shaft 104 to the pulley 108, to the pulley 107, to the belt 111, to the pulley 106, and then to the shaft 102 to rotate the optical filter 113. In this case, because the pulley 107 and the pulley 108, as shown in FIG. 13, are linked by direct contact between the outer peripheries thereof, they rotate in mutually opposite directions.

Figure 14:
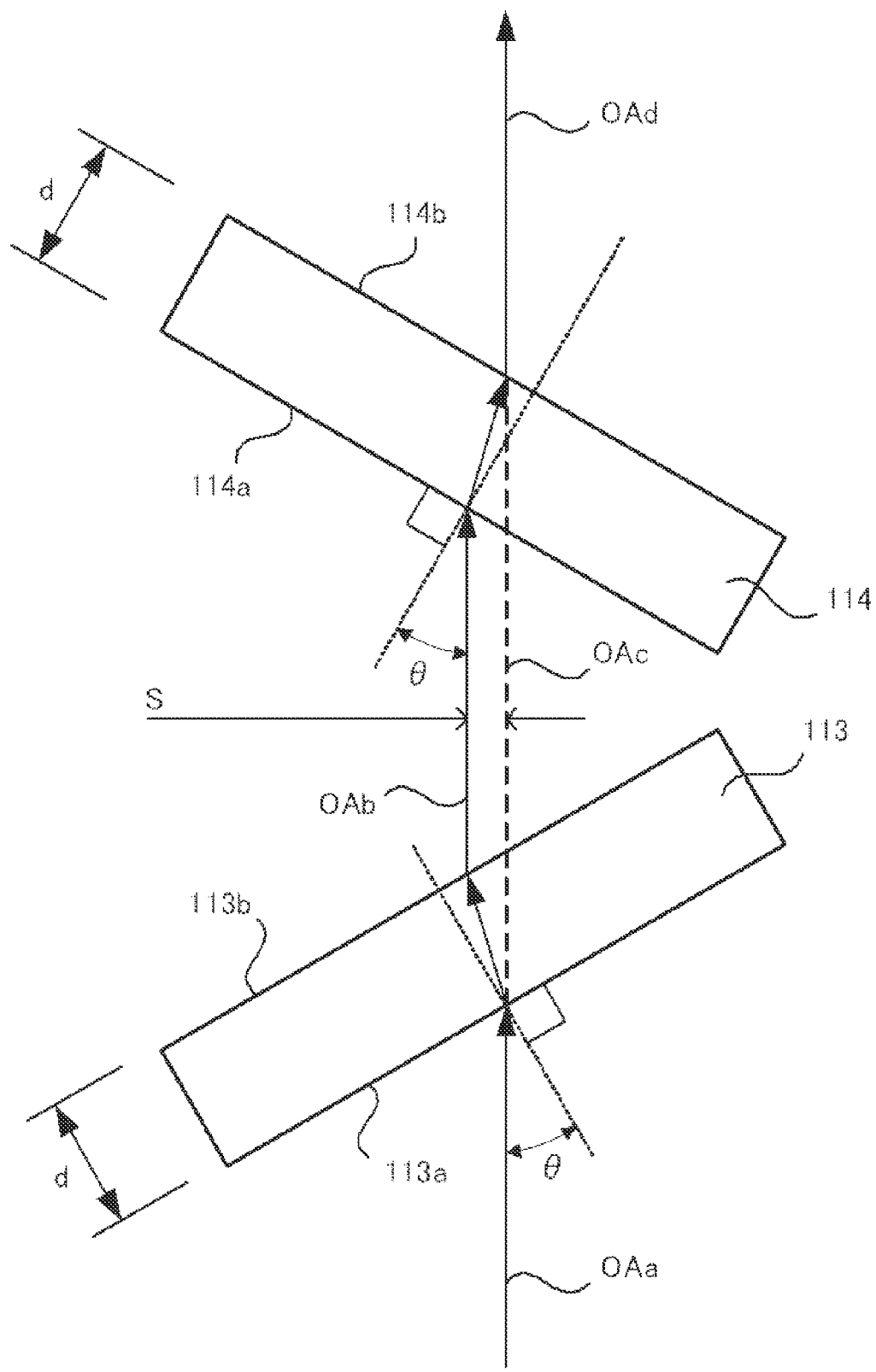
FIG. 14 is a diagram describing the light path, focusing on the optical filter 113 and the corrective substrate 114, which are optical components shown in FIG. 13.

FIG. 14 is a diagram describing the light path, focusing on the optical filter 113 and the corrective substrate 114, which are optical components shown in FIG. 13. In FIG. 14, the optical filter 113 is disposed at an angle of inclination that is rotated by an angle of θ in the counter-clockwise direction from a position that is perpendicular with respect to the optical axis OAa that is in the forward advance direction. In contrast, the corrective optical plate 114 is disposed at an angle of inclination that is rotated by an angle of θ in the clockwise direction from a position that is perpendicular with respect to the optical axis OAa that is in the forward advance direction.

Light, reaches the front surface 113a of the optical filter 113 along the optical axis OAa, and is incident to the optical filter 113. Light that is incident to the optical filter 113 is refracted within the optical filter 113 and transmitted in accordance with Snell's law, and reaches the optical filter rear surface 113b.

Light that has reached the rear surface 113b of the optical filter 113 is again refracted, in accordance with Snell's law, and proceeds along the optical axis OAb, which is parallel to the optical axis OAa, reaches the front surface 114a of the corrective optical plate 114, and is incident to the corrective optical plate 114. When this occurs, a shift occurs in the optical axis OAb by a distance of S with respect to the original optical axis OAc, which should be on a line extending from the optical axis OAa. This optical axis shift of S can be expressed as a function of inclination angle θ, the thickness d, and the refractive index n of the optical filter 113.

The light that is incident to the front surface 114a of the corrective optical plate 114 is refracted, in accordance with Snell's law, in the direction that cancels out the optical axis shift by the distant S caused by passing through the optical filter 113 in accordance with the internal refractive index n thereof, and reaches the rear surface 114b of the corrective optical plate 114.

The light that reaches the rear surface 114b of the corrective optical plate 114 is again refracted in accordance with Snell's law, and proceeds along the original optical axis OAd, which is a line extending from the optical axis OAa.

That is, by making the refractive index n and the thickness d of the corrective optical plate 114 the same as the refractive index n and the thickness of the optical filter 113, and rotational driving the optical filter 113 and corrective optical plate 114 in a linked manner, so that the angle of inclination θ of the optical filter 113 in the counter-clockwise direction with respect to the optical axis OAa is always the same as the angle of inclination θ of the corrective optical plate 114 in the clockwise direction with respect to the optical axis OAd, the optical axis shift by the distance S caused by passing through the optical filter 113 is cancelled out, and the light exiting from the rear surface 114b of the corrective optical plate 114 is made to coincide with the original optical axis OAd that is a line extending from the optical axis OAa of incidence from the front surface 113a of the optical filter 113.

By doing this, it is possible to implement an optical filter with no optical axis shift, without the conventionally troublesome calibration task.

For example, it is possible to measure continuously, even with a variable wavelength optical filter of the angular modulation type. If it is desired to measure in real time while varying the incidence angle of the light, although an optical axis shift occurs, accompanying the change in the angle of incidence of the light, because application of the present invention enables automatic correction of the optical axis shift, continuous measurement without breaks is possible.

Although in the preferred embodiment of FIG. 12 the example shown is one in which the rotational drive source 110 is linked to the shaft 104, the shaft that links the rotational drive source 110 is not restricted to 104, and may be another shaft 102, 103, or 105.

Figure 15:
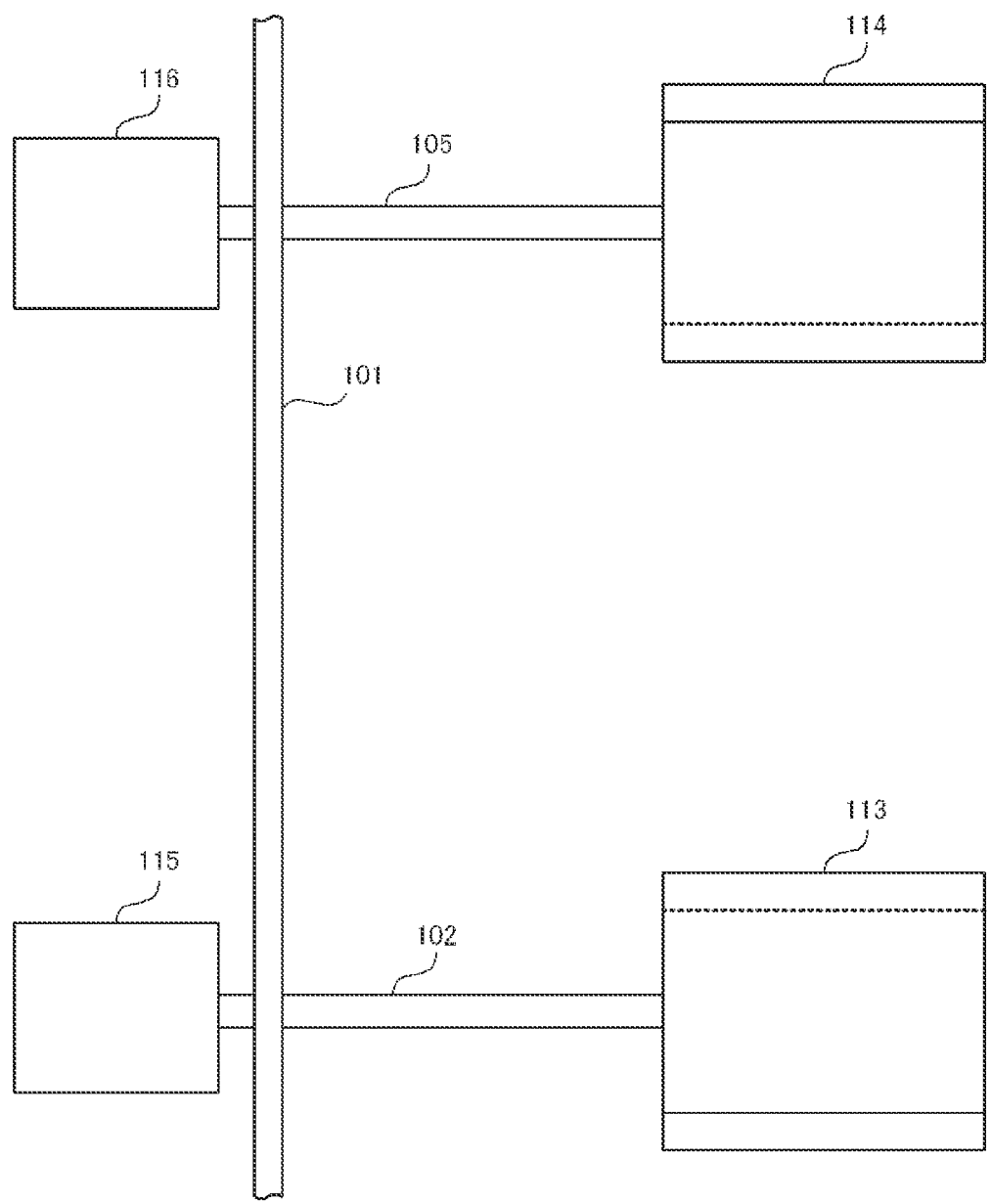
FIG. 15 is a constitution diagram showing another preferred embodiment of the present invention.

FIG. 15 is a constitution diagram showing another preferred embodiment of the present invention. In FIG. 15, a rotational drive source 115 is linked to the shaft 102, to which the optical filter 113 is mounted, and a rotational drive source 116 is linked to the shaft 105, to which the corrective optical plate 114 is mounted.

By the rotational drive source 115 and the rotational drive source 116 rotating the optical filter 113 and corrective optical plate 114 through equal angles in each of their respective directions, similar to FIG. 14, proper rotational drive control is performed so as to correct the optical axis shift.

As described above, according to the present invention, it is possible to implement an optical axis correction device capable of correcting optical axis shift with a relatively simple constitution, this being suitable for optical axis shift correction in various optical apparatuses, such as spectroscopes and microscopes.

Fifth Preferred Embodiment

Figure 16:
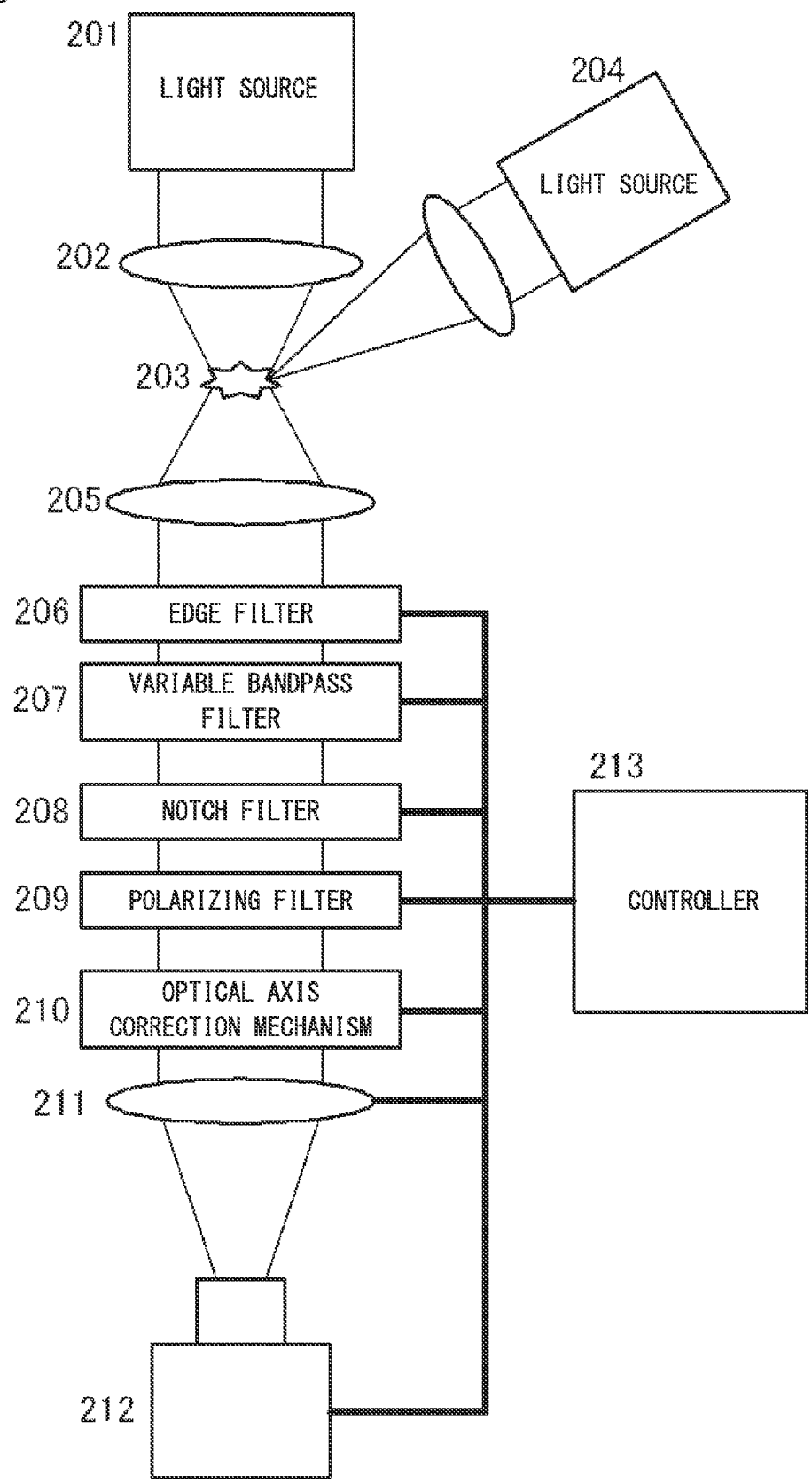
FIG. 16 is a constitution diagram illustrating a spectroscope that uses an optical axis shift correction device in accordance with a fifth preferred embodiment of the present invention.

FIG. 16 is a constitution diagram illustrating a spectroscope that uses an optical axis shift correction device in accordance with a fifth preferred embodiment of the present invention. In FIG. 16, the output light of the light source 201 illuminates an object under measurement 203, which is a sample, via a light illumination lens optical system 202. In illuminating the object under measurement 203, illumination may be done from a position that is shifted from the optical axis, such as a light source 204.

It is sufficient that there be at least one of the light sources 201 and 204, and the light sources 201 and 204 may be single-wavelength light sources such as lasers, or alternatively may be wideband wavelength light sources.

The light from the object under measurement 203 is broadened by the objective lens optical system 205 and, by the action of an edge filter 206, is limited to the short-wavelength region or long-wavelength region thereof.

The output light of the edge filter 206 is spectrally dispersed by passing through a variable bandpass filter 207. The output light that has been spectrally dispersed by the variable bandpass filter 207 passes through the optical path that is formed by a notch filter 208, then a polarizing filter 209, then an optical axis adjustment optical system 210, and then an image-forming optical system 211, and is incident to a two-dimensional array detector 212.

An optical interference type or light incidence angle tuning type filter can be used as the variable bandpass filter 207.

Although the notch filter 208 is not essential, it is best to have it in the case in which the light source 201 or 204 is a single-wavelength light source.

An optical axis shift correction device based on the present invention as described above is used as the optical axis adjustment optical system 210.

A CMOS image sensor or CCD image sensor or the like can be used as the two-dimensional array detector 212.

The edge filter 206, the variable bandpass filter 207, the notch filter 208, the polarizing filter 209, the optical axis adjustment optical system 210, and the two-dimensional array detector 212 are connected to a controller 213.

The edge filter 206, the notch filter 208, and the polarizing filter 209 are controlled by the controller 213 to be inserted into or removed from the optical axis, as required. The variable bandpass filter 207, the optical axis adjustment optical system 210, and the two-dimensional array detector 212 are controlled by the controller 213 so as to achieve desired conditions of the spectrally dispersed wavelength region and timing. The edge filter 206, the notch filter 208, and the polarizing filter 209 are controlled by the controller 213 to control the polarization direction, as required.

Figure 17:
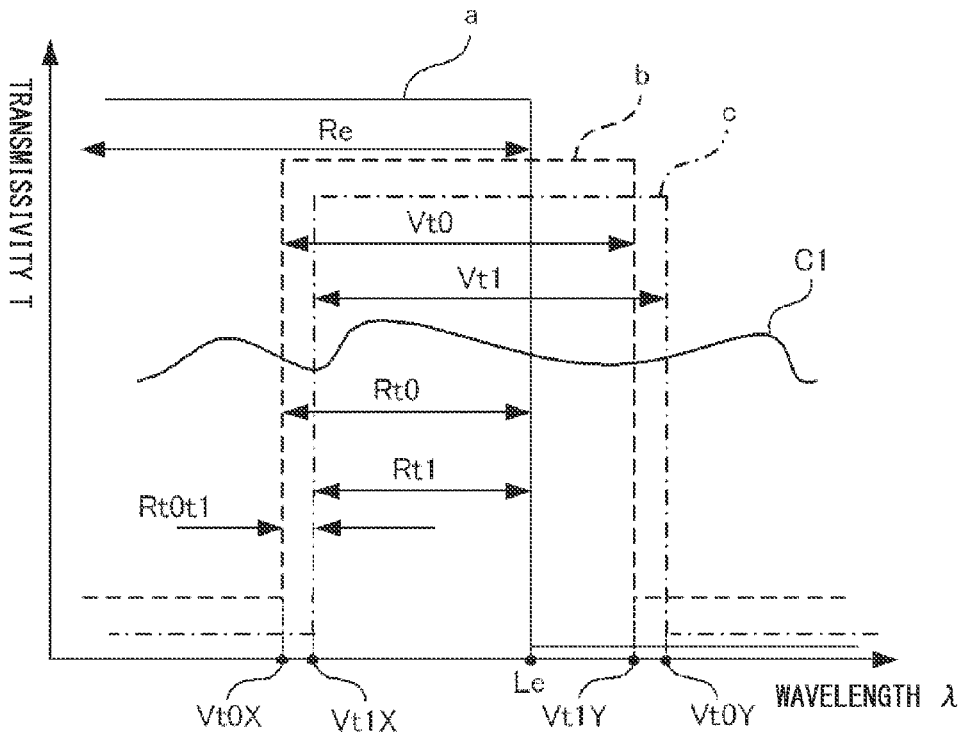
FIG. 17 is a diagram describing a wavelength region that is spectrally dispersed by the constitution of FIG. 16.

The operation in FIG. 16 will be described using FIG. 17 and FIG. 18. FIG. 17 describes the wavelength region that is spectrally dispersed by the edge filter 206 and the variable bandpass filter 207. The horizontal axis represents the wavelength $\lambda$, and the vertical axis represents the transmissivity T.

In FIG. 17, the spectral wavelength region from t0 to t1 of C1 is spectrally dispersed. The solid line a indicates the light transmission region of the edge filter 206, this meaning that light in the short-wavelength region below the wavelength region Le.

The single-dot dashed line c indicates the transmission region of the variable bandpass filter 207. By modulating the transmission region, the condition of the dashed line b, in which the region of the wavelength range Vt0=Vt0Y−Vt0X is transmitted, and the condition of the single-dot dashed line c, in which the region of the wavelength range Vt1=Vt1Y−Vt1X is transmitted are created. In FIG. 17, although the solid line a, the dashed line b, and the single-dot dashed line c are drawn so that the transmissivities are mutually different, this is a convenience of description, and has no particular significance.

In the case of the dashed line b, because the transmitted wavelength region is formed by a long-wavelength side that the transmission region of the edge filter 206 and the transmission region of the variable bandpass filter 207, this is Rt0=Vt0X−Le. The amount of light in this condition is first measured, this amount of light being taken as E_Rt0.

Next, the amount of light in the case of the single-dot dashed line c is measured. In this case, the transmitted wavelength region is Rt1=Vt1X−Le, and the amount of light is taken as E_Rt1.

The amounts of light in the condition of the solid line a and the single-dot dashed line c, these being E_Rt0 and E_Rt1, are held by a storage function of the controller 213.

The controller 213 performs processing to subtract the amount of light E_Rt1 from the amount of light E_Rt0, the difference amount of light being calculated as E_Rt(0−1)=E_Rt0−E_Rt1.

In this case, E_Rt(0−1) means the amount of light in the wavelength region Rt0t1=Vt0X−Vt1X. That is, with respect to the spectrum C1, a spectral output in this wavelength region has been obtained. The above-noted "measurement of the amount of light" means a planar imaging by the two-dimensional array detector 212. By doing this, the controller 213 stores the measured amounts of light at each pixel in the two-dimensional array detector 212 and performs subtraction to output the spectral results for each of the pixels.

Next, a different region of the spectrum C1 is spectrally dispersed.

Figure 18:
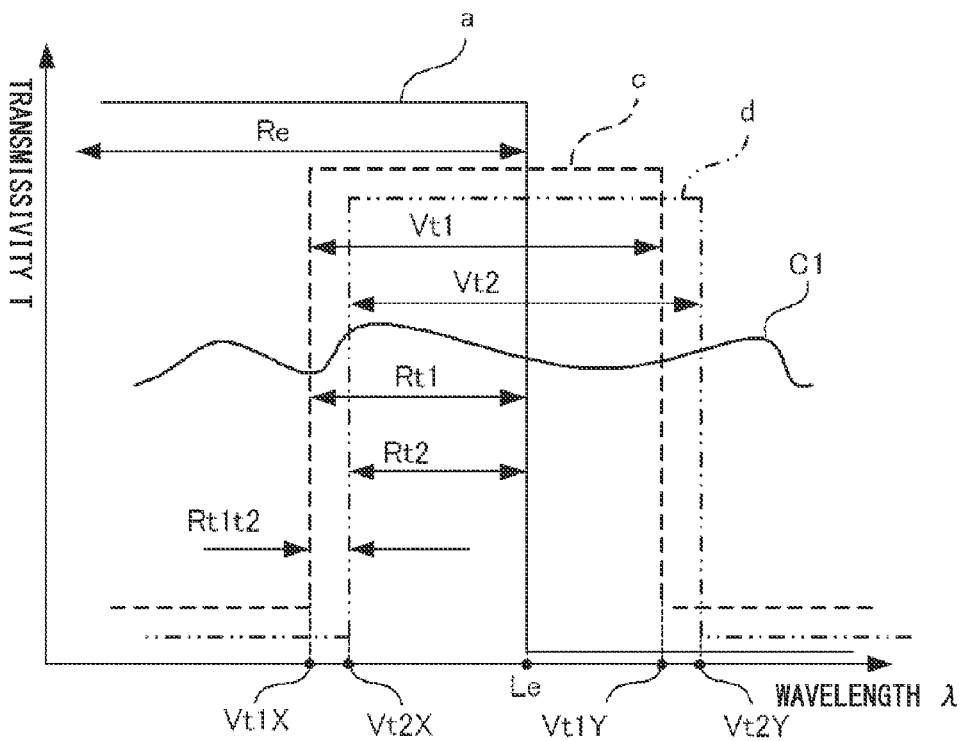
FIG. 18 is a diagram describing another wavelength region that is spectrally dispersed by the constitution of FIG. 16.
Figure 19:
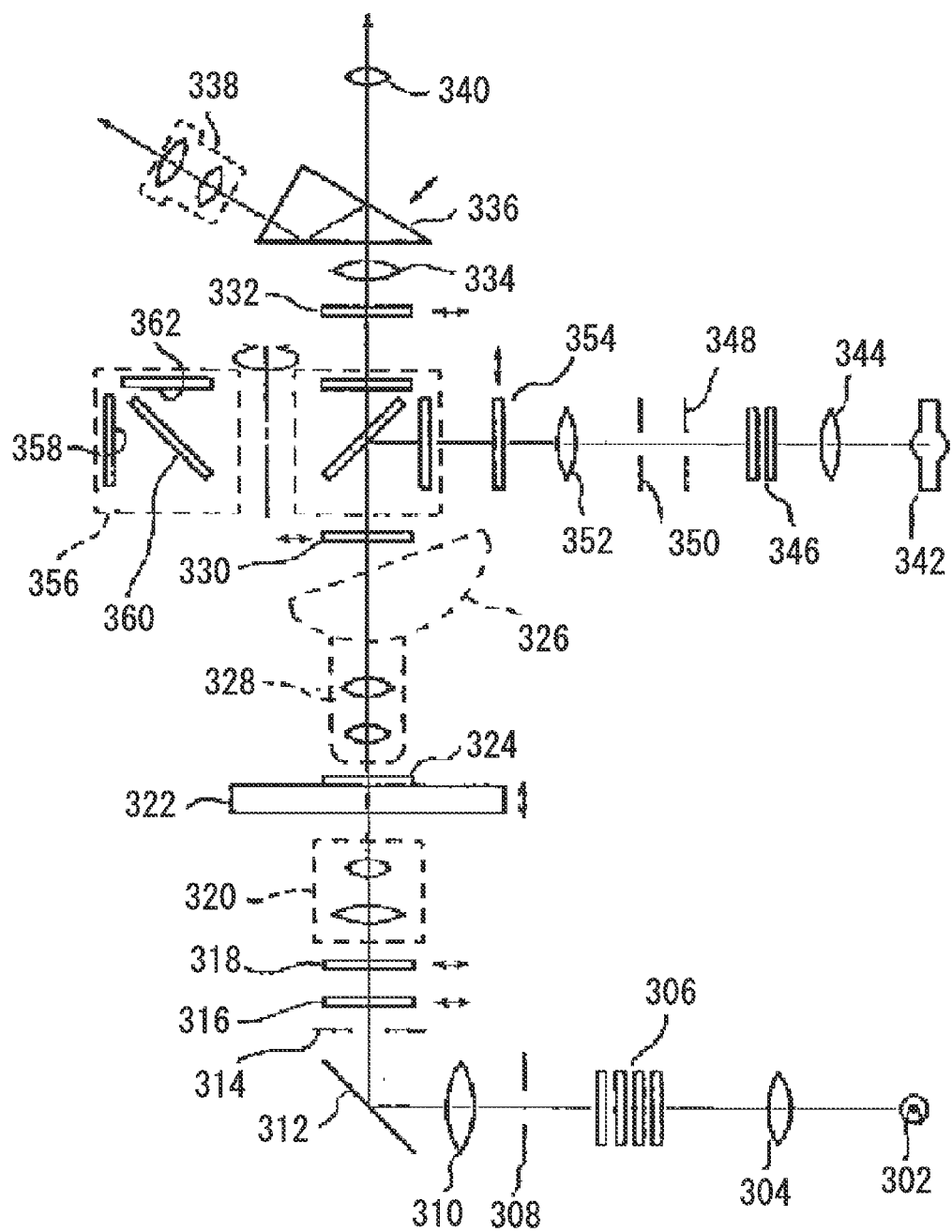
FIG. 19 is a constitution diagram illustrating an optical microscope having an afocal observation optical system.
Figure 20A:
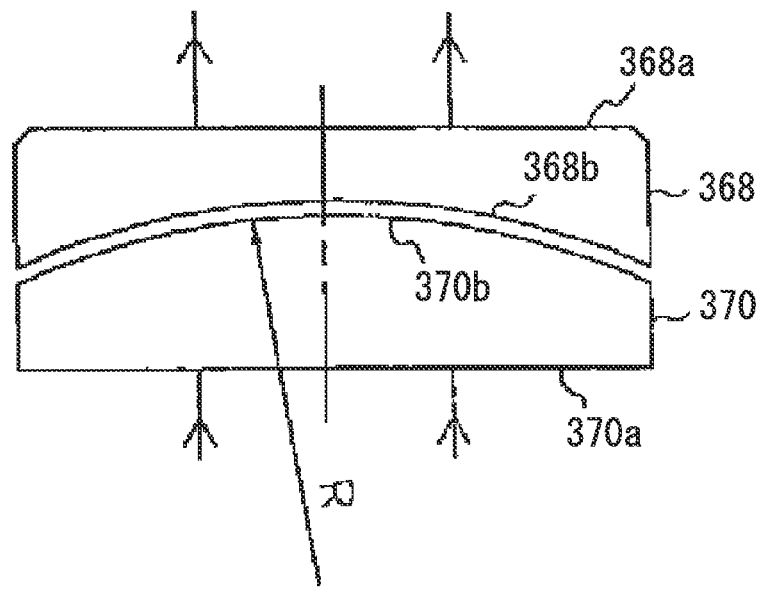
FIG. 20A and FIG. 20B are diagrams describing the constitution of a center correction unit used in FIG. 19.
Figure 20B:
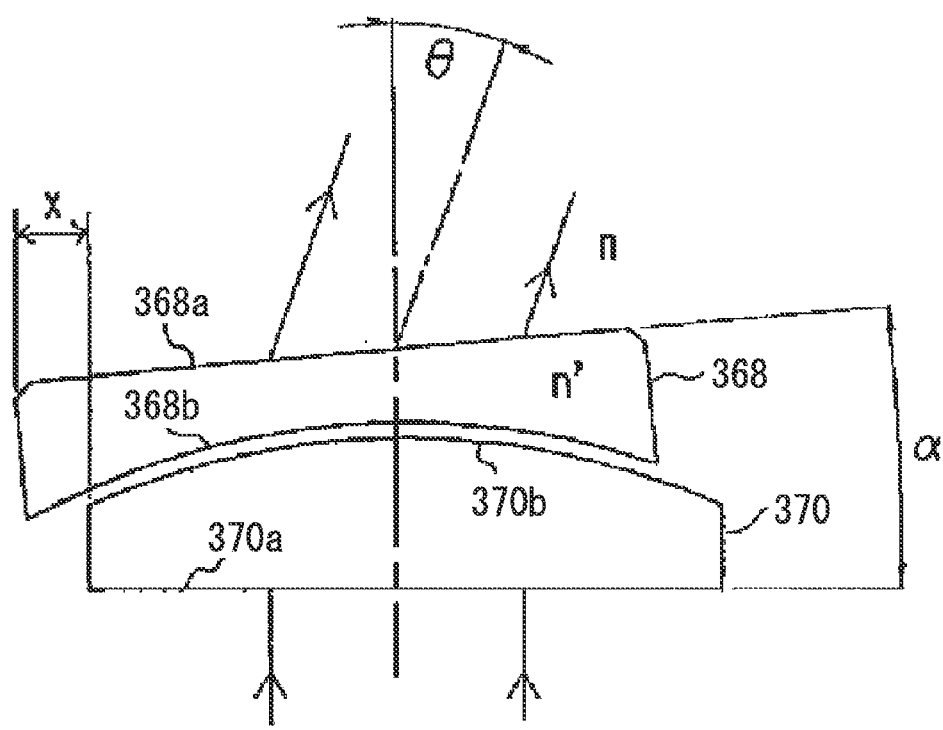

FIG. 18 is a diagram describing a wavelength region that indicates the condition in which the light transmission region of the variable passband filter 207 is modulated, so that transmission is done in a longer wavelength region. The horizontal axis represents the wavelength $\lambda$, and the vertical axis represents the transmissivity T.

In FIG. 18, the wavelength region from t1 to t2 of the spectrum C1 is spectrally dispersed. The solid line a indicates the light transmission region of the edge filter 206. The dashed line c indicates the transmission region of the variable bandpass filter 207, and the light amount E_Rt1 in this case is at this point stored in the controller 213. The double-dot dashed line d is the condition in which the variable bandpass filter 207 is controlled to modulate it so that light is transmitted in a longer wavelength region Vt2=Vt2Y−Vt2X.

In such a condition, calculation processing similar to that of FIG. 17 is performed. In this case, the net light transmission region is Rt1t2=Rt1−Rt2=(Le−Vt1X)−(Le−Vt2X).

The transmitted amount of light at this time is calculated as E_Rt(1−2)=E_Rt1−E_Rt2.

By the above, a spectral output on the long wavelength side with respect to the spectrum C1 is obtained.

By continuously repeating the execution of the processing operations described by FIG. 17 and FIG. 18, spectral processing is performed over the entire wavelength region of the spectrum C1.

By the constitution shown in FIG. 16 it is possible to constitute a compact, low-cost spectroscope with one less of the edge filter 206 a variable bandpass filter 207 as optical components.

Additionally, by using a spectroscope constituted in this manner and the two-dimensional array detector 212, it is possible to perform two-dimensional (XY) planar spectral dispersion without a time delay, thereby enabling spectral dispersion of the same wavelength region for a given measurement time.

It is also possible to perform high-speed spectral dispersion, based on the imaging speed of the two-dimensional array detector 212.

Additionally, because the control precision itself of the transmission region of the variable bandpass filter 207 becomes the wavelength resolution, high wavelength resolution is achieved.

Although the descriptions of FIG. 17 and FIG. 18 assumed the use of a short-pass filter constituted so as to transmit light in a short-wavelength region as the edge pass filter 206, a long-pass filter that transmits light in a long-wavelength region may be used.

Also, by using the polarizing filter 209 as shown in FIG. 16, it is possible to perform spectral dispersion with polarization dependency.

By using a polarizing filter 209 such as shown in FIG. 16, it is possible to perform spectral dispersion while controlling the polarization direction.

By constituting the image-forming optical system 211 of FIG. 16 as a confocal optical system, it is possible to measure in the depth direction of the object under measurement 203.

Additionally, by using a spectroscope constituted in this manner in a microscope, it is possible to implement a microscope having the above-noted superior spectroscopic characteristics and, by using the image-forming optical system 211 shown in FIG. 16 as a confocal optical system, it is possible to implement a confocal microscope capable of measurement in the depth direction of the object under measurement 203.

Sixth Preferred Embodiment

Figure 21:
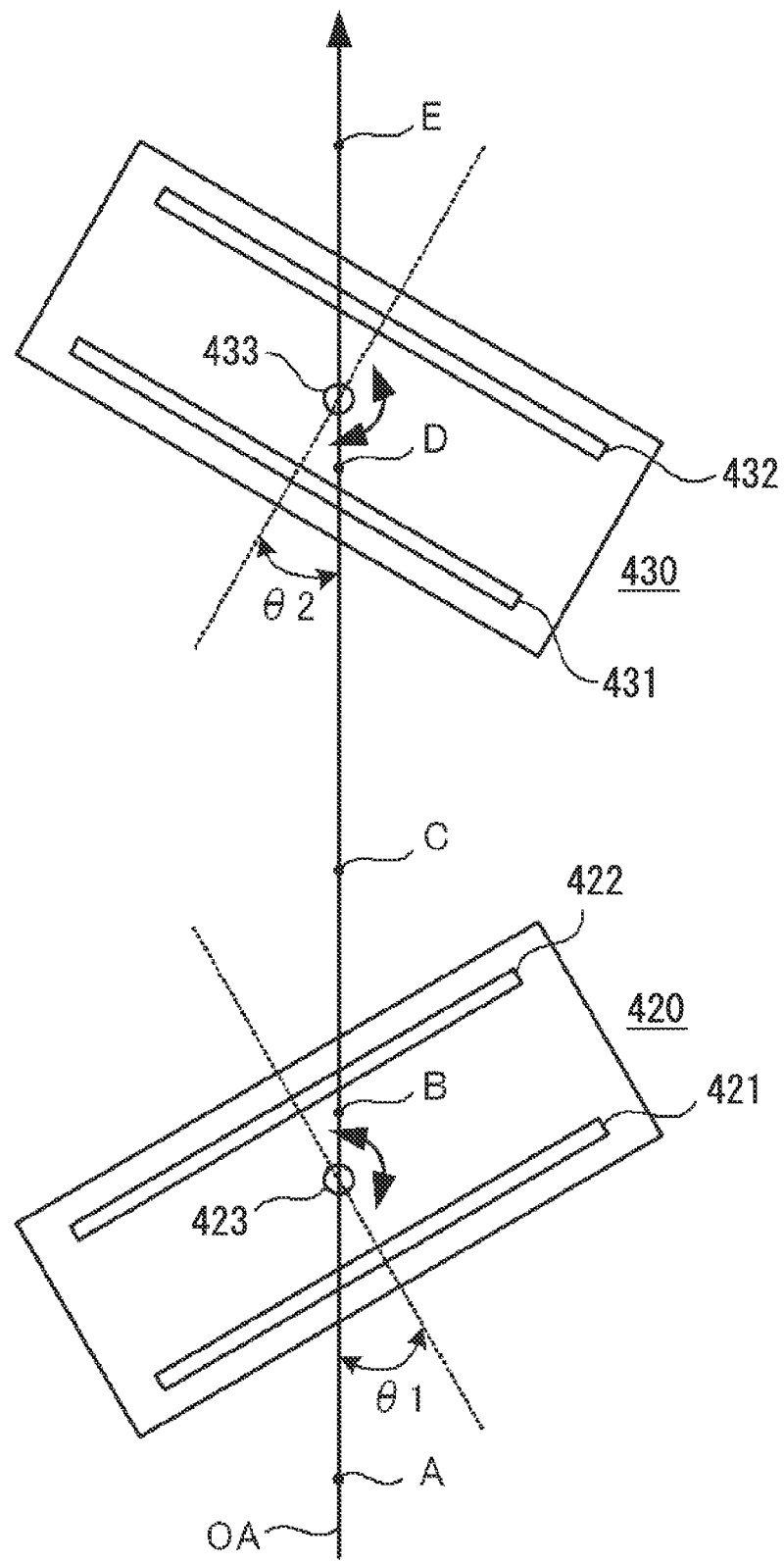
FIG. 21 is a constitution diagram describing a sixth preferred embodiment of the present invention.

FIG. 21 is a constitution diagram describing a sixth preferred embodiment of the present invention. In FIG. 21, variable bandpass filters 421 and 422 are fixed to a rectangular filter support plate 420 in parallel with the vertical direction to form a first filter group, and variable bandpass filters 431 and 432 are fixed to a rectangular filter support plate 430 in parallel with the vertical direction.

A rotating shaft 423 is provided in the center part of the filter support plate 420 for the purpose of rotating the filter support plate 420 an arbitrary angle θ1, and a rotating shaft 433 is provided in the center part of the filter support plate 430 for the purpose of rotating the filter support plate 430 an arbitrary angle θ2. The filter support plates 420 and 430 are rotationally driven by a rotating mechanism (not shown) so as to be at desired angles of θ1 and θ2 with respect to the optical axis.

The variable bandpass filters 421 and 422 and the variable bandpass filters 431 and 432 vary the transmitted wavelength region in accordance with the angle of incidence of the light.

Figure 22:
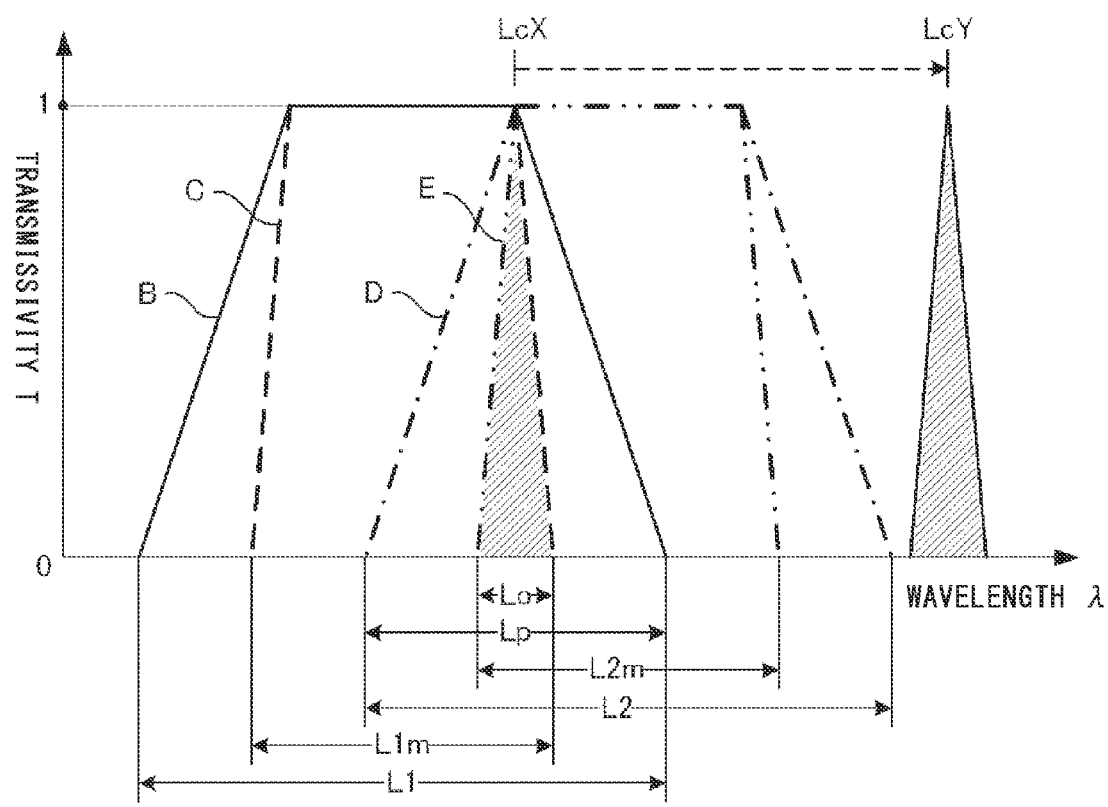
FIG. 22 is a drawing of the spectra at each of the points B to E on the optical axis OA in the constitution of FIG. 21.

FIG. 22 is a drawing of the spectra at each of the points B to E on the optical axis OA in the constitution of FIG. 21. The description will be for the case of light that is incident from the point A along the optical axis OA.

The solid line B indicates the transmitted wavelength region of the variable bandpass filter 421, this being a trapezoidal region with L1 as the base. This corresponds to the transmission spectrum at point B in FIG. 21.

The dashed line C indicates the transmitted wavelength region of the variable bandpass filter 422, this being a trapezoidal region with L1m as the base. This corresponds to the transmission spectrum at point C in FIG. 21.

In this manner, by passing light from the position A on the optical axis OA through the two variable bandpass filters 421 and 422 that are fixed to the filter support plate 420, bandpass filtering with steep edges is possible.

The single-dot dashed line D indicates the transmitted wavelength region of the variable bandpass filter 431, this being a trapezoidal region with L2 as the base. This corresponds to the transmission spectrum at point D in FIG. 21

The double-dot dashed line E indicates the transmitted wavelength region of the variable bandpass filter 432, this being a trapezoidal region with L2m as the base. This corresponds to the transmission spectrum at point E in FIG. 21.

In the same manner, by passing light through the two variable bandpass filters 431 and 432 that are fixed to the filter support plate 430, bandpass filtering with steep edges is possible.

Ultimately, the transmitted wavelength region at point E in FIG. 21 obtained by passing light through the four variable bandpass filters 421, 422, 431, and 432, is the hatched triangular region with the base Lo in FIG. 22.

If, in the constitution of FIG. 21, the variable bandpass filters 422 and 432 are not used, the transmitted wavelength region by the variable bandpass filters 421 and 432 would be a triangular region with the base Lp in FIG. 22, and it would not be possible to obtain good edge steepness.

In this manner, by passing light through a plurality of variable bandpass filters, it is possible to spectrally disperse a narrow transmitted wavelength region.

By properly changing the angle θ1 of the filter support plate 420 and the angle θ2 of the filter support plate 430, it is possible to move the center wavelength LcX of the triangle having the base Lo of FIG. 22 to LcY. This movement of the center wavelength Lc means that continuous spectral dispersion is possible from the center wavelength LcX to LcY.

That is, in addition to passing light through a plurality of variable bandpass filters, by being able to arbitrarily adjust the mounting angle of the variable bandpass filters with respect to the optical axis, it is possible to obtain spectral dispersion over a narrow wavelength region and also spectral dispersion with variable wavelength.

Figure 23:
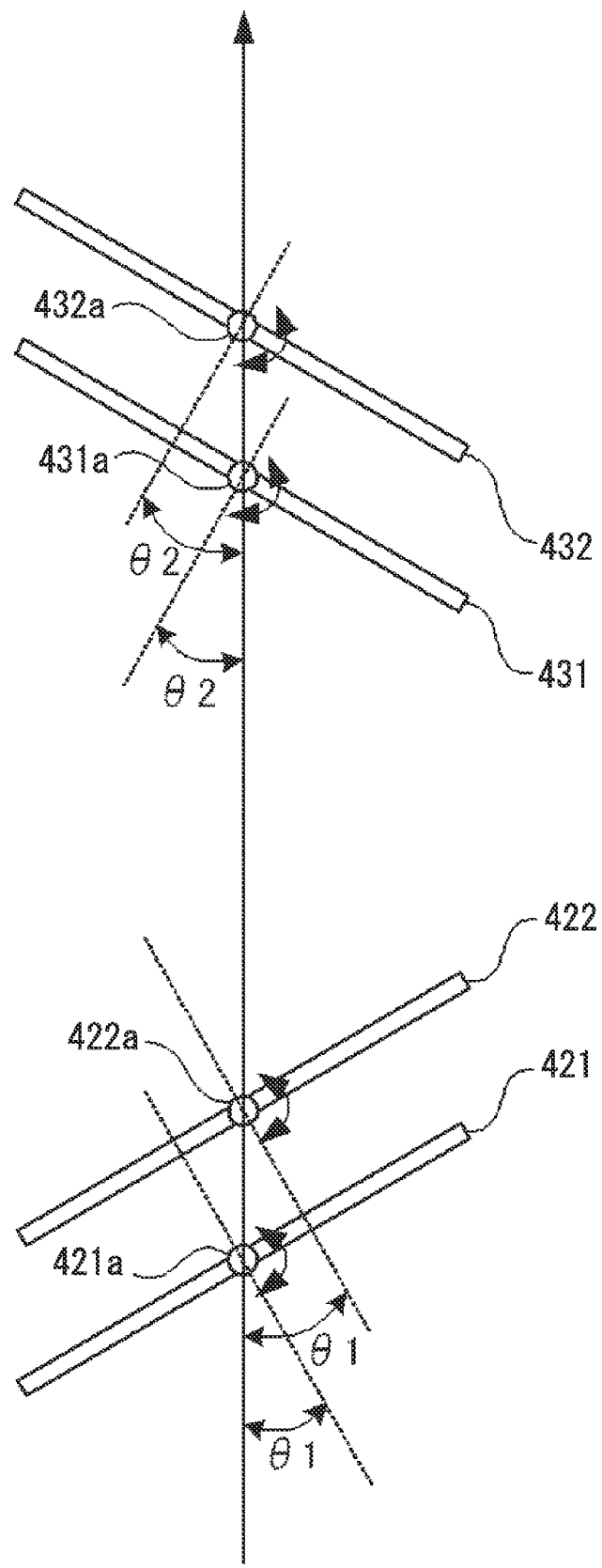
FIG. 23 is a constitution diagram describing another preferred embodiment of the present invention.

FIG. 23 is a constitution diagram describing another preferred embodiment of the present invention, with parts that are the same as in FIG. 21 assigned the same reference numerals. In the preferred embodiment of FIG. 23, the four variable bandpass filters 421, 422, 431, and 432 are mounted to prescribed mounting parts via mutually independent rotating shafts 421, 422, 431, and 432, without the intervening filter support plates 420 and 430.

In FIG. 23, the variable bandpass filters 421 and 422 form a first filter group, and the variable bandpass filters 431 and 432 form a second filter group.

According to the constitution of FIG. 23, compared with the constitution of FIG. 21 in which there are the intervening filter support plates 420 and 430, it is possible to reduce the width of the space required to rotate the variable bandpass filters 421, 422, 431, and 432, thereby enabling downsizing when incorporated into an apparatus.

In the preferred embodiment of FIG. 21, the variable bandpass filters 421 and 422 are mounted to the filter support plate 420 so as to be mutually parallel, and the variable bandpass filters 431 and 432 are mounted to the filter support 430 so as to be mutually parallel, and in the preferred embodiment in FIG. 23, the variable bandpass filters 421 and 422 are mounted so as to be mutually parallel at equal angles θ1 with respect to the optical axis, and the variable bandpass filters 431 and 432 are mounted so as to be mutually parallel at equal angles θ2 with respect to the optical axis. However, the combination of the variable bandpass filters 421 and 422 and the combination of the variable bandpass filters 431 and 432 need not be parallel. Individual angles may be separately set, so as to obtain the desired overall transmission characteristics, taking into consideration variations in the transmission characteristics of the variable bandpass filters 421, 422, 431, and 432.

Figure 24:
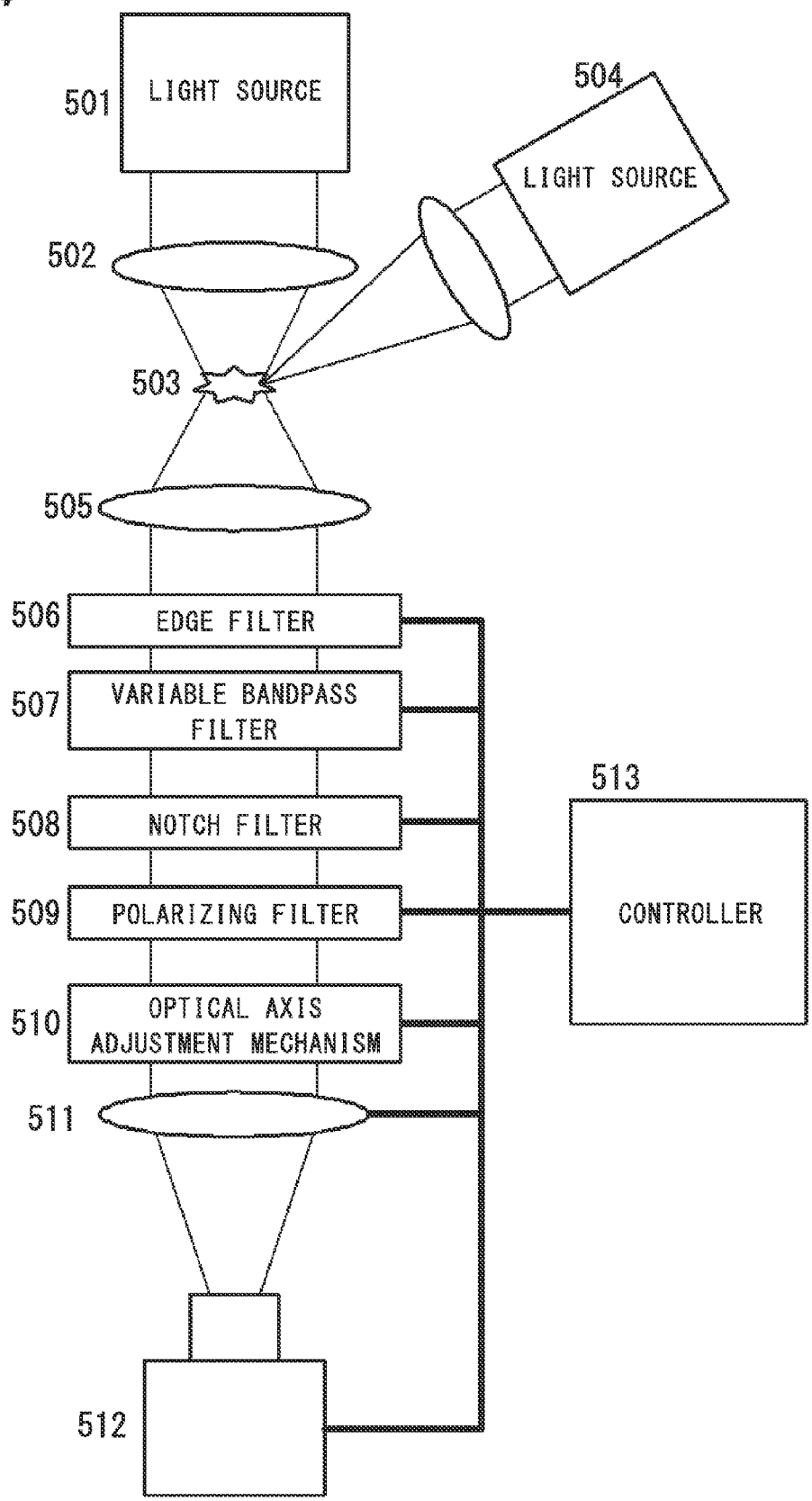
FIG. 24 is a constitution diagram describing a spectroscopic unit that uses a spectroscope in accordance with a preferred embodiment of the present invention.

FIG. 24 is a constitution diagram describing a spectroscopic unit that uses a spectroscope in accordance with a preferred embodiment of the present invention.

In FIG. 24, the output light of a light source 501 illuminates the object under measurement 503 via a light illumination optical system 502. In illuminating the object under measurement 503, illumination may be done from a position that is shifted from the optical axis, such as a light source 504.

It is sufficient that there be at least one of the light sources 501 and 504, and the light sources 501 and 504 may be single-wavelength light sources such as lasers, or alternatively may be wideband wavelength light sources.

The light from the object under measurement 503 is broadened by the objective lens optical system 505 and, by the action of an edge filter 506, is limited to the short-wavelength region or long-wavelength region thereof.

The output light of the edge filter 506 is spectrally dispersed by passing through a variable bandpass filter 507. The output light that has been spectrally dispersed by the variable bandpass filter 507 passes through the optical path that is formed by a notch filter 508, then a polarizing filter 509, then an optical axis adjustment optical system 510, and then an image-forming optical system 511, and is incident to a two-dimensional array detector 512.

As shown in FIG. 21 and FIG. 23, the spectroscopic unit base on the present invention constituted by the variable bandpass filters 421 and 422 and the variable bandpass filters 431 and 432 can be used, for example, as the variable bandpass filter 507.

Although the notch filter 508 is not essential, it is best to have it in the case in which the light source 501 or 504 is a single-wavelength light source.

Figure 25:
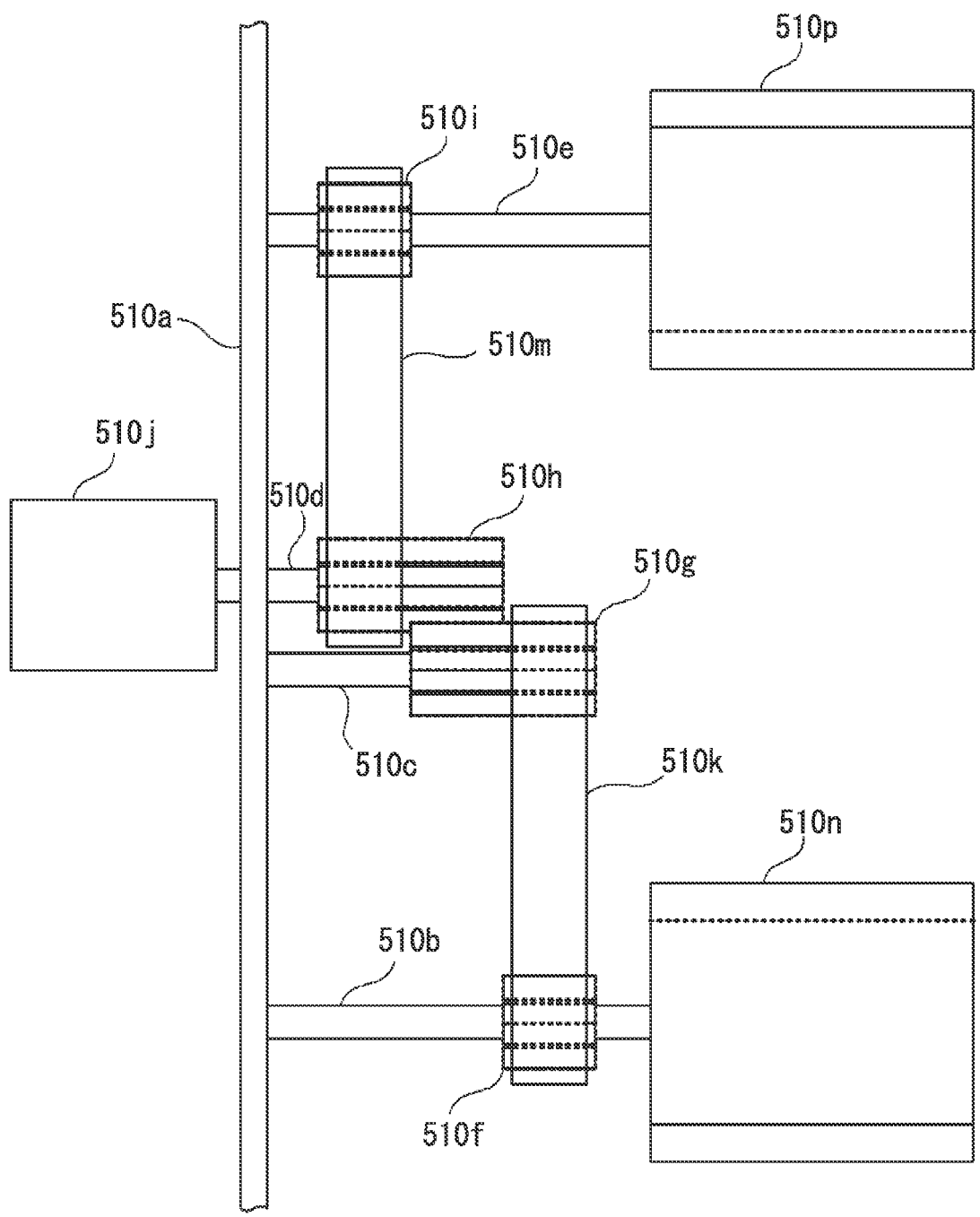
FIG. 25 is a diagram illustrating a side view of a constitution of an optical axis shift correction device used as the optical axis adjustment optical system 510 of FIG. 24.
Figure 26:
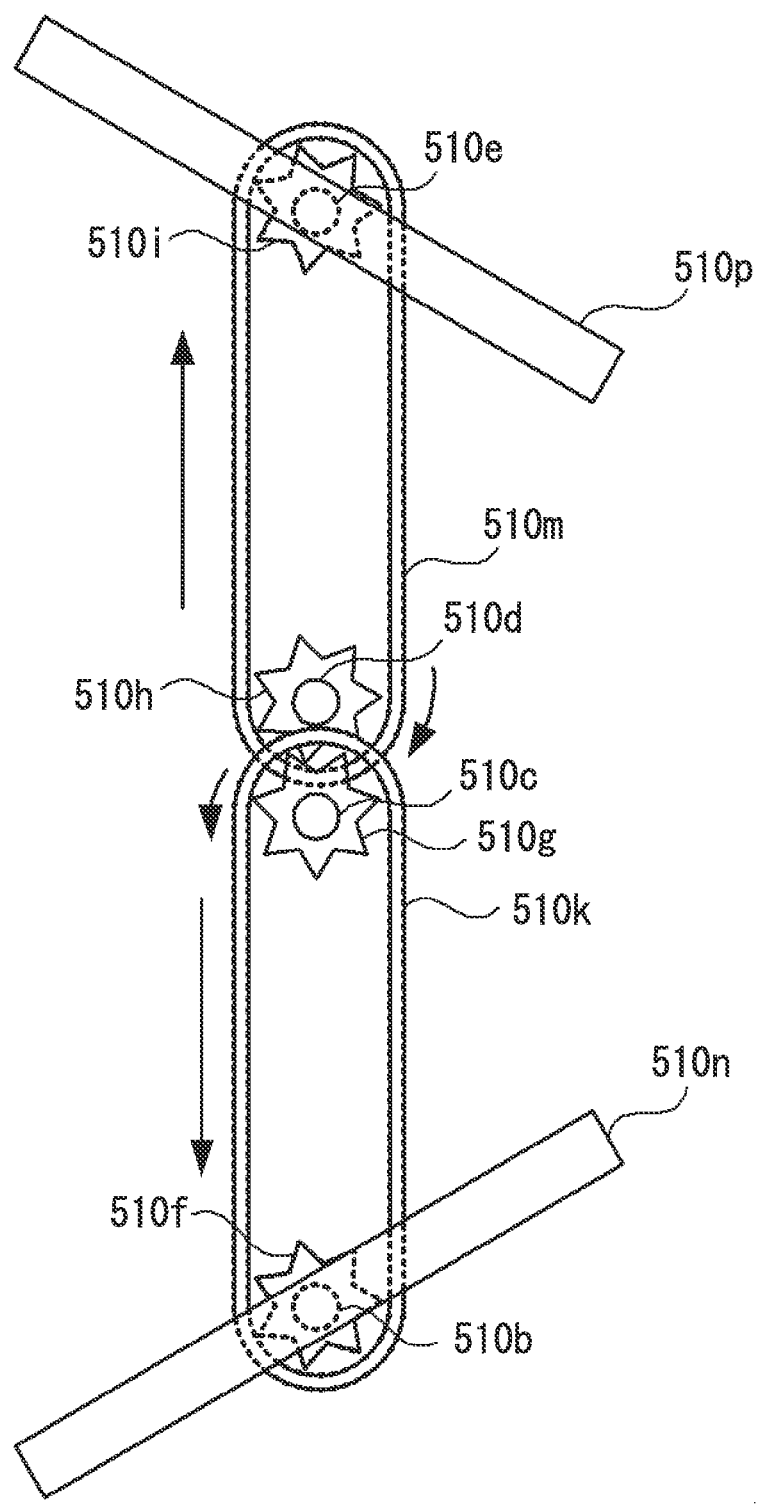
FIG. 26 is a diagram illustrating a top view of FIG. 25.

An optical axis shift correction device constituted as shown in FIGS. 25 and 26, for example, is used as the optical axis adjustment optical system 510. FIG. 25 shows a side view of the constitution, and FIG. 26 shows a top view thereof. In FIG. 25 and FIG. 26, four shafts 510b to 510e are mounted on a support plate 510a so as to smoothly rotate with, for example, intervening bearings. Pulleys 510f to 510i are fixed to the shafts 510b to 510e, respectively.

A rotational drive source (for example, a motor) is linked to the shaft 510d, the pulley 510f and the pulley 510g are linked via a belt 510k, the pulley 510h and the pulley 510i are linked via a belt 510m, and the pulley 510g and the pulley 510h are linked by direct contact between the outer peripheries thereof.

An optical filter 510n is mounted to the shaft 510b, and a corrective optical plate 510p is mounted to the shaft 510e.

In a constitution such as noted above, the rotation of the rotational drive source 510 is transmitted to the corrective optical plate 510p, via the transmission system of the shaft 510d to the pulley 510h, to the belt 510m, to the pulley 510i, and then to the shaft 510e to rotate the corrective optical plate 510p, and is transmitted to the optical filter 510n via the transmission system of the shaft 510d to the pulley 510h, to the pulley 510g, to the belt 510k, to the pulley 510f, and then to the shaft 510b to rotate the optical filter 510n. In this case, because the pulley 510g and the pulley 510h, as shown in FIG. 26, are linked by direct contact between the outer peripheries thereof, they rotate in mutually opposite directions.

Figure 27:
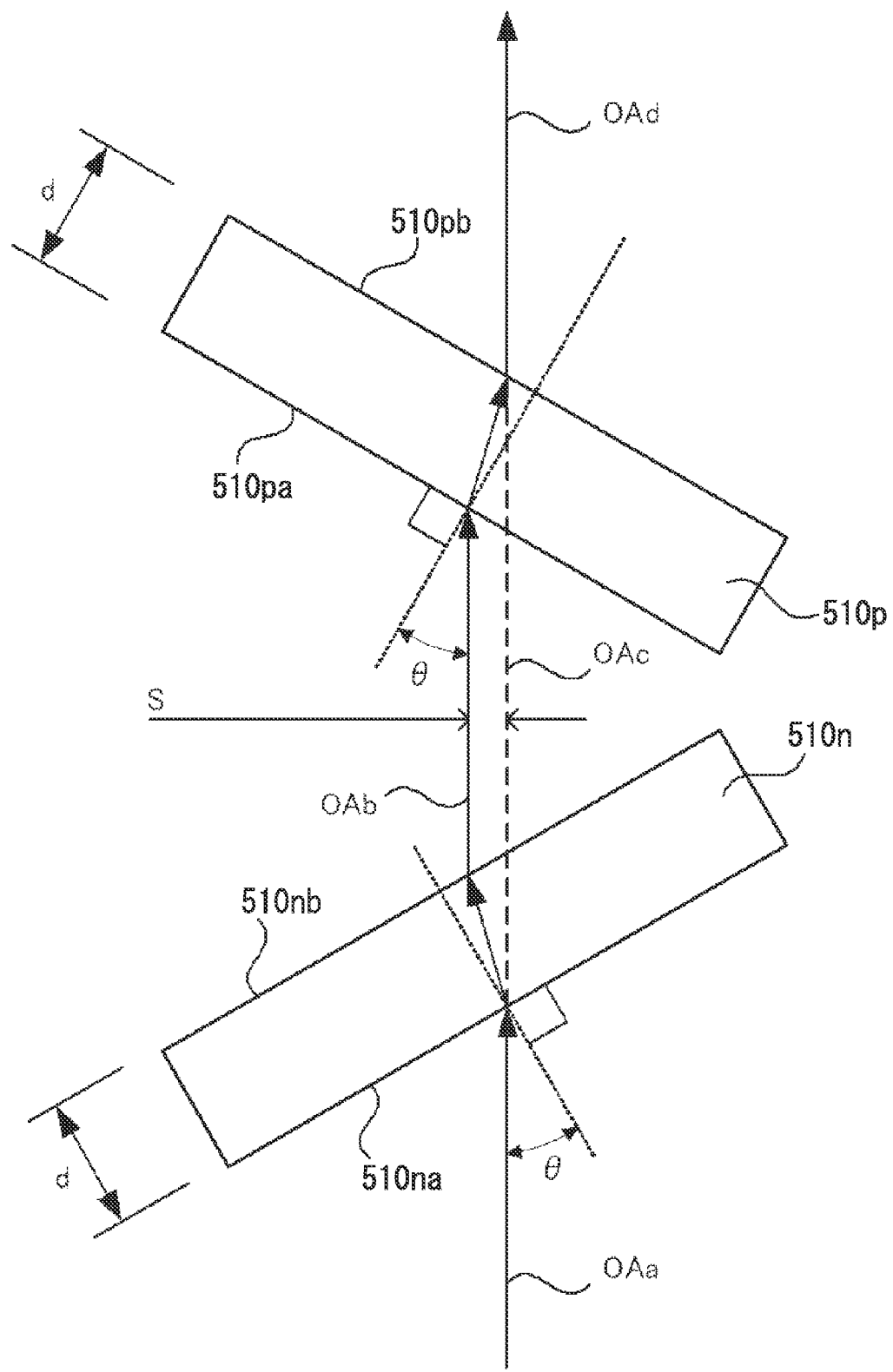
FIG. 27 is a diagram describing the light path, focusing on the optical filter 510n and the corrective optical plate 510p, which are optical components shown in FIG. 25.

FIG. 27 is a diagram describing the light path, focusing on the optical filter 510n and the corrective optical plate 510p, which are optical components shown in FIG. 25. In FIG. 27, the optical filter 510n is disposed at an angle of inclination that is rotated by an angle of θ in the counter-clockwise direction from a position that is perpendicular with respect to the optical axis OAa that is in the forward advance direction. In contrast, the corrective optical plate 510p is disposed at an angle of inclination that is rotated by an angle of θ in the clockwise direction from a position that is perpendicular with respect to the optical axis OAa that is in the forward advance direction.

Light, reaches the front surface 513a of the optical filter 513 along the optical axis OAa, and is incident to the optical filter 510n. Light that is incident to the optical filter 510n is refracted and transmitted within the optical filter 510n in accordance with Snell's law, and reaches the rear surface 513b of the optical filter rear surface 510n.

Light that has reached the rear surface 513b of the optical filter 510b is again refracted, in accordance with Snell's law, and proceeds along the optical axis OAb, which is parallel to the optical axis OAa, reaches the front surface 514a of the corrective optical plate 510p, and is incident to the corrective optical plate 510p. When this occurs, a shift occurs in the optical axis OAb by a distance of S with respect to the original optical axis OAc, which should be on a line extending from the optical axis OAa. This optical axis shift of S can be expressed as a function of inclination angle θ, the thickness d, and the refractive index n of the optical filter 510n.

The light that is incident to the front surface 514a of the corrective optical plate 514 is refracted, in accordance with Snell's law, in the direction that cancels out the optical axis shift by the distant S caused by passing through the optical filter 510n in accordance with the internal refractive index n thereof, and reaches the rear surface 514b of the corrective optical plate 510p.

The light that reaches the rear surface 514b of the corrective optical plate 510p is again refracted in accordance with Snell's law, and proceeds along the original optical axis OAd, which is a line extending from the optical axis OAa.

That is, by making the refractive index n and the thickness d of the corrective optical plate 510p the same as the refractive index n and the thickness of the optical filter 510n, and rotational driving the optical filter 510n and corrective optical plate 510p in a linked manner, so that the angle of inclination θ of the optical filter 510*n* in the counter-clockwise direction with respect to the optical axis OAa is always the same as the angle of inclination θ of the corrective optical plate 510*p* in the clockwise direction with respect to the optical axis OAd, the optical axis shift by the distance S caused by passing through the optical filter 510*n* is cancelled out, and the light exiting from the rear surface 514*b* of the corrective optical plate 510*p* is made to coincide with the original optical axis OAd that is a line extending from the optical axis OAa of incidence from the front surface 513*a* of the optical filter 510*n*.

By doing this, continuous measurement is possible while using a variable bandpass filter of the angular modulation type such as in the present invention. If it is desired to measure in real time while varying the incidence angle of the light, although an optical axis shift occurs, accompanying the change in the angle of incidence of the light, by applying the constitution shown in FIG. 25 and FIG. 26, because it is possible to make automatic correction of the optical axis shift, continuous measurement without breaks is possible.

Returning FIG. 24, a CMOS image sensor or CCD image sensor or the like can be used as the two-dimensional array detector 512.

The edge filter 506, the variable bandpass filter 507, the notch filter 508, the polarizing filter 509, the optical axis adjustment optical system 510, and the two-dimensional array detector 512 are connected to a controller 513.

The edge filter 506, the notch filter 508, and the polarizing filter 509 are controlled by the controller 513 to be inserted into or removed from the optical axis, as required. The variable bandpass filter 507, the optical axis adjustment optical system 510, the image-forming optical system 511, and the two-dimensional array detector 512 are controlled by the controller 513 so as to achieve desired conditions of the spectrally dispersed wavelength region and timing.

Figure 28:
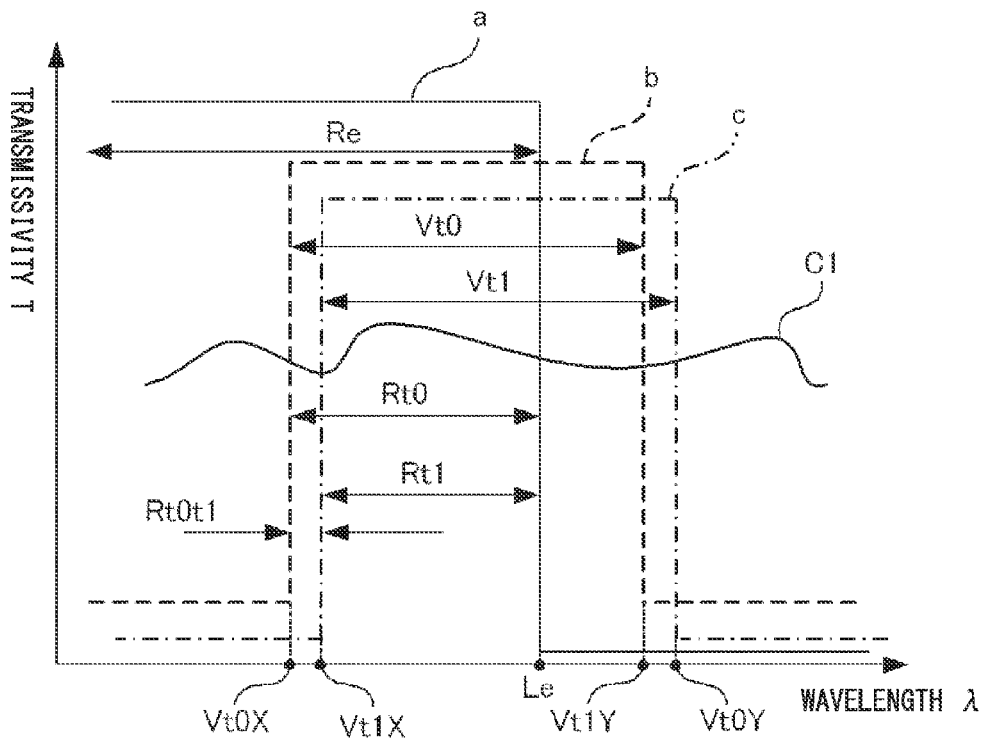
FIG. 28 is a diagram describing a wavelength region that is spectrally dispersed by the constitution of FIG. 24.

The operation in FIG. 24 will be described using FIG. 28 and FIG. 29. FIG. 28 is a diagram describing the wavelength region that is spectrally dispersed by the edge filter 506 and the variable bandpass filter 507. The horizontal axis represents the wavelength λ, and the vertical axis represents the transmissivity T.

In FIG. 28, the spectral wavelength region from t0 to t1 of C1 is spectrally dispersed. The solid line a indicates the light transmission region of the edge filter 506, this meaning that light in the short-wavelength region below the wavelength region Le.

The single-dot dashed line c indicates the transmission region of the variable bandpass filter 507. By modulating the transmission region, the condition of the dashed line b, in which the region of the wavelength range Vt0=Vt0Y−Vt0X is transmitted, and the condition of the single-dot dashed line c, in which the region of the wavelength range Vt1=Vt1Y−Vt1X is transmitted are created. In FIG. 28, although the solid line a, the dashed line b, and the single-dot dashed line c are drawn so that the transmissivities are mutually different, this is a convenience of description, and has no particular significance.

In the case of the dashed line b, because the transmitted wavelength region is formed by a long-wavelength side that the transmission region of the edge filter 506 and the transmission region of the variable bandpass filter 507, this is Rt0=Vt0X−Le. The amount of light in this condition is first measured, this amount of light being taken as E_Rt0.

Next, the amount of light in the case of the single-dot dashed line c is measured. In this case, the transmitted wavelength region is Rt1=Vt1X−Le, and the amount of light is taken as E_Rt1.

The amounts of light in the condition of the solid line a and the single-dot dashed line c, these being E_Rt0 and E_Rt1, are held by a storage function of the controller 513.

The controller 513 performs processing to subtract the amount of light E_Rt1 from the amount of light E_Rt0, the difference amount of light being calculated as E_Rt(0−1)=E_Rt0−E_Rt1.

In this case, E_Rt(0−1) means the amount of light in the wavelength region Rt0t1=Vt0X−Vt1X. That is, with respect to the spectrum C1, a spectral output in this wavelength region has been obtained. The above-noted "measurement of the amount of light" means a planar imaging by the two-dimensional array detector 512. By doing this, the controller 513 stores the measured amounts of light at each pixel in the two-dimensional array detector 512 and performs subtraction to output the spectral results for each of the pixels.

Next, a different region of the spectrum C1 is spectrally dispersed.

Figure 29:
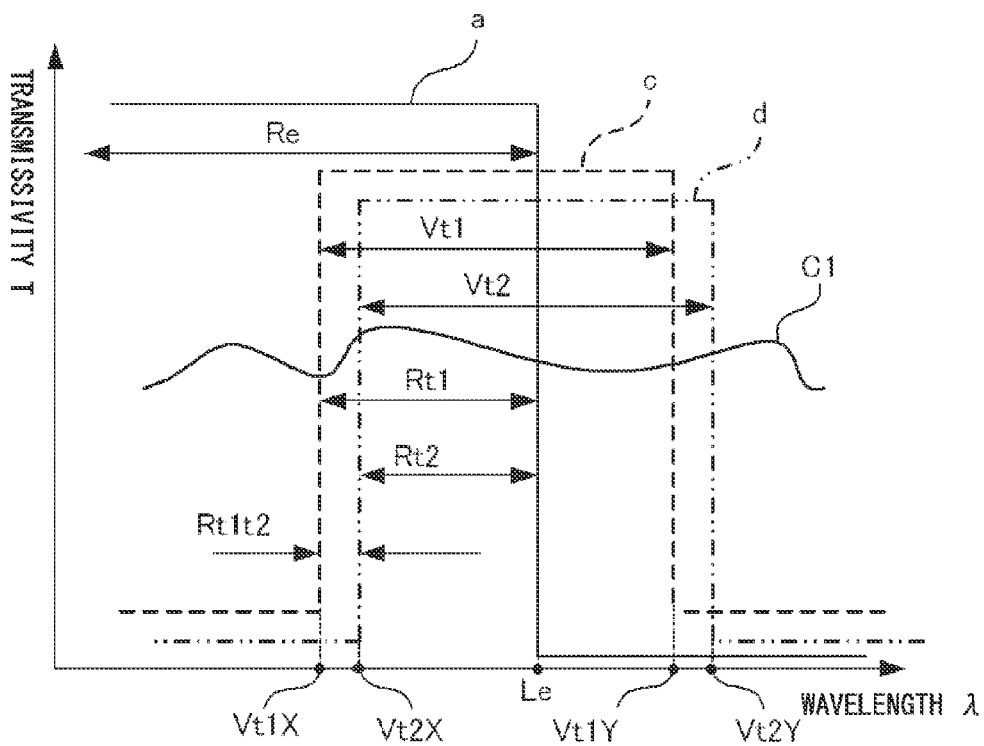
FIG. 29 is a diagram describing another wavelength region that is spectrally dispersed by the constitution of FIG. 24.
Figure 30:
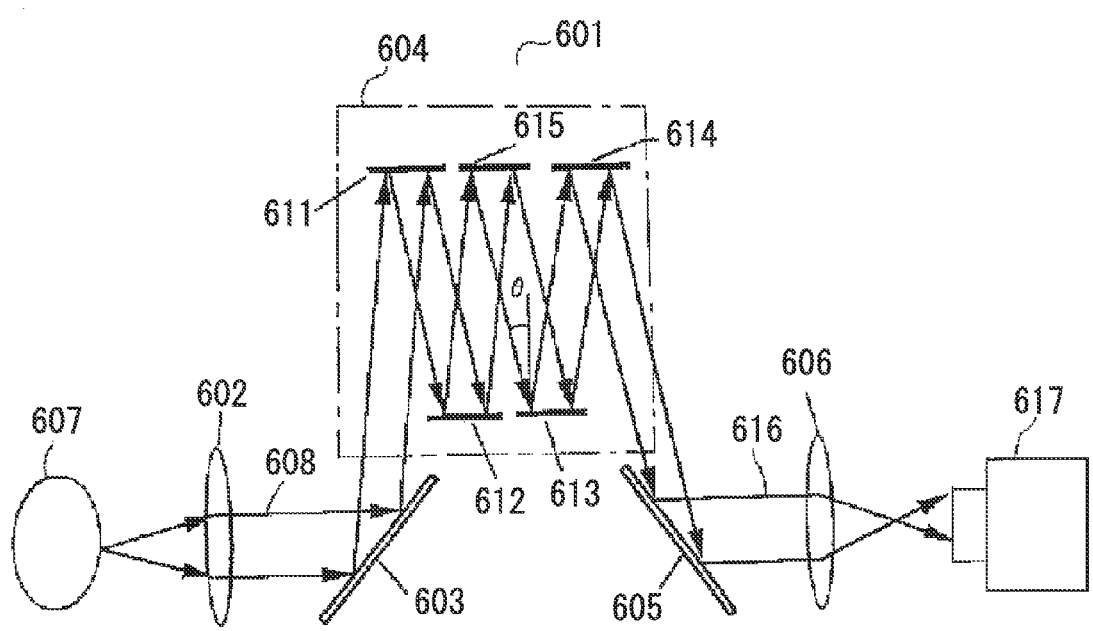
FIG. 30 is a drawing showing the constitution of a filter spectroscopic unit in accordance with the related art.

FIG. 29 is a diagram describing a wavelength region that indicates the condition in which the light transmission region of the variable passband filter 507 is modulated, so that transmission is done in a longer wavelength region. The horizontal axis represents the wavelength λ, and the vertical axis represents the transmissivity T.

In FIG. 29, the wavelength region from t1 to t2 of the spectrum C1 is spectrally dispersed. The solid line a indicates the light transmission region of the edge filter 506. The dashed line c indicates the transmission region of the variable bandpass filter 507, and the light amount E_Rt1 in this case is at this point stored in the controller 513. The double-dot dashed line d is the condition in which the variable bandpass filter 507 is controlled to modulate it so that light is transmitted in a longer wavelength region Vt2=Vt2Y−Vt2X.

In such a condition, calculation processing similar to that of FIG. 28 is performed. In this case, the net light transmission region is Rt1t2=Rt1−Rt2=(Le−Vt1X)−(Le−Vt2X).

The transmitted amount of light at this time is calculated as E_Rt(1−2)=E_Rt1−E_Rt2.

By the above, a spectral output on the long wavelength side with respect to the spectrum C1 is obtained.

By continuously repeating the execution of the processing operations described by FIG. 28 and FIG. 29, spectral processing is performed over the entire wavelength region of the spectrum C1.

By the constitution of FIG. 24, it is possible to constitution a compact, low-cost spectroscope with a relatively small number of components.

Additionally, by using a spectroscope constituted in this manner and the two-dimensional array detector 512, it is possible to perform two-dimensional (XY) planar spectral dispersion without a time delay, thereby enabling spectral dispersion of the same wavelength region for a given measurement time.

It is also possible to perform high-speed spectral dispersion, based on the imaging speed of the two-dimensional array detector 512.

Additionally, because the control precision itself of the transmission region of the variable bandpass filter 507 becomes the wavelength resolution, high wavelength resolution is achieved. Also, because the control precision itself of the variable bandpass filter 507 becomes the wavelength sampling capability and the optical wavelength resolution, high wavelength sampling capability and optical wavelength resolution are obtained.

Although the descriptions of FIG. 28 and FIG. 29 assumed the use of a short-pass filter constituted so as to transmit light in a short-wavelength region as the edge pass filter 506, a long-pass filter that transmits light in a long-wavelength region may be used.

Also, by using the polarizing filter 509 as shown in FIG. 24, it is possible to perform spectral dispersion with polarization dependency.

By using a polarizing filter 509 such as shown in FIG. 24, it is possible to perform spectral dispersion while controlling the polarization direction.

By constituting the image-forming optical system 511 of FIG. 24 as a confocal optical system, it is possible to measure in the depth direction of the object under measurement 503.

As described above, according to the present invention, with a relatively small number of components, it is possible to implement a spectroscope capable of correcting the optical axis shift, this being suitable for correction of optical axis shift in various optical apparatuses, such as spectroscopes and microscopes.

Seventh Preferred Embodiment

Figure 31:
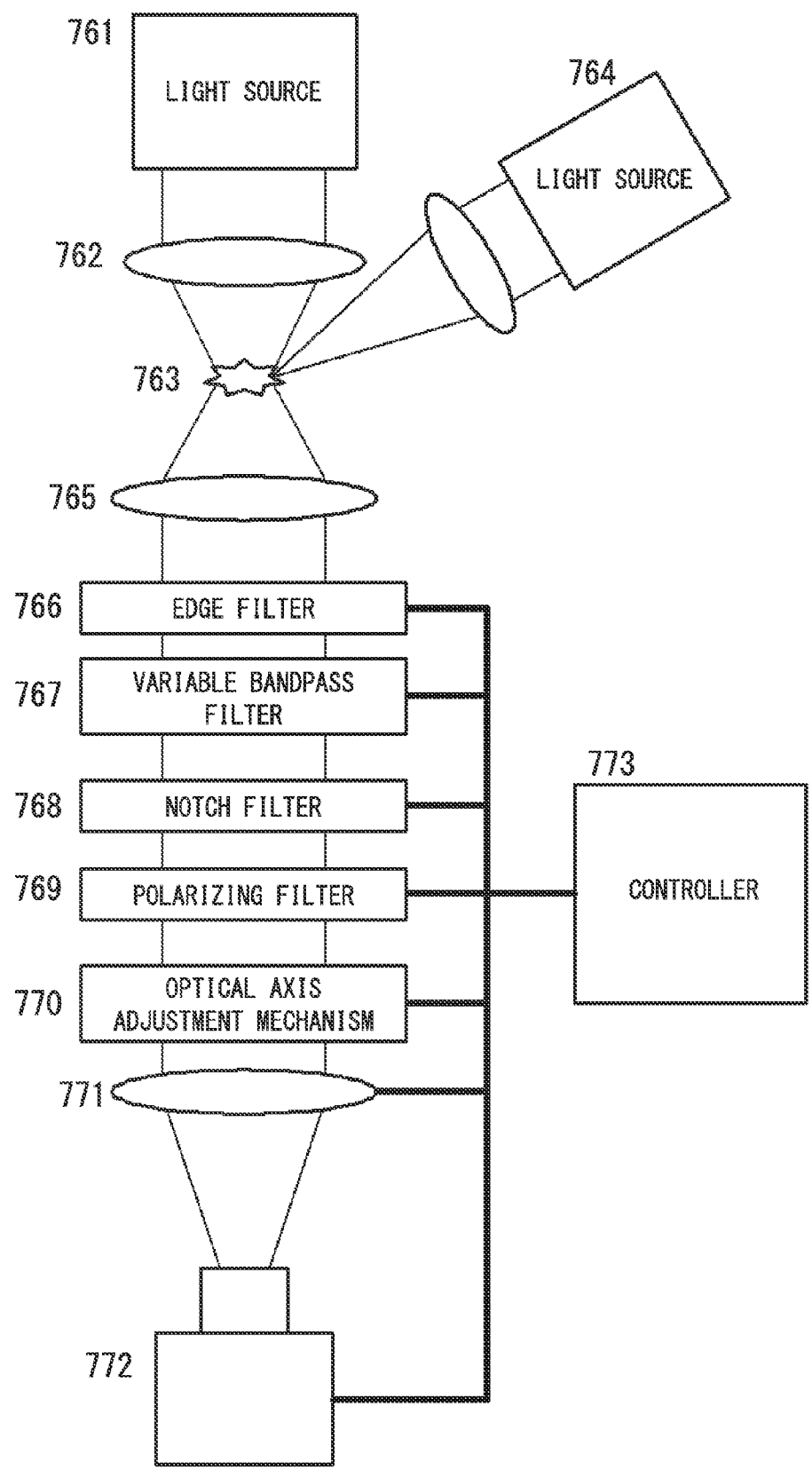
FIG. 31 is a constitution diagram describing a seventh preferred embodiment of the present invention.

FIG. 31 is a constitution diagram describing a seventh preferred embodiment of the present invention. In FIG. 31, the output light of the light source 761 illuminates the object under measurement 763, which is the sample, via the light illumination optical system 762. In illuminating the object under measurement 763, illumination may be done from a position that is shifted from the optical axis, such as a light source 764.

It is sufficient that there be at least one of the light sources 761 and 764, and the light sources 761 and 764 may be single-wavelength light sources such as lasers, or alternatively may be wideband wavelength light sources.

The light from the object under measurement 763 is broadened by the objective lens optical system 765 and, by the action of an edge filter 766, is limited to the short-wavelength region or long-wavelength region thereof.

The output light of the edge filter 766 is spectrally dispersed by passing through a variable bandpass filter 767. The output light that has been spectrally dispersed by the variable bandpass filter 767 passes through the optical path that is formed by a notch filter 768, then a polarizing filter 769, then an optical axis adjustment optical system 770, and then an image-forming optical system 771, and is incident to a two-dimensional array detector 772.

Although the notch filter 768 is not essential, it is best to have it in the case in which the light source 761 or 764 is a single-wavelength light source.

An optical interference type or light incidence angle tuning type filter can be used as the variable bandpass filter 767.

A CMOS image sensor or CCD image sensor or the like can be used as the two-dimensional array detector 772.

The edge filter 766, the variable bandpass filter 767, the notch filter 768, the polarizing filter 769, the optical axis adjustment optical system 770, the image-forming optical system 771, and the two-dimensional array detector 772 are connected to a controller 773.

The edge filter 766, the notch filter 768, and the polarizing filter 769 are controlled by the controller 773 to be inserted into or removed from the optical axis, as required. The variable bandpass filter 767, the optical axis adjustment optical system 770, the image-forming optical system 771, and the two-dimensional array detector 772 are controlled by the controller 773 so as to achieve desired conditions of the spectrally dispersed wavelength region and timing.

Figure 32:
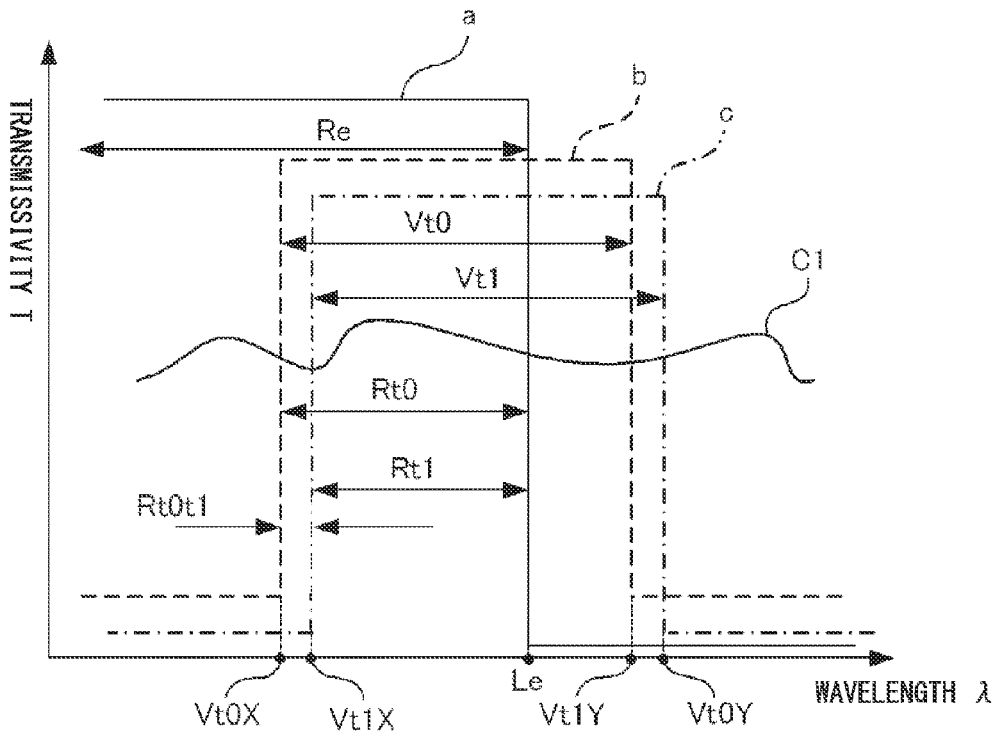
FIG. 32 is a diagram describing a wavelength region that is spectrally dispersed by the constitution of FIG. 31.

The operation in FIG. 31 will be described using FIG. 32 and FIG. 33. FIG. 32 is a diagram describing the wavelength region that is spectrally dispersed by the edge filter 766 and the variable bandpass filter 767. The horizontal axis represents the wavelength λ, and the vertical axis represents the transmissivity T.

In FIG. 32, the spectral wavelength region from t0 to t1 of C1 is spectrally dispersed. The solid line a indicates the light transmission region of the edge filter 766, this meaning that light in the short-wavelength region below the wavelength region Le.

The single-dot dashed line c indicates the transmission region of the variable bandpass filter 767. By modulating the transmission region, the condition of the dashed line b, in which the region of the wavelength range Vt0=Vt0Y–Vt0X is transmitted, and the condition of the single-dot dashed line c, in which the region of the wavelength range Vt1=Vt1Y–Vt1X is transmitted are created. In FIG. 32, although the solid line a, the dashed line b, and the single-dot dashed line c are drawn so that the transmissivities are mutually different, this is a convenience of description, and has no particular significance.

In the case of the dashed line b, because the transmitted wavelength region is formed by a long-wavelength side that the transmission region of the edge filter 766 and the transmission region of the variable bandpass filter 767, this is Rt0=Vt0X–Le. The amount of light in this condition is first measured, this amount of light being taken as E_Rt0.

Next, the amount of light in the case of the single-dot dashed line c is measured. In this case, the transmitted wavelength region is Rt1=Vt1X–Le, and the amount of light is taken as E_Rt1.

The amounts of light in the condition of the solid line a and the single-dot dashed line c, these being E_Rt0 and E_Rt1, are held by a storage function of the controller 773.

The controller 773 performs processing to subtract the amount of light E_Rt1 from the amount of light E_Rt0, the difference amount of light being calculated as E_Rt(0−1)=E_Rt0−E_Rt1.

In this case, E_Rt(0−1) means the amount of light in the wavelength region Rt0t1=Vt0X–Vt1X. That is, with respect to the spectrum C1, a spectral output in this wavelength region has been obtained. The above-noted "measurement of the amount of light" means a planar imaging by the two-dimensional array detector 772. By doing this, the controller 773 stores the measured amounts of light at each pixel in the two-dimensional array detector 772 and performs subtraction to output the spectral results for each of the pixels.

Next, a different region of the spectrum C1 is spectrally dispersed.

Figure 33:
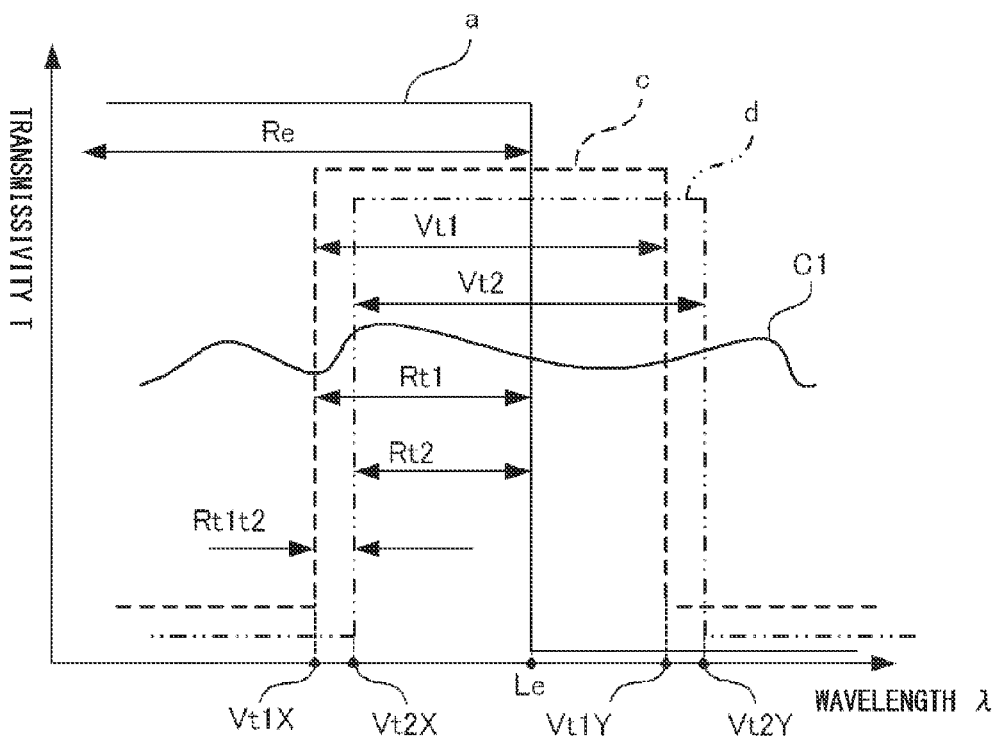
FIG. 33 is a diagram describing another wavelength region that is spectrally dispersed by the constitution of FIG. 31.
Figure 34:
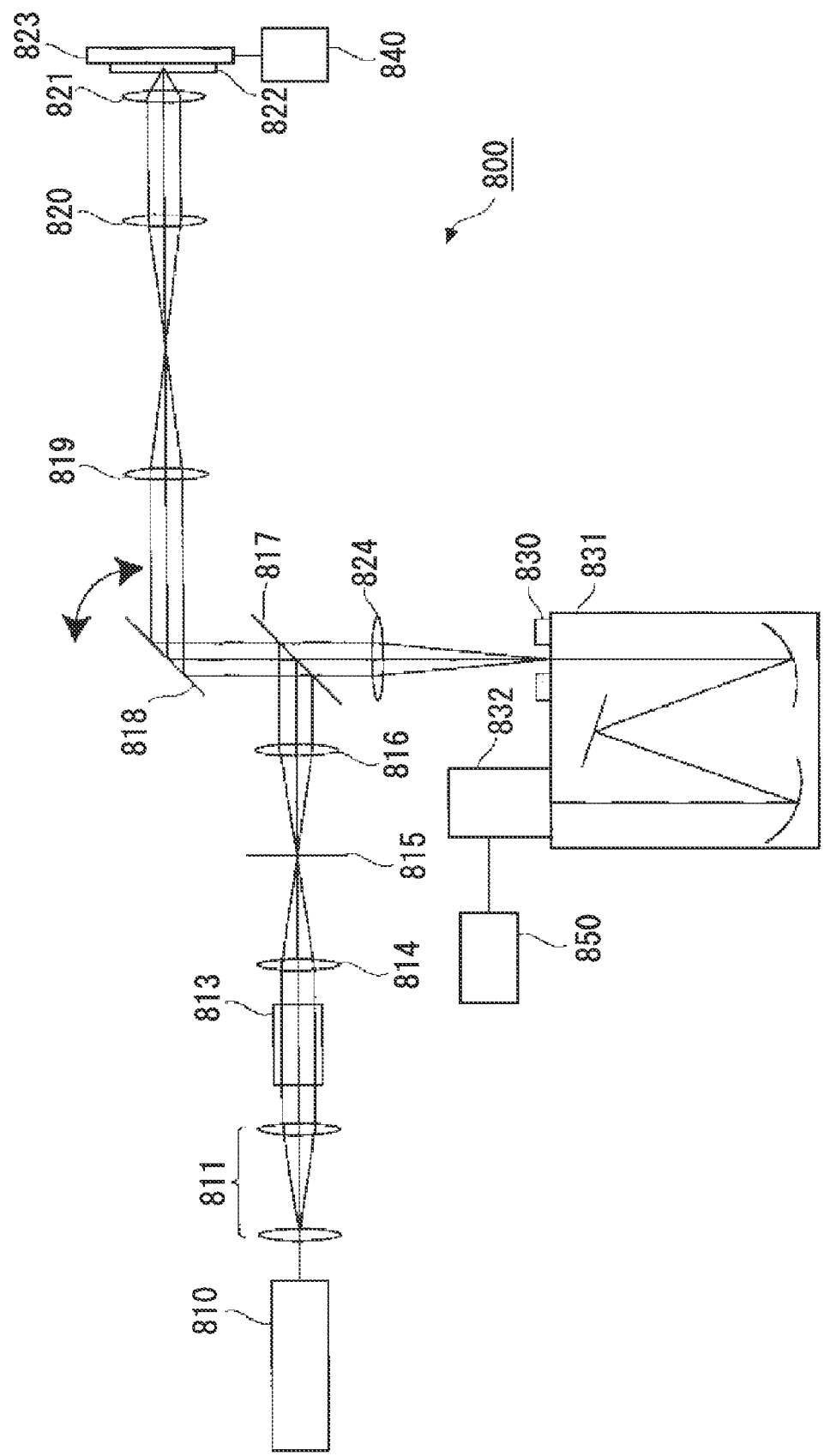
FIG. 34 is a drawing illustrating a constitution of a laser microscope in accordance with the related art.

FIG. 33 is a diagram describing a wavelength region that indicates the condition in which the light transmission region of the variable passband filter 767 is modulated, so that transmission is done in a longer wavelength region. The horizontal axis represents the wavelength λ, and the vertical axis represents the transmissivity T.

In FIG. 33, the wavelength region from t1 to t2 of the spectrum C1 is spectrally dispersed. The solid line a indicates the light transmission region of the edge filter 766. The dashed line c indicates the transmission region of the variable bandpass filter 767, and the light amount E_Rt1 in this case is at this point stored in the controller 773. The double-dot dashed line d is the condition in which the variable bandpass filter 767 is controlled to modulate it so that light is transmitted in a longer wavelength region Vt2=Vt2Y–Vt2X.

In such a condition, calculation processing similar to that of FIG. 32 is performed. In this case, the net light transmission region is Rt1t2=Rt1−Rt2=(Le−Vt1X)−(Le−Vt2X).

The transmitted amount of light at this time is calculated as E_Rt(1−2)=E_Rt1−E_Rt2.

By the above, a spectral output on the long wavelength side with respect to the spectrum C1 is obtained.

By continuously repeating the execution of the processing operations described by FIG. 32 and FIG. 33, spectral processing is performed over the entire wavelength region of the spectrum C1.

By the constitution of FIG. 31, it is possible to constitution a compact, low-cost spectroscope with a relatively small number of components using the edge filter 766 and the variable bandpass filter 767.

Additionally, by using a spectroscope constituted in this manner and the two-dimensional array detector 772, it is possible to perform two-dimensional (XY) planar spectral dispersion without a time delay, thereby enabling spectral dispersion of the same wavelength region for a given measurement time.

It is also possible to perform high-speed spectral dispersion, based on the imaging speed of the two-dimensional array detector 772.

Additionally, because the control precision itself of the transmission region of the variable bandpass filter 767 becomes the wavelength resolution, high wavelength resolution is achieved. Also, because the control precision itself of the variable bandpass filter 767 becomes the wavelength sampling capability and the optical wavelength resolution, high wavelength sampling capability and optical wavelength resolution are obtained.

Although the descriptions of FIG. 32 and FIG. 33 assumed the use of a short-pass filter constituted so as to transmit light in a short-wavelength region as the edge pass filter 766, a long-pass filter that transmits light in a long-wavelength region may be used.

Also, by using the polarizing filter 769 as shown in FIG. 31, it is possible to perform spectral dispersion with polarization dependency.

By using a polarizing filter 769 such as shown in FIG. 31, it is possible to perform spectral dispersion while controlling the polarization direction.

By constituting the image-forming optical system 771 of FIG. 31 as a confocal optical system, it is possible to measure in the depth direction of the object under measurement 763.

Additionally, by using a spectroscope constituted in this manner in a microscope, it is possible to implement a microscope having the above-noted superior spectroscopic characteristics and, by using the image-forming optical system 771 shown in FIG. 31 as a confocal optical system, it is possible to implement a confocal microscope capable of measurement in the depth direction of the object under measurement 763.

As described above, according to the present invention, with a relatively small number of components, it is possible to implement a compact spectroscope capable of high-speed spectral dispersion with high wavelength resolution of a two-dimensional (XY) plan, this being suitable for measurement of Raman shift such as in Raman scattering or SERS and the like. According to the present invention, high-speed spectral dispersion with a high wavelength sampling capability is possible of a two-dimensional (XY) plane.

The present invention implements a microscope spectrometer capable of high-speed spectral dispersion with a wavelength resolution having a pre-established width. With a relatively simple constitution, the present invention provides an optical axis correction device capable of correcting optical axis shift. With a relatively simple constitution, the present invention provides a spectroscope capable of continuously changing the center wavelength. With a relatively small number of components, the present invention provides a compact, low-cost spectroscope capable of high-speed spectral dispersion with a high wavelength resolution of a two-dimensional (XY) plane, and a microscope that uses the spectroscope. The present invention implements a microscope spectrometer capable of high-speed spectral dispersion with a wavelength sampling capability and optical wavelength resolution having a pre-established width.

The microscope spectrometer in accordance with a preferred embodiment of the present invention is effective with regard to the points of having a first variable bandpass filter means, which has a variable wavelength passband that transmits scattered light that has been formed into a parallel beam by a first optical means, transmitting light of the incident scattered light in a pre-established wavelength passband, a two-dimensional detection means imaging the scattered light in the wavelength passband, and a control means controlling the timing of the imaging by the two-dimensional detection means and changes the wavelength passband of the first variable bandpass filter means in accordance with the timing, thereby enabling spectrometry of a two-dimensional region of a sample at a high speed and with a pre-established wavelength resolution. Additionally, because there is no Z-direction focal point change in the optical system used in this constitution, the effect of obtaining a sharp spectral image that is not out-of-focus is achieved.

According to the optical axis shift correction device in accordance with a preferred embodiment of the present invention, optical axis shift correction is possible with a relatively simple constitution.

According to the spectroscope in accordance with a preferred embodiment of the present invention, it is possible to change the center wavelength of the spectroscope continuously.

According to the microscope in accordance with a preferred embodiment of the present invention, it is possible to implement a small, low-cost spectroscope that, with a relatively small number of components, is capable of high-speed spectrometry with a high wavelength resolution in a two-dimensional (XY) plane, and a microscope that uses the spectroscope.

As used herein, the following directional terms "forward, rearward, above, downward, right, left, vertical, horizontal, below, transverse, row and column" as well as any other similar directional terms refer to those directions of an apparatus equipped with the present invention. Accordingly, these terms, as utilized to describe the present invention should be interpreted relative to an apparatus equipped with the present invention.

The term "configured" is used to describe a component, unit or part of a device includes hardware and/or software that is constructed and/or programmed to carry out the desired function.

Moreover, terms that are expressed as "means-plus function" in the claims should include any structure that can be utilized to carry out the function of that part of the present invention.

The term "unit" is used to describe a component, unit or part of a hardware and/or software that is constructed and/or programmed to carry out the desired function. Typical examples of the hardware may include, but are not limited to, a device and a circuit.

While preferred embodiments of the present invention have been described and illustrated above, it should be understood that these are examples of the present invention and are not to be considered as limiting. Additions, omissions, substitutions, and other modifications can be made without departing from the scope of the present invention. Accordingly, the present invention is not to be considered as being limited by the foregoing description, and is only limited by the scope of the claims.

What is claimed is:

1. A microscope spectrometer in which, when an excitation light from a light source illuminates a sample, a light emitted from the sample that enters a microscope is analyzed, the microscope spectrometer comprising:
    a first optical means that forms the light emitted from the sample as a parallel beam;
    a first variable bandpass filter means of incident light angle tuned type having a variable wavelength passband that transmits incident light which, of the parallel beam of incident light, is light of a pre-established wavelength passband;
    a second variable bandpass filter means of incident light angle tuned type having a variable wavelength passband that transmits incident light which, of the light incident from the first variable bandpass filter means, is light of a pre-established wavelength passband;
    an optical axis adjustment means that is composed of an optical plate that transmits light and corrects the position shift of the optical axis of the scattered light in a two-dimensional plane that is caused by the first variable bandpass filter means and the second variable bandpass filter means;
    a two-dimensional array light detection means that images the light in the wavelength passband; and
    a control means that controls the timing of the imaging by the two-dimensional array light detection means and controls the first variable bandpass filter means and the second variable bandpass filter means to change, in accordance with the timing, the wavelength passband of the first variable bandpass filter means and the second variable bandpass filter means, the control means further controlling the optical axis adjustment means,
    wherein the control means controls the timing of the imaging by the two-dimensional array light detection means to turn ON imaging at a time the control means controls the first variable bandpass filter means and the second variable bandpass filter means to change the pre-established wavelength passband to a changed wavelength passband for each of the first variable bandpass filter means and the second variable bandpass filter means, and to turn OFF the imaging by the two-dimensional array light detection means before an end of time each of the first variable bandpass filter means and the second variable bandpass filter means is transmitting the incident light at the changed wavelength passband, and
    wherein the first optical means, the first variable bandpass filter, the second variable bandpass filter, and the two-dimensional array light detection means are disposed to have a common optical axis in an unbranched straight line.

2. The microscope spectrometer according to claim 1, wherein the control means controls the first variable bandpass filter means to sweep a pre-established plurality of wavelength passbands.

3. The microscope spectrometer according to claim 1, wherein the control means controls the two-dimensional array light detection means so as to image the light at a pre-established time interval, and controls the first variable wavelength bandpass filter means to change the wavelength passband by a pre-established wavelength band interval.

4. The microscope spectrometer according to claim 1, wherein
    the control means varies the wavelength passband of the second variable bandpass filter means so that the wavelength passband of the first variable bandpass filter means and the wavelength passband of the second variable bandpass filter means overlap.

5. The microscope spectrometer according to claim 1, further comprising:
    a polarization means that polarizes the light that has passed through the first variable bandpass filter means or the second variable bandpass filter means to a pre-established polarization direction, wherein
    the control means changes the polarization direction of the polarization means.

6. An optical axis shift correction device that corrects the shift of the optical axis caused by an optical filter provided in the optical system, comprising:
    a corrective optical plate having a thickness and a refractive index that are equal to the thickness and the refractive index of the optical filter; and
    a rotational drive mechanism that includes a shaft, a pulley fixed to the shaft, and a rotational drive source linked to the shaft,
    wherein the optical filter and the corrective optical plate are configured to move in a linked manner via the shaft and the pulley,
    wherein the rotational drive mechanism is configured so that a rotation of the rotational drive source is transmitted to the optical filter and the corrective optical plate,
    wherein the optical filter and the corrective optical plate are configured to rotate by equal angles of inclination to the optical axis in mutually different directions, and
    wherein the rotational drive mechanism is configured to automatically correct an optical axis shift, which occurs accompanying a measurement in real time while varying an incidence angle of a light, by rotationally driving the optical filter and the corrective optical plate in a linked manner using the rotational drive source and the pulley.

7. The optical axis shift correction device according to claim 6, wherein rotational drive mechanism rotationally drives the optical filter and the corrective optical plate using separate individual sources of rotational drive.

8. A spectroscope comprising:
    a first filter group constituted by a first rectangular filter support plate having a rotating shaft for rotating the first filter support plate with an arbitrary angle and at least two variable bandpass filters that are fixed to the first filter support plate in parallel with each other;
    a second filter group constituted by a second rectangular filter support plate having a rotating shaft for rotating the second filter support plate with an arbitrary angle and at least two variable bandpass filters that are fixed to the second filter support plate in parallel with each other; and a rotating mechanism that rotationally drive the first filter group and the second filter group the first filter group and the second filter group cross the optical axis at desired rotational angles in mutually different directions, wherein a light that is incident to the first filter group is refracted in accordance with a refractive index within the first filter group and the second filter group and transmitted through the first filter group and the second filter group in accordance with Snell's law.

9. The spectroscope according to claim 8, wherein each of the variable bandpass filters in the filter groups is mounted so as to be independently rotatable.

10. A spectroscope comprising:

a light source that illuminates a sample;

an edge filter that limits a transmission region of a passing light to a short-wavelength region below a wavelength region Le or a long-wavelength region above a wavelength region Le;

a variable bandpass filter of an optical interference type that selects a desired wavelength region of reflected light from the sample;

a two-dimensional array detector onto which light that has passed through the variable bandpass filter is incident; and a controller that shifts the wavelength region of the variable bandpass filter from a wavelength range Vt0=Vt0Y−Vt0X to a wavelength range Vt1=Vt1Y−Vt1X, calculates a difference ERt(0−1)=ERt0−ERt1 that means an amount of light in a wavelength region Rt0t1=Vt0X−Vt1X based on the detected output ERt0 (a wavelength range is Rt0=Vt0X−Le) in a wavelength range Vt0 at each element of the two-dimensional detector before the shift and the detected output ERt1 (a wavelength range is Rt1=Vt1X−Le) in a wavelength range Vt1 at each element of the two-dimensional detector after the shift, and converts the difference into a spectral output.

11. A microscope comprising:

a light source that illuminates a sample;

an edge filter that limits a transmission region of a passing light to a short-wavelength region below a wavelength region Le or a long-wavelength region above a wavelength region Le;

a variable bandpass filter of an optical interference type that selects a desired wavelength region of reflected light from the sample;

a two-dimensional array detector onto which light that has passed through the variable bandpass filter is incident;

an image-forming optical system that forms an image of the light passing through the variable bandpass filter onto a light-receiving surface of the two-dimensional array detector; and a controller that shifts the wavelength region of the bandpass filter from a wavelength range Vt0=Vt0Y−Vt0X to a wavelength range Vt1=Vt1Y−Vt1X, calculates a difference ERt(0−1)=ERt0−ERt1 that means an amount of light in a wavelength region Rt0t1=Vt0X−Vt1X based on the detected output E_Rt0 (a wavelength range is Rt0=Vt0X−Le) in a wavelength range Vt0 at each element of the two-dimensional array detector before the shift and the detected output E_Rt1 (a wavelength range is Rt1=Vt1X−Le) in a wavelength range Vt1 at each element of the two-dimensional detector after the shift, and converts the difference into a spectral output.

12. The microscope according to claim 11, wherein the image-forming optical system is a confocal optical system.

* * * * *